United States Patent
Zolotukhin et al.

(10) Patent No.: US 11,702,673 B2
(45) Date of Patent: Jul. 18, 2023

(54) METHODS OF ENHANCING BIOLOGICAL POTENCY OF BACULOVIRUS SYSTEM-PRODUCED RECOMBINANT ADENO-ASSOCIATED VIRUS

(71) Applicant: University of Florida Research Foundation, Incorporated, Gainesville, FL (US)

(72) Inventors: Sergei Zolotukhin, Gainesville, FL (US); Oleksandr Kondratov, Gainesville, FL (US)

(73) Assignee: University of Florida Research Foundation, Incorporated, Gainesville, FL (US)

( * ) Notice: Subject to any disclaimer, the term of this patent is extended or adjusted under 35 U.S.C. 154(b) by 785 days.

(21) Appl. No.: 16/657,959

(22) Filed: Oct. 18, 2019

(65) Prior Publication Data
US 2020/0123572 A1    Apr. 23, 2020

Related U.S. Application Data

(60) Provisional application No. 62/747,481, filed on Oct. 18, 2018.

(51) Int. Cl.
| | |
|---|---|
| *C12N 15/86* | (2006.01) |
| *C12N 7/00* | (2006.01) |
| *C07K 14/075* | (2006.01) |
| *C12N 5/07* | (2010.01) |

(52) U.S. Cl.
CPC ............ *C12N 15/86* (2013.01); *C07K 14/075* (2013.01); *C12N 5/0601* (2013.01); *C12N 7/00* (2013.01); *C12N 2710/14041* (2013.01); *C12N 2710/14143* (2013.01); *C12N 2710/14144* (2013.01); *C12N 2750/14123* (2013.01); *C12N 2750/14143* (2013.01); *C12N 2750/14151* (2013.01)

(58) Field of Classification Search
CPC ........ C12N 15/86; C12N 5/0601; C12N 7/00; C12N 2710/14041; C12N 2710/14143; C12N 2710/14144; C12N 2750/14123; C12N 2750/14143; C12N 2750/14151; C12N 2840/10; C07K 14/075; C07K 14/005
See application file for complete search history.

(56) References Cited

U.S. PATENT DOCUMENTS

| | | | |
|---|---|---|---|
| 7,250,496 B2 | 7/2007 | Bentwich | |
| 7,271,002 B2 | 9/2007 | Kotin et al. | |
| 7,927,585 B2 | 4/2011 | Snyder | |
| 8,163,543 B2 | 4/2012 | Urabe et al. | |
| 10,837,027 B2* | 11/2020 | Lubelski | C12N 15/86 |
| 11,384,364 B2* | 7/2022 | Zolotukhin | C12N 15/86 |
| 2006/0286545 A1 | 12/2006 | Weber et al. | |
| 2007/0015238 A1 | 1/2007 | Snyder et al. | |
| 2009/0093426 A1 | 4/2009 | Soutscheck et al. | |
| 2009/0191597 A1 | 7/2009 | Samulski et al. | |
| 2012/0028357 A1 | 2/2012 | Urabe et al. | |
| 2012/0100606 A1 | 4/2012 | Zolotukhin et al. | |
| 2012/0322861 A1 | 12/2012 | Byrne et al. | |
| 2013/0102040 A1 | 4/2013 | Radakovits et al. | |
| 2015/0065562 A1 | 3/2015 | Yazicioglu et al. | |
| 2016/0199513 A1 | 7/2016 | Bancel et al. | |
| 2020/0123572 A1 | 4/2020 | Zolotukhin et al. | |
| 2021/0222194 A1 | 7/2021 | Zolotukhin et al. | |

FOREIGN PATENT DOCUMENTS

| | | |
|---|---|---|
| CN | 101287837 A | 10/2008 |
| CN | 103849629 A | 6/2014 |
| CN | 101287837 B | 3/2015 |
| EA | 20969 B1 | 3/2015 |
| JP | 2009-512436 A | 3/2009 |
| RU | 2457252 C2 | 7/2012 |
| WO | WO 2007/046703 A2 | 4/2007 |
| WO | WO 2015/137802 A1 | 9/2015 |
| WO | WO 2017/181162 A1 | 10/2017 |

OTHER PUBLICATIONS

Kondratov O, Marsic D, Crosson SM, Mendez-Gomez HR, Moskalenko O, et al., Agbandje-McKenna M, Zolotukhin S. Direct Head-to-Head Evaluation of Recombinant Adeno-associated Viral Vectors Manufactured in Human versus Insect Cells. Mol Ther. Dec. 6, 2017;25(12):2661-2675. Epub Aug. 10, 2017. (Year: 2017).*
Extended European Search Report dated Nov. 20, 2019 for Application No. 17783347.2.
International Search Report and Written Opinion for Application No. PCT/US2017/027832 dated Aug. 7, 2017.
International Preliminary Report on Patentability for Application No. PCT/US2017/027832 dated Oct. 25, 2018.

(Continued)

*Primary Examiner* — Rachel B Gill

(74) *Attorney, Agent, or Firm* — Wolf, Greenfield & Sacks, P.C.

(57) ABSTRACT

Provided herein are methods and compositions useful in the production of recombinant AAV (rAAV) in host producer cells, such as insect cells. In some embodiments, methods, uses and compositions are provided that comprise recombinant VP1 genes comprising modified Kozak sequences to express AAV VP1 proteins in amounts that are useful for producing infective rAAV particles. These infective rAAV particles may comprise a gene of interest.

30 Claims, 26 Drawing Sheets

Specification includes a Sequence Listing.

(56) References Cited

OTHER PUBLICATIONS

Invitation to Pay Additional Fees dated Aug. 10, 2021 for International Application No. PCT/US2021/029749.
International Search Report and Written Opinion dated Oct. 27, 2021 for International Application No. PCT/US2021/029749.
International Preliminary Report on Patentability dated Nov. 10, 2022 for International Application No. PCT/US2021/029749.
Aslanidi et al., An inducible system for highly efficient production of recombinant adeno-associated virus (rAAV) vectors in insect Sf9 cells. Proc Natl Acad Sci USA. Mar. 31, 2009;106(13):5059-64. doi: 10.1073/pnas.0810614106. Epub Mar. 11, 2009.
Kohlbrenner et al., Successful production of pseudotyped rAAV vectors using a modified baculovirus expression system. Mol Ther. Dec. 2005;12(6):1217-25. doi: 10.1016/j.ymthe.2005.08.018. Epub Oct. 6, 2005.
Kondratov et al., 549. Fine Tuning of Transduction Efficiency or rAAV Vectors via Modulation of Capsid Composition. Mol. Ther. May 1, 2016;24(Supplemental 1):S220.
Lecomte et al., Advanced Characterization of DNA Molecules in rAAV Vector Preparations by Single-stranded Virus Next-generation Sequencing. Mol Ther Nucleic Acids. Oct. 27, 2015;4(10):e260. doi: 10.1038/mtna.2015.32. Supplemental Information, 25 pages.
Marsic et al., High-accuracy biodistribution analysis of adeno-associated virus variants by double barcode sequencing. Mol Ther Methods Clin Dev. Oct. 28, 2015;2:15041. doi: 10.1038/mtm.2015.41. Supplemental Information, 1 page.
Mietzsch et al., OneBac 2.0: Sf9 Cell Lines for Production of AAV5 Vectors with Enhanced Infectivity and Minimal Encapsidation of Foreign DNA. Hum Gene Ther. Oct. 2015;26(10):688-97. doi: 10.1089/hum.2015.050. Epub Aug. 6, 2015. Supplemental Information, 1 page.
Urabe et al., Insect cells as a factory to produce adeno-associated virus type 2 vectors. Hum Gene Ther. Nov. 1, 2002; 13(16):1935-43. doi: 10.1089/10430340260355347.
Urabe et al., Scalable generation of high-titer recombinant adeno-associated virus type 5 in insect cells. J Virol. Feb. 2006;80(4):1874-85. doi: 10.1128/JVI.80.4.1874-1885.2006.
Zolotukhin et al., Production and purification of serotype 1, 2, and 5 recombinant adeno-associated viral vectors. Methods. Oct. 2002;28(2):158-67. doi: 10.1016/s1046-2023(02)00220-7.

* cited by examiner

```
  1 MSFVDHPPDW LEEVGEGLRE FLGLEAGPPK PKPNQQHQDQ APGLVLPGYN
 51 YLGPGNGLDR GEPVNRADEV AREKDISYNE QLEAGDNPYL KYNHADAEFQ
101 EKLADDTSFG GNLGKAVFQA KKRVLEPFGL VEEGAKTAPT GKRIDDHFPK
151 RKKARTEEDS KPSTSSDAEA GPSGSQQLQI PAQPASSLGA DTMSAGGGGP
201 LGDNNQGADG VGNASGDWHC DSTWMGDRVV TKSTRTWVLP SYNNHQYREI
251 KSGSVDGSNA NAYFGYSTPW GYFDFNRFHS HWSPRDWQRL INNYWGFRPR
301 SLRVKIFNIQ VKEVTVQDST TTIANNLTST VQVFTDDDYQ LPYVVGNGTE
351 GCLPAFPPQV FTLPQYGYAT LNRDNTENPT ERSSFFCLEY FPSKMLRTGN
401 NFEFTYNFEE VPFHSSFAPS QNLFKLANPL VDQYLYRFVS TNNTGGVQFN
451 KNLAGRYANT YKNWFPGPMG RTQGWNLGSG VNRASVSAFA TTNRMELEGA
501 SYQVPPQPNG MTNNLQGSNT YALENTMIFN SQPANPGTTA TYLEGNMLIT
551 SESETQPVNR VAYNVGGQMA TNNQSSTTAP ATGTYNLQEI VPGSVWMERD
601 VYLQGPIWAK IPETGAHFHP SPAMGGFGLK HPPPMMLIKN TPVPGNITSF
651 SDVPVSSFIT QYSTGQVTVE MEWELKKENS KRWNPEIQYT NNYNDPQFVD
701 FAPDSTGEYR TTRPIGTRYL TRPL
```

| Tryptic peptide sequence | m/z |
|---|---|
| LANPLVDQYLYR | 1464.78 |
| TWVLPSYNNHQYR | 1677.81 |
| IPETGAHFHPSPAMGGFGLK | 2051.02 |

FIG. 5A

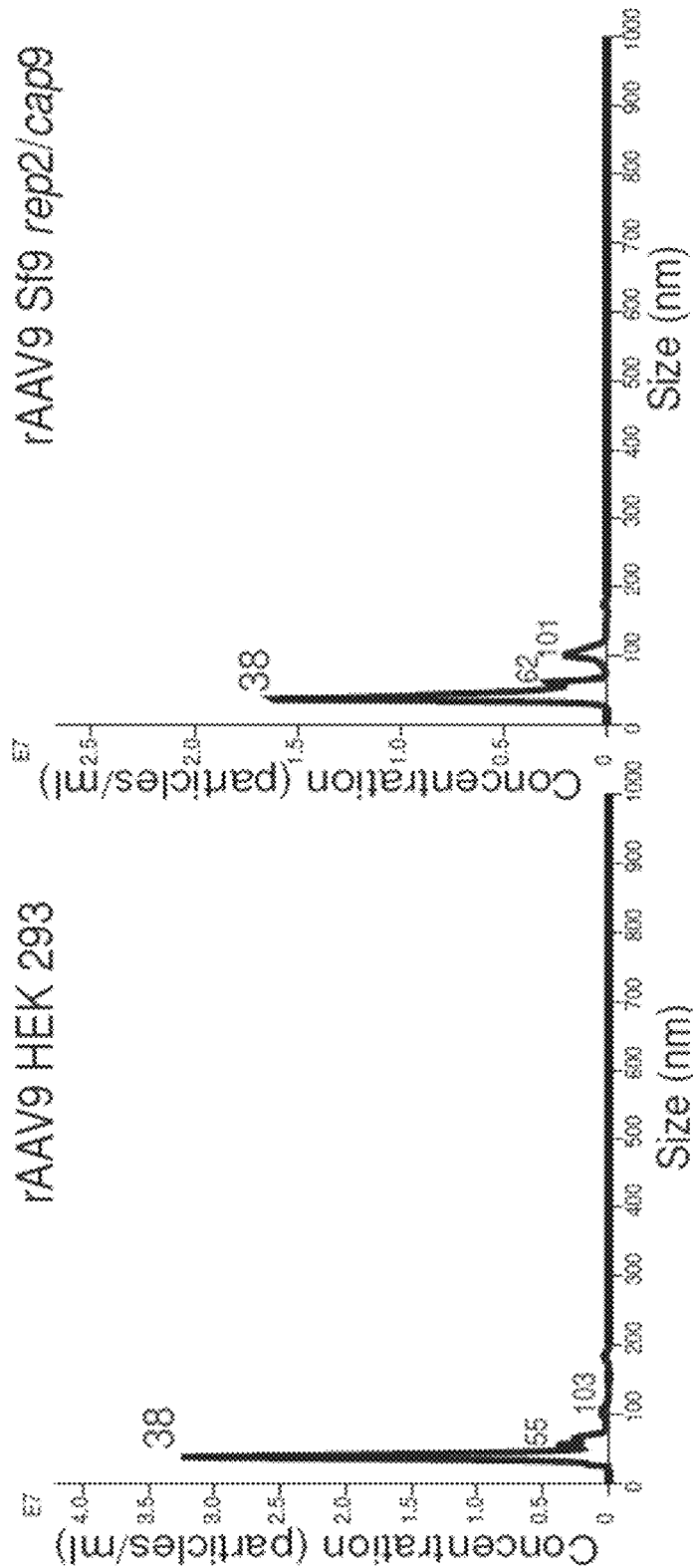

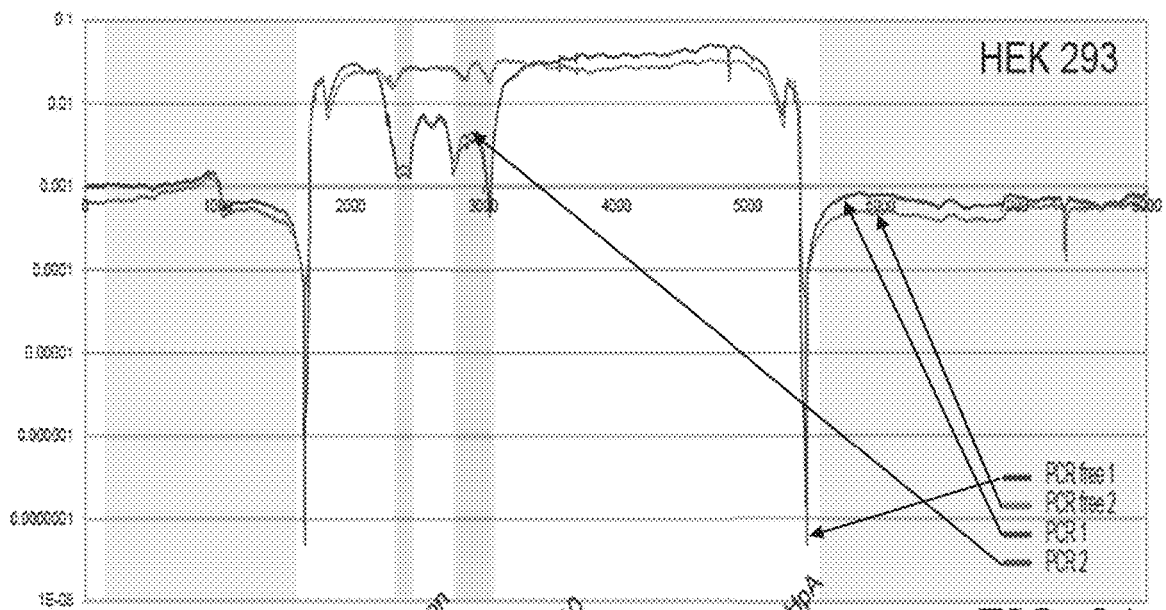
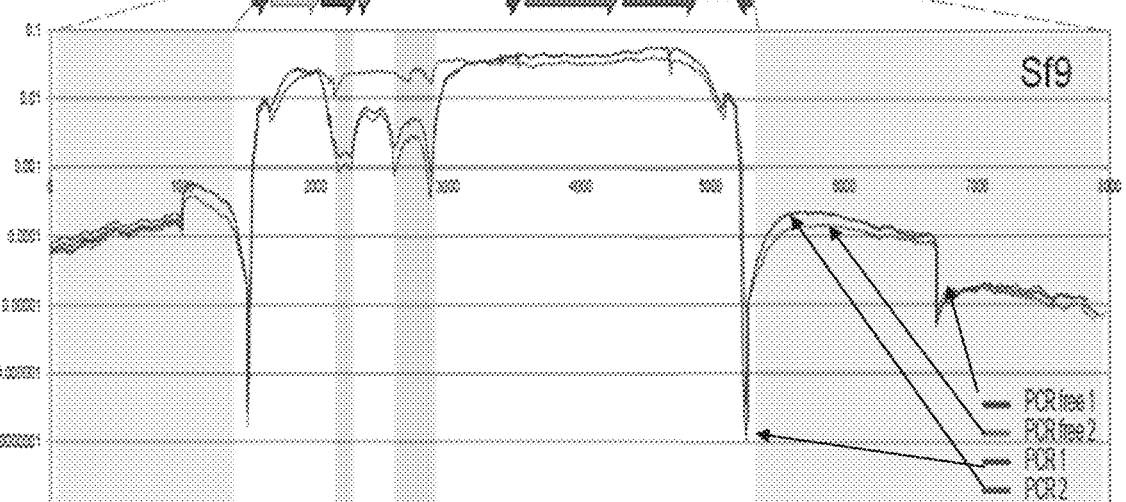
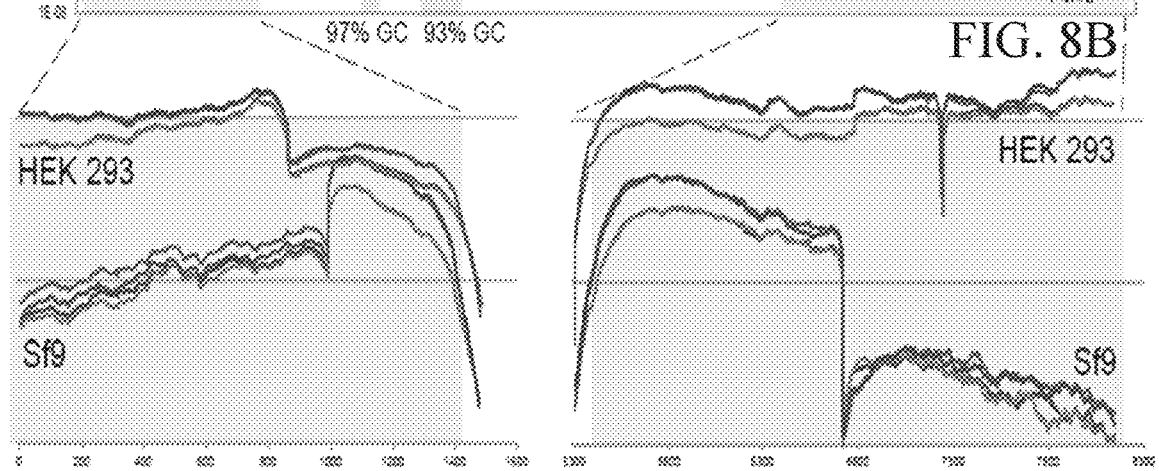
FIG. 8A
FIG. 8B
FIG. 8C
FIG. 8D

Transduction efficiency of rAAV3 generated in HEK 293 cells and Sf9 cells (rAAV3 MOI 5000, Ad5 co-infection, HUH7 cells)

METHODS OF ENHANCING BIOLOGICAL POTENCY OF BACULOVIRUS SYSTEM-PRODUCED RECOMBINANT ADENO-ASSOCIATED VIRUS

RELATED APPLICATIONS

This application claims the benefit under 35 U.S.C. § 119(e) of U.S. Provisional Application No. 62/747,481, filed Oct. 18, 2018, entitled "METHODS OF ENHANCING BIOLOGICAL POTENCY OF BACULOVIRUS SYSTEM-PRODUCED RECOMBINANT ADENO-ASSOCIATED VIRUS" the entire contents of which are incorporated herein by reference.

GOVERNMENT SUPPORT

This invention was made with government support under R01 HL097088 awarded by the National Institutes of Health. The government has certain rights in the invention.

BACKGROUND

Adeno-associated virus (AAV) has emerged as one of the most promising viral vectors for human gene therapy. Recombinant adeno-associated virus (rAAV) is being evaluated in gene therapy clinical trials for hemophilia B, malignant melanoma, cystic fibrosis, and other diseases. While large scale production of rAAV using mammalian cell culture systems has been historically problematic, AAV production systems using insect cells have been shown to be a viable alternative. However, the different cellular environment has provided challenges with regard to viral particle assembly of some AAV serotypes.

SUMMARY OF THE INVENTION

Provided herein are compositions and methods related to the production of rAAV in host producer cells (e.g., in insect cells). The biological potency (e.g., infectivity) of rAAV particles partly depends on the virion capsid composition, for example, the stoichiometric ratios of the capsid proteins VP1, VP2, and VP3. Some rAAV serotypes (e.g., AAV5, AAV8, AAV9, AAV3 and AAV6) manufactured in a heterologous system such as insect cells (e.g., Sf9 cells) are characterized by abnormal VP1 expression levels. Upon viral assembly, the abnormal VP1 expression results in the production of viral particles comprised of improper capsid protein ratios, which hinders the ability of the particles to efficiently transduce cells. Methods of obtaining useful stoichiometric ratios of capsid proteins are complicated by results indicating that an overabundance of VP1 can impair the insect cell's ability to efficiently package the viral particle while low levels of VP1 can result in particles with inefficient transduction. Thus, with respect to insect cell rAAV production systems, it remains a challenge using current techniques to produce increased amounts of infective particles without negatively impacting particle assembly.

Methods and compositions described herein provide recombinant VP1 genes comprising a modified Kozak sequence associated with the VP1 translation initiation site. Recombinant VP1 genes described in this application are useful to produce infective rAAV particles comprising a gene of interest (e.g., for subsequent research and/or therapeutic uses). In some embodiments, recombinant VP1 genes described in this application can be used to produce rAAV particles of one or more serotypes in insect cells. In some embodiments, methods and compositions described in this application can be used to screen and identify recombinant VP1 genes of one or more serotypes that are useful to produce rAAV particles of one or more serotypes in insect cells and/or in other producer cells of interest (e.g., in mammalian cells). In some embodiments, one or more recombinant VP1 genes can be useful to produce stable and/or infective rAAV particles that contain recombinant genomes of interest at relatively high frequencies and/or with relatively low rates of mis-packaged nucleic acids.

In some aspects, the disclosure provides compositions and methods useful in the production of rAAV derived from an AAV5 serotype. In some aspects, the disclosure provides compositions and methods useful in the production of rAAV derived from an AAV8 serotype. In yet other aspects, the disclosure provides compositions and methods useful in the production of rAAV derived from an AAV9 serotype.

In some aspects, the disclosure provides a nucleic acid comprising a nucleotide sequence encoding a modified Kozak sequence and AAV VP1, VP2, and VP3 capsid proteins, wherein the modified Kozak sequence is selected from SEQ ID NOs: 2-11 (Table 1). In some embodiments, the modified Kozak sequence is SEQ ID NO: 8 or SEQ ID NO: 9. In some embodiments, the VP1, VP2, and VP3 capsid proteins are derived from an AAV5 serotype. In some embodiments, the VP1, VP2, and/or VP3 capsid proteins are variant AAV5 capsid proteins (e.g., they are encoded by a sequence containing one or more mutations and that encodes a capsid protein having one or more amino acid substitutions relative to a corresponding wild-type capsid protein).

In some embodiments, the nucleic acid further comprises a promoter sequence. In some embodiments, the promoter sequence is a polyhedrin (polh) promoter sequence. In some embodiments, the modified Kozak sequence contains an initiation codon for translation of the VP1 capsid protein. In some embodiments, the initiation codon for translation of the VP1 capsid protein is AUG. In some embodiments, the nucleic acid is packaged in a viral particle (e.g., a baculovirus particle). In some embodiments, the disclosure provides an insect cell comprising the nucleic acid.

In some aspects, the disclosure relates to a method of producing rAAV in an insect cell, wherein the rAAV is derived from an AAV5 serotype, the method comprising (a) transfecting an insect cell with: (i) a baculovirus comprising a nucleic acid comprising a nucleotide sequence encoding a modified Kozak sequence and AAV5 VP1, VP2, and VP3 capsid proteins, wherein the modified Kozak sequence is selected from SEQ ID NOs: 2-11, (ii) a baculovirus comprising a nucleotide sequence encoding an AAV Rep protein, (iii) a baculovirus comprising two AAV inverted terminal repeat (ITR) nucleotide sequences flanking a gene of interest operably linked to a promoter sequence; (b) culturing the insect cell under conditions suitable to produce rAAV; and (c) recovering the rAAV from the insect cell. In some embodiments, the insect cell is an Sf9 cell.

In some aspects, the disclosure provides a nucleic acid comprising a nucleotide sequence encoding a modified Kozak sequence and AAV VP1, VP2, and VP3 capsid proteins, wherein the modified Kozak sequence is selected from SEQ ID NOs: 13-32 (Table 2). In some embodiments, the modified Kozak sequence is SEQ ID NO: 25, SEQ ID NO: 26, SEQ ID NO: 27, SEQ ID NO: 28, SEQ ID NO: 29, SEQ ID NO: 30, SEQ ID NO: 31, or SEQ ID NO: 32. In some embodiments, the VP1, VP2, and VP3 capsid proteins are derived from an AAV8 serotype. In some embodiments, the VP1, VP2, and/or VP3 capsid proteins are variant AAV8 capsid proteins (e.g., they are encoded by a sequence containing one or more mutations and that encodes a capsid protein having one or more amino acid substitutions relative to a corresponding wild-type capsid protein).

In some embodiments, the nucleic acid further comprises a promoter sequence. In some embodiments, the promoter sequence is a polyhedrin (polh) promoter sequence. In some embodiments, the modified Kozak sequence contains an initiation codon for translation of the VP1 capsid protein. In some embodiments, the initiation codon for translation of the VP1 capsid protein is AUG. In some embodiments, the nucleic acid is packaged in a viral particle (e.g., a baculovirus particle). In some embodiments, the disclosure provides an insect cell comprising the nucleic acid.

In some aspects, the disclosure relates to a method of producing rAAV in an insect cell, wherein the rAAV is derived from an AAV8 serotype, the method comprising (a) transfecting an insect cell with: (i) a baculovirus comprising a nucleic acid comprising a nucleotide sequence encoding a modified Kozak sequence and AAV8 VP1, VP2, and VP3 capsid proteins, wherein the modified Kozak sequence is selected from SEQ ID NO: 13-32, (ii) a baculovirus comprising a nucleotide sequence encoding an AAV Rep protein, (iii) a baculovirus comprising two AAV ITR nucleotide sequences flanking a gene of interest operably linked to a promoter sequence; (b) culturing the insect cell under conditions suitable to produce rAAV; and (c) recovering the rAAV from the insect cell. In some embodiments, the insect cell is an Sf9 cell.

In some aspects, the disclosure provides a nucleic acid comprising a nucleotide sequence encoding a modified Kozak sequence and AAV VP1, VP2, and VP3 capsid proteins, wherein the modified Kozak sequence is selected from SEQ ID NO: 34-45 (Table 3). In some embodiments, the modified Kozak sequence is SEQ ID NO: 35, SEQ ID NO: 36, SEQ ID NO: 38, or SEQ ID NO: 42. In some embodiments, the VP1, VP2, and VP3 capsid proteins are derived from an AAV9 serotype. In some embodiments, the VP1, VP2, and/or VP3 capsid proteins are variant AAV9 capsid proteins (e.g., they are encoded by a sequence containing one or more mutations and that encodes a capsid protein having one or more amino acid substitutions relative to a corresponding wild-type capsid protein).

In some aspects, the disclosure provides a nucleic acid comprising a nucleotide sequence encoding a modified Kozak sequence and AAV VP1, VP2, and VP3 capsid proteins, wherein the modified Kozak sequence is selected from SEQ ID NO: 46-55 (Table 4). In some embodiments, the modified Kozak sequence is SEQ ID NO: 49. In some embodiments, the VP1, VP2, and VP3 capsid proteins are derived from an AAV3 serotype. In some embodiments, the VP1, VP2, and/or VP3 capsid proteins are variant AAV3 capsid proteins (e.g., they are encoded by a sequence containing one or more mutations and that encodes a capsid protein having one or more amino acid substitutions relative to a corresponding wild-type capsid protein).

In some aspects, the disclosure provides a nucleic acid comprising a nucleotide sequence encoding a modified Kozak sequence and AAV VP1, VP2, and VP3 capsid proteins, wherein the modified Kozak sequence is selected from SEQ ID NO: 56-67 (Table 5). In some embodiments, the VP1, VP2, and VP3 capsid proteins are derived from an AAV6 serotype. In some embodiments, the VP1, VP2, and/or VP3 capsid proteins are variant AAV6 capsid proteins (e.g., they are encoded by a sequence containing one or more mutations and that encodes a capsid protein having one or more amino acid substitutions relative to a corresponding wild-type capsid protein).

In some embodiments, the nucleic acid further comprises a promoter sequence. In some embodiments, the promoter sequence is a polyhedrin (polh) promoter sequence. In some embodiments, the modified Kozak sequence contains an initiation codon for translation of the VP1 capsid protein. In some embodiments, the initiation codon for translation of the VP1 capsid protein is AUG. In some embodiments, the nucleic acid is packaged in a viral particle (e.g., a baculovirus particle). In some embodiments, the disclosure provides an insect cell comprising the nucleic acid.

In some aspects, the disclosure relates to a method of producing rAAV in an insect cell, wherein the rAAV is derived from an AAV9 serotype, the method comprising (a) transfecting an insect cell with: (i) a baculovirus comprising a nucleic acid comprising a nucleotide sequence encoding a modified Kozak sequence and AAV9 VP1, VP2, and VP3 capsid proteins, wherein the modified Kozak sequence is selected from SEQ ID NO: 34-45, (ii) a baculovirus comprising a nucleotide sequence encoding an AAV Rep protein, (iii) a baculovirus comprising two AAV ITR nucleotide sequences flanking a gene of interest operably linked to a promoter sequence; (b) culturing the insect cell under conditions suitable to produce rAAV; and (c) recovering the rAAV from the insect cell. In some embodiments, the insect cell is an Sf9 cell.

In some aspects, the disclosure relates to a method of producing rAAV in an insect cell, wherein the rAAV is derived from an AAV3 serotype, the method comprising (a) transfecting an insect cell with: (i) a baculovirus comprising a nucleic acid comprising a nucleotide sequence encoding a modified Kozak sequence and AAV3 VP1, VP2, and VP3 capsid proteins, wherein the modified Kozak sequence is selected from SEQ ID NO: 46-55, (ii) a baculovirus comprising a nucleotide sequence encoding an AAV Rep protein, (iii) a baculovirus comprising two AAV ITR nucleotide sequences flanking a gene of interest operably linked to a promoter sequence; (b) culturing the insect cell under conditions suitable to produce rAAV; and (c) recovering the rAAV from the insect cell. In some embodiments, the modified Kozak sequence is SEQ ID NO: 49. In some embodiments, the insect cell is an Sf9 cell.

In some aspects, the disclosure relates to a method of producing rAAV in an insect cell, wherein the rAAV is derived from an AAV6 serotype, the method comprising (a) transfecting an insect cell with: (i) a baculovirus comprising a nucleic acid comprising a nucleotide sequence encoding a modified Kozak sequence and AAV6 VP1, VP2, and VP3 capsid proteins, wherein the modified Kozak sequence is selected from SEQ ID NO: 56-67, (ii) a baculovirus comprising a nucleotide sequence encoding an AAV Rep protein, (iii) a baculovirus comprising two AAV ITR nucleotide sequences flanking a gene of interest operably linked to a promoter sequence; (b) culturing the insect cell under conditions suitable to produce rAAV; and (c) recovering the rAAV from the insect cell. In some embodiments, the insect cell is an Sf9 cell.

In some aspects, this application provides a library of nucleic acids comprising a nucleotide sequence encoding a modified Kozak sequence comprising the initiation codon for translation of an AAV VP1 capsid protein and nucleotide sequence variations in 1-6 nucleotides immediately upstream of the VP1 translation initiation codon and/or nucleotide sequence variations in 1-2 nucleotides immediately downstream of the VP1 translation initiation codon. In some embodiments, the nucleic acid comprises XXXXXX (ATG), wherein (ATG) is the VP1 initiation codon. In some embodiments, the nucleic acid comprises XXXXXX(AUG), wherein (AUG) is the VP1 initiation codon. In some embodiments, X represents any nucleotide, e.g., any nucleotide that is different from a naturally occurring nucleotide at that position in a wild-type VP1 gene for an AAV serotype of interest.

These and other aspects are described in more detail in the following description and accompanying examples and figures.

BRIEF DESCRIPTION OF THE DRAWINGS

The following drawings form part of the present specification and are included to further demonstrate certain aspects of the present disclosure, which can be better understood by reference to one or more of these drawings in combination with the detailed description of specific embodiments presented herein.

FIG. 4A illustrates a non-limiting example of a design of rep and cap genes expression cassettes. FIG. 4B shows an example of a direct correlation of rAAV5 VP1 protein expression and its relative VP1 Kozak translation initiation site (TIS) efficiency: Western blotting analysis of capsid proteins isolated from ten separate cell lines incorporating stably integrated cap expression cassettes. The relative TIS efficiencies (%) for each capsid VP1 gene construct are shown below the respective lane. FIG. 4C shows examples of capsid protein compositions of rAAV5 purified from HEK 293 and Sf9 cells: SDS-protein gel analysis of double iodixanol-purified rAAV5-GFP, directly visualized with shortwave UV photoactivation (stain-free technology, Bio-Rad). (*) denotes a slower migrating band often observed in rAAV5 samples purified from HEK 293 cells, and which was excluded from VP2 quantification analysis. FIG. 4D shows examples of capsid protein compositions of rAAV9 purified from HEK 293 and Sf9 cells. Analysis is the same as in panel FIG. 4C.

FIGS. 5A-5D depict MALDI-TOF analysis of the AAV5 VP1, VP2, and VP3 capsid proteins stoichiometry. FIG. 5A shows an amino acid sequence (SEQ ID NO: 77) of the AAV5 capsid with VP1 unique N-termini marked by a dashed line, unique VP2—marked by a dot-dashed line, and common VP3 C-termini—marked by a black line. The downward arrows indicate the respective proteins. Tryptic peptides selected for MS analysis are underlined and shown below next to their respective observed masses. The tryptic peptides correspond to SEQ ID NOs: 78, 60, and 79, from top to bottom. FIG. 5B shows a MALDI-TOF-MS spectrum of all tryptic peptides of rAAV5 digested in $H_2^{18}O$. The circled peptide is one representative out of three analyzed. FIG. 5C shows two overlaid MALDI-TOF MS spectra of the same tryptic peptide TWVLPSYNNHQYR (SEQ ID NO: 60) originating from the VP1 gel band digested with trypsin prepared in $^{16}O$ water, or from the VP3 gel band digested with trypsin prepared in $^{18}O$ water. $^{18}O$ water incorporates two $^{18}O$ atoms on the C-terminus of the peptide thus shifting the mass by 4 atomic mass units (amu). These digestion products were spotted/analyzed separately and the spectra overlaid to show the complete incorporation of two $^{18}O$ into the VP3 peptide. FIG. 5D shows isotopic "fingers" of the same peptide derived from VP1 or VP3 after the digestion products were mixed at 1:1 ratios to calculate the relative content.

FIGS. 6A-6F depict Nanoparticle Tracking Analysis of sizes and titers of rAAV9 (FIGS. 6A-C), or rAAV5 (FIGS. 6D-F) manufactured in HEK 293 cells (FIGS. 6A, 6D), or Sf9 cells (FIGS. 6B, 6E). FIGS. 6A, 6B, 6C, and 6D show a graphic representation of Finite Track Length Adjustment (FTLA) algorithm, an average of three independent video captures of rAAV/nano-gold particle complexes, each recorded for 30 sec for each sample. FIGS. 6C and 6F show the calculated ratios of full/total particles for each preparation. The numbers next to the peaks show the calculated rAAV/nano-gold particle complexes sizes. The smaller peaks of larger diameters represent aggregated dimers, and trimers of rAAV particles. FIGS. 6C and 6F display calculated ratios of DNA-containing vs. total number of AAV particles in the respective viral stocks.

FIG. 7A provides heat map images that show bioluminescence (BLI) signal detected 3 weeks after AAV injections. The pseudo-color scale represents the intensity of light emitted in number of counts. Max and Min are the maximum and the minimum number of counts, respectively. FIG. 7B provides a graph that shows the BLI intensity expressed as the total number of counts, as mean±SEM (n=4 per group). Mann-Whitney test analysis show a significant difference between groups (p=0.0286, one-tailed test). FIG. 7C shows mApple fluorescence in the coronal brain sections as detected by a variable mode laser scanner (black-and-white, B/W images), or fluorescence microscope (shaded image).

FIGS. 8A-8D depict the distribution of the NGS reads of the rAAV-Bac-UF26 cassette and its immediate junctions. FIG. 8A shows Illumina read coverage of rAAV5-Bac-UF26 cassette packaged in HEK 293 cells numerically normalized by dividing the number of reads at each nucleotide position by the total number of reads of the referenced sequence. Sequence coverage graphs for duplicate samples are indicated with arrows for PCR-free (PCR-free 1 and PCR-free 2) and PCR-based (PCR 1 and PCR 2). The drop of coverage between rAAV cassette and the adjacent sequences reflects a graphic representation of the bioinformatics analysis limitations rather than actual reduction in sequence coverage. Shown below the graph is an annotated map of referenced rAAV-Bac-UF26 cassette drawn to the scale of the sequences in the panels (FIG. 8A) and (FIG. 8B). Sequences immediately adjacent to the rAAV cassette in the bacterial plasmid DNA are shaded in a lighter gray tint. FIG. 8B shows Illumina-read coverage of rAAV5-Bac-UF26 cassette packaged in Sf9 B8 cells. GC-enriched sequences within rAAV cassette are shaded in a darker gray tint. FIG. 8C illustrates a zoom from panels in FIG. 8A and FIG. 8B of the sequences immediately adjacent to the left rAAV ITR in both HEK 293 and Sf9 B8 cells. FIG. 8D illustrates a zoom from panels in FIG. 8A and FIG. 8B of the sequences immediately adjacent to the right AAV ITR in both HEK 293 and Sf9 B8 cells.

Sf9 B8 cells. FIGS. 9A-9B show substitutions of four residues A, G, C, and T are plotted cumulatively if read in a given position relative to the reference pTR-Bac-UF26 database sequence. Relative SNPs ratios (Y axes) were defined as a proportion of total number of reads in a given position with a substitution to the total depth of sequencing in the same position. Depth of sequencing is a sum of sequence reads of a reference and alternative nucleotide in a given position excluding insertion/deletions (indels). Analysis of SNP variants included positive control, plasmid pTR-Bac-UF26 sample. Consequently, a zero rate of SNP represents a residue identical with the database reference, and a positive value signifies a newly acquired SNP relatively to the parent plasmid database sequence. Regions of high GC-content are shaded. FIG. 9C shows an annotated map of a referenced rAAV-Bac-UF26 cassette drawn to the scale of the sequence in FIGS. 9A-9B.

FIG. 12A shows fluorescence-activated cell sorting (FACS) and its graphic quantification of rAAV5-UF50-BC. FIG. 12B shows fluorescence-activated cell sorting (FACS) and its graphic quantification of rAAV9-UF50-BC.

FIG. 14A shows PCR-free libraries sequenced directly by NGS: 1,2—rAAV5/Sf9; 3,4—rAAV5/HEK 293. FIG. 14B shows PCR-free libraries used for low cycle PCR enrichment: 5,6—rAAV5/Sf9, 7,8—rAAV5/HEK293. FIG. 14C shows PCR enriched libraries: 9, 10—rAAV5/Sf9; 11, 12—rAAV5/HEK 293. Libraries 9-12 were sequenced directly by NGS.

DETAILED DESCRIPTION

Figure 1:
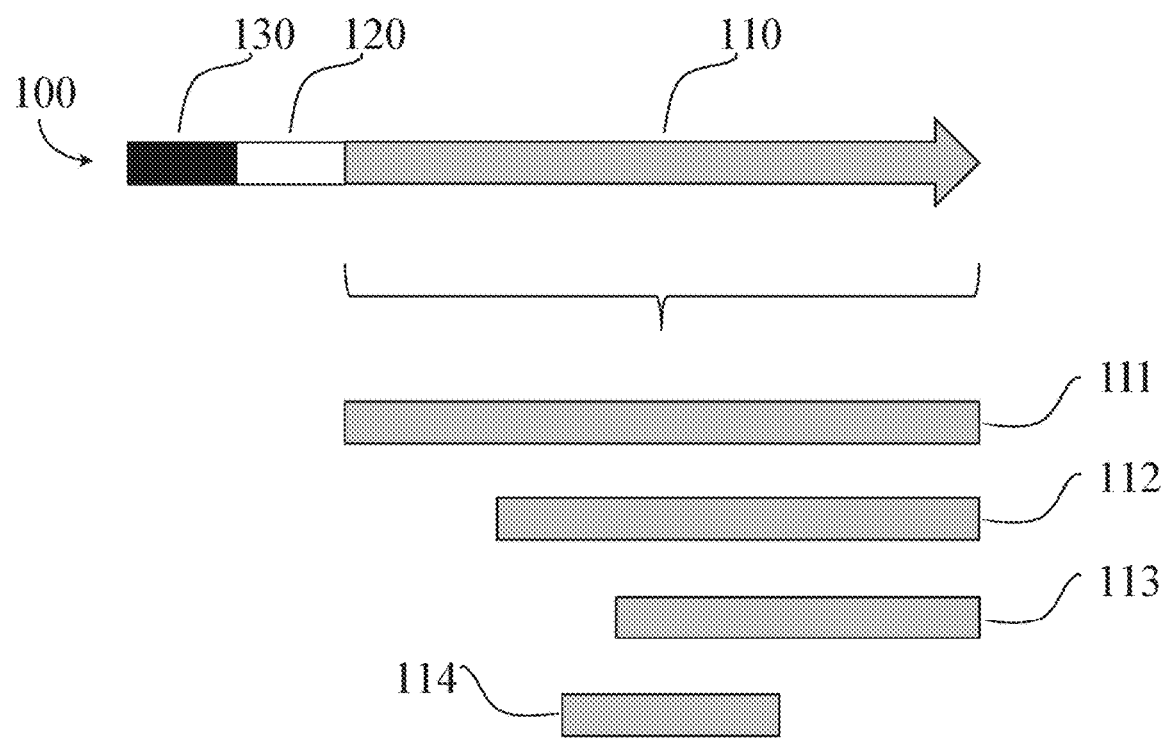
FIG. 1 illustrates a non-limiting design of a capsid helper nucleotide encoding VP1, VP2, and VP3, and the encoded capsid proteins.

Aspects of the application provide methods and compositions for producing rAAV particles in host producer cells (e.g., in insect producer cells). In some embodiments, modified translation initiation sequences (TIS, also referred to as Kozak sequences) are associated with a VP1 start codon (e.g., an ATG/AUG start codon for a recombinant gene encoding the VP1 capsid protein) and are incorporated into a recombinant nucleic acid that encodes the VP1, VP2, and VP3 capsid proteins of an AAV serotype of interest. In some embodiments, methods and compositions described in this application can be used to identify VP1 Kozak sequences that are useful to produce effective rAAV particles in host producer cells (e.g., rAAV particles that are produced with a high yield, that are infective, DNA containing, stable, etc., or any combination thereof). In some embodiments, rAAV particles produced using methods and compositions described in this application can contain a gene of interest (e.g., a therapeutic gene) and can be used for therapeutic purposes.

rAAV is extensively used as a vector for gene therapy/DNA vaccine delivery, but large-scale production of infectious rAAVs for clinical applications remains challenging based on current technology. An AAV capsid consists of three capsid proteins, VP1, VP2, and VP3, derived via alternative splicing and differential codon usage of a single capsid gene in AAV genome. The VP3 sequence is common between all three splice variants, and VP2 and VP1 have longer N-terminal sequences with VP1 being the longest capsid protein (as illustrated for example in FIG. 1). The ratio of VP1/VP2/VP3 in a typical capsid particle is estimated to be 1/1/10. Moreover, it appears that there is no defined VP1/VP2/VP3 stoichiometry and that the assembly is stochastic such that the relative amount of VP1/VP2/VP3 that is incorporated in the capsid depends mainly on their relative expression levels in a host producer cell (or in an in vitro production system). Compositions and methods described in this application provide recombinant capsid genes having modified VP1 Kozak sequences (e.g., surrounding an ATG/AUG translation initiation codon) that are translated into VP1, VP2, and VP3 capsid proteins in producer cells in relative amounts that are useful to produce infective rAAV particles containing recombinant genes of interest. In some embodiments, a recombinant capsid gene does not have appropriate splice donor and/or acceptor sites to allow for natural splicing of the capsid gene (e.g., in some embodiments transcripts from the recombinant capsid gene are not spliced appropriately or at all in the producer cells). In some embodiments, to increase leaky ribosome scanning and produce a desired ratio of VP1/VP2/VP3 from a capsid gene, a canonical AUG codon associated with an attenuated Kozak sequence was used for the VP1 translation start site. rAAV particles produced from a modified capsid gene and encapsidating a gene of interest can be used for research, clinical testing, and therapeutic purposes. In some embodiments, modified capsid genes described in this application can be used for large scale manufacturing of rAAV particles.

In some aspects, the application also provides methods and compositions for screening and evaluating AAV capsid gene expression constructs to identify sequences that are useful for producing infective rAAV particles. In some embodiments, a plurality of different rAAV capsid gene expression constructs are evaluated for rAAV particle assembly in a host cell of interest. In some embodiments, the different rAAV capsid gene expression constructs comprise the same promoter, the same AAV capsid coding sequence (e.g., encoding VP1, VP2, and VP3 capsid proteins of any serotype of interest, optionally including one or more capsid mutations) but have different Kozak sequences associated with the translation initiation codon for VP1 (e.g., ATG/AUG). In general, the translation codons and surrounding initiation sequences for VP2 and VP3 are not changed (e.g., they are kept as their natural wild-type sequences). However, in some embodiments, one or more changes could be made in these sequences. In some embodiments, the different Kozak sequences represent sequence variations within the six nucleotides immediately upstream of the translation initiation codon for VP1. In some embodiments, the different Kozak sequences include sequence variations within the two nucleotides immediately downstream from the translation initiation codon for VP1. Accordingly, in some embodiments, the different Kozak sequences are selected from a library of different Kozak sequences that represent nucleotide sequence variations at one or more positions (e.g., 1, 2, 3, 4, 5, or 6 of the positions) within the six nucleotides immediately upstream of the translation initiation codon for VP1 and/or one or more positions (e.g., 1 or 2 of the positions) within the two nucleotides immediately downstream from the translation initiation codon for VP1. In some embodiments, the different Kozak sequences can represent all or a subset of all possible variations of the Kozak sequence for VP1. In some embodiments, the variations are relative to a natural VP1 Kozak sequence for the AAV capsid serotype (e.g., serotype 1, 2, 3, 3B, 4, 5, 6, 7, 8, 9, 10, 11, 12, etc.) gene that is being modified. In some embodiments, different Kozak sequences having a selected percentage translation efficiency (e.g., relative to a reference translation efficiency, for example relative to a translation efficiency associated with a natural or consensus Kozak sequence) are evaluated. In some embodiments, the different Kozak sequences represent translation efficiency ranges between 25% and 50%, for example between 25% and 45%, for example between 30% and 40%, around 25%, around 30%, around 35%, around 40%, around 45%, around 50%, or other values (e.g., intermediate values between any of the foregoing). In some embodiments, all Kozak sequences having a desired translation efficiency or range of translation efficiencies are evaluated. In some embodiments, a subset of Kozak sequences having a translation efficiency within the a desired percent range are evaluated. In some embodiments, Kozak sequences representing percentage increments (e.g., 1-5% increments, for example around 1%, 2%, 3%, 4%, or 5% increments) within a target range of translation efficiencies are evaluated. In some embodiments, the different Kozak sequences are evaluated by introducing recombinant nucleic acids each containing the recombinant capsid gene having a different Kozak sequence (e.g., associated with the VP1 start codon) into host cells that also express other helper genes (e.g., Rep, and other helper genes) and that also contain a recombinant AAV genome of interest having a target gene of interest (e.g., a control gene for example encoding a detectable marker or a therapeutic gene of interest) flanked by ITR sequences (so that the gene of interest flanked by the ITR sequences can be packaged into rAAV particles containing the capsid proteins expressed from the recombinant capsid gene). The host cells can be cells of any type (e.g., mammalian, insect, or other types of host cells). The host cells can express the other helper genes and/or the contain the rAAV genome of interest as a result of plasmid transfection (e.g., using one or more plasmids that express the other helper genes and/or that contain the rAAV genome of interest), viral transduction (e.g., using one or more recombinant viruses, for example a recombinant baculovirus, adenovirus, herpes virus, or other recombinant virus, having recombinant viral genomes that express the other helper genes and/or that contain the rAAV genome of interest), or genomic integration (e.g., with one or more helper genes and/or the rAAV genome of interest). After the different capsid gene constructs are introduced into the host cells, the cells are incubated under conditions to produce rAAV particles, and the rAAV particles are isolated and/or purified, and evaluated. The isolated and/or purified rAAV particles can be evaluated based on one or more factors, including but not limited to one or more of the following:

a) The yield of rAAV particles. In some embodiments, a similar or better yield than for a reference rAAV, for example of the same serotype (e.g., produced using a reference methodology, for example in HEK 293 cells, or Sf9 cells) is selected.

b) The ratio of VP1/VP2/VP3 proteins in the rAAV particles. In some embodiments, a ratio of VP1/VP2/VP3 of >0.5/>0.5/10 is selected. Accordingly, in some embodiments, the ratio of VP1/VP3 is around or >0.5/10, for example around or >0.75/10, for example around or >1/10, for example around or >1.25/10, for example around or >1.5/10, for example around or >1.75/10, or around 2/10, or any intermediate ratio. Similarly, in some embodiments, the ratio of VP2/VP3 is independently around or >0.5/10, for example around or >0.75/10, for example around or >1/10, for example around or >1.25/10, for example around or >1.5/10, for example around or >1.75/10, or around 2/10, or any intermediate ratio.

c) The ratio of full/empty rAAV particles. In some embodiments, a ratio of full/empty particles that is similar or greater than a reference ratio (e.g., the ratio of full/empty for rAAV particles, for example of the same serotype, produced using a reference methodology, for example in HEK 293 cells, or Sf9 cells) is selected.

d) The transduction efficiency of the rAAV particles. In some embodiments, a similar or better transduction efficiency than for a reference rAAV, for example of the same serotype (e.g., produced using a reference methodology, for example in HEK 293 cells, or Sf9 cells) is selected. In some embodiments, the transduction efficiency is evaluated in vitro (e.g., in cells, for example HeLa cells, grown in culture). In some embodiments, the transduction efficiency is evaluated in vivo (e.g., in an animal model, for example a rodent model, such as a mouse model).

e) The precision of DNA packaging in the rAAV particles. In some embodiments, a similar or higher precision of DNA packaging (e.g., of rAAV genomic DNA relative to other DNA, for example host DNA, or DNA flanking the rAAV genome on a plasmid or virus vector in a host cell) than for a reference rAAV is selected. In some embodiments, the reference rAAV can be an rAAV, for example of the same serotype, that is produced using a reference methodology, for example in HEK 293 cells, or Sf9 cells. In some embodiments, the precision of DNA packaging can be evaluated by determining the percentage of non-rAAV genome that is packaged. This can be determined using any suitable method, for example by sequencing the packaged DNA in rAAV particles (e.g., using NGS or other techniques).

As a result of this evaluation, one or more Kozak sequences (and/or Cap expression constructs including the Kozak sequences upstream of the VP1 translation initiation codon) can be selected and used for producing rAAV of interest in a particular cell type.

Accordingly, aspects of the application relate to methods and compositions useful in the production of rAAV in insect cells. In some aspects, the disclosure provides nucleic acid compositions comprising a nucleotide sequence encoding i) a modified Kozak sequence and ii) AAV VP1, VP2, and VP3 capsid proteins. In some embodiments, the capsid proteins are derived from AAV5 serotype capsid proteins. In some embodiments, the capsid proteins are derived from AAV8 serotype capsid proteins. In some embodiments, the capsid proteins are derived from AAV9 serotype capsid proteins. In some embodiments, the capsid proteins are derived from AAV3 serotype capsid proteins. In some embodiments, the capsid proteins are derived from AAV6 serotype capsid proteins. In some embodiments, the nucleotide sequence further comprises a promoter sequence. In some embodiments, the promoter is operably linked to the sequence encoding the modified Kozak sequence and AAV capsid proteins.

Figure 10A:
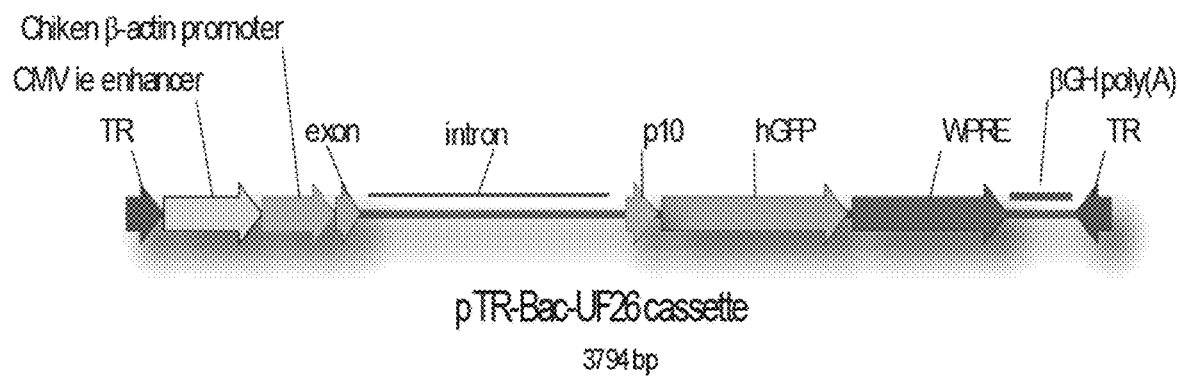
FIGS. 10A-10B depict annotated graphical maps of rAAV cassettes packaged into rAAV5 and rAAV9 capsids.
Figure 10B:
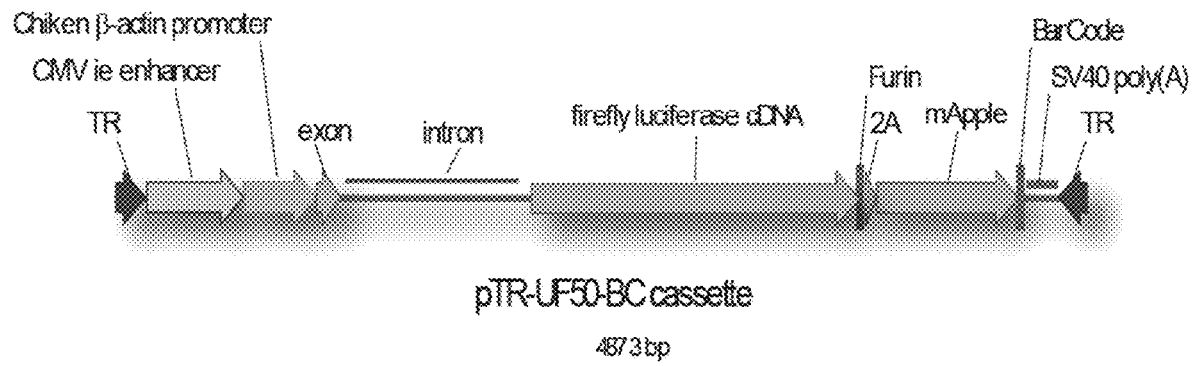

A non-limiting example of a generic structure comprising a nucleic acid provided herein is depicted in FIG. 1. A nucleic acid 100 comprises a nucleotide sequence encoding a modified Kozak sequence 120 and AAV VP1, VP2, and VP3 capsid proteins 110. In the wt AAV, in the mammalian cells, the capsid proteins are transcribed as a single mRNA that can be spliced to generate two mRNA isoforms. This post-transcriptional processing and leaky ribosome scanning allows for the production of three separate capsid proteins: AAV VP1 capsid protein 111, AAV VP2 capsid protein 112, initiated from the alternative initiation codon ACG, and AAV VP3 capsid protein 113. Additionally, in some embodiments, a separate open reading frame within the same nucleotide sequence encodes the assembly-activating protein 114. In some embodiments, a promoter sequence 130 is operably linked to the nucleotide sequence. In some embodiments, a nucleic acid comprises an enhancer. In some embodiments, the nucleotide sequence includes more than one promoter. In some embodiments, rAAV cassettes packaged into rAAV capsids resemble those found in FIGS. 10A and 10B.

A promoter is "operably linked" to a nucleotide sequence when the promoter sequence controls and/or regulates the transcription of the nucleotide sequence. In some embodiments, it is advantageous to utilize promoters that are active in insect cells. In some embodiments, the promoter is a polyhedrin (polh) promoter. In some embodiments, the promoter is selected from the group consisting of p10, p35, and IE-1. Methods and techniques for expressing foreign genes in insect host cells are known in the art. Methodology for molecular engineering and expression of polypeptides in insect cells is described, for example, in Summers and Smith. 1986. A Manual of Methods for Baculovirus Vectors and Insect Culture Procedures, Texas Agricultural Experimental Station Bull. No. 7555, College Station, Tex.; Luckow. 1991. In Prokop et al., Cloning and Expression of Heterologous Genes in Insect Cells with Baculovirus Vectors' Recombinant DNA Technology and Applications, 97-152; King, L. A. and R. D. Possee, 1992, The baculovirus expression system, Chapman and Hall, United Kingdom; O'Reilly, D. R., L. K. Miller, V. A. Luckow, 1992, Baculovirus Expression Vectors: A Laboratory Manual, New York; W.H. Freeman and Richardson, C. D., 1995, Baculovirus Expression Protocols, Methods in Molecular Biology, volume 39; U.S. Pat. No. 4,745,051; US2003148506; and WO 03/074714. However, any suitable promoter can be used (e.g., any natural, variant, synthetic, chimeric, truncated, constitutive, inducible, tissue-specific, species-specific, etc., promoter or combinations of two or more of the foregoing) depending on the cell type being used as a producer cell (e.g., insect, mammalian, or other).

In some embodiments, the modified Kozak sequence described herein contains an initiation codon for translation of the VP1 capsid protein. In some embodiments, the initiation codon is AUG. In some embodiments, the nucleic acid described herein further comprises a viral particle. In some embodiments, the nucleic acid is contained within a viral particle (e.g., encapsidated by a viral particle). In some embodiments, the viral particle is an AAV particle. In some embodiments, the viral particle is a baculovirus particle.

In some aspects, the disclosure provides methods of producing rAAV in an insect cell, comprising steps of (a) transfecting an insect cell with: (i) a baculovirus comprising a nucleic acid comprising a nucleotide sequence encoding a modified Kozak sequence and AAV VP1, VP2, and VP3 capsid proteins, wherein the modified Kozak sequence is selected from SEQ ID NO: 2-11, 13-32, 33-45, 46-55, and 56-67, (ii) a baculovirus comprising a nucleotide sequence encoding an AAV Rep protein, and (iii) a baculovirus comprising two AAV ITR nucleotide sequences flanking a gene of interest operably linked to a promoter sequence; (b) culturing the insect cell under conditions suitable to produce rAAV; and (c) recovering the rAAV from the insect cell.

In some embodiments, the disclosure provides an insect cell, wherein the insect cell comprises a nucleic acid comprising a nucleotide sequence encoding a modified Kozak sequence and AAV VP1, VP2, and VP3 capsid proteins, wherein the modified Kozak sequence is selected from SEQ ID NO: 2-11, 13-32, 33-45, 46-55, and 56-67. In some embodiments, the nucleic acid is integrated into the insect cell genome. In some embodiments, a gene encoding a Rep protein is integrated into the insect cell genome. Thus, in some embodiments, the disclosure provides a method of producing rAAV in an insect cell, comprising steps of (a) transfecting an insect cell with a baculovirus comprising two AAV ITR nucleotide sequences flanking a gene of interest operably linked to a promoter sequence, wherein the genome of the insect cell comprises a nucleotide described herein; (b) culturing the insect cell under conditions suitable to produce rAAV; and (c) recovering the rAAV from the insect cell.

The production of rAAV in insect cells has been described previously (see, for example, U.S. Patent Publication Number US20120100606, which is incorporated herein by reference in its entirety). Methods and compositions provided in the present disclosure can be utilized in any insect cell which allows for the replication of AAV and which can be maintained in culture. For example, the cell line used can be from *Spodoptera frugiperda, drosophila* cell lines, or mosquito cell lines (e.g., *Aedes albopictus* derived cell lines). In some embodiments, the insect cell is susceptible to baculovirus infection (e.g., Se301, SeIZD2109, SeUCR1, Sf9, Sf900+, Sf21, BTI-TN-5B1-4, MG-1, Tn368, HzAm1, Ha2302, and Hz2E5). Accordingly, methods and compositions provided herein are useful in producing rAAV using baculovirus expression vectors (BEVs).

BEVs have emerged as one of the most versatile systems for protein production. In addition to basic protein production, BEVs have been utilized for more complicated tasks such as the synthesis of heterologous multiprotein complexes and for the assembly of gene therapy vehicles such as rAAV. In some embodiments, the latter strategy utilizes insect cells co-infected with three BEVs, each providing a helper functionality. For example, insect cells are co-infected with a first baculovirus comprising a gene of interest flanked by AAV inverted terminal repeat (ITR) sequences, a second baculovirus comprising AAV rep, and a third baculovirus comprising AAV cap. The AAV cap encodes the assembly-activating protein (AAP) and the viral capsid proteins VP1, VP2, and VP3. The capsid proteins VP1, VP2, and VP3 are translated from the same mRNA transcript, which can be post-transcriptionally spliced into either of two differently-sized mRNA isoforms. The post-transcriptional splicing in mammalian cells occurs at a rate appropriate to generate a distribution of the mRNA forms that will result in the expression of a proper stoichiometric ratio of VP1:VP2:VP3 capsid proteins. Also, in insect cells the production of some serotypes (e.g., AAV5, AAV8, AAV9, AAV3 and AAV6) results in particles that are inefficient in transducing cells. Accordingly, compositions and methods are useful to modify VP1 expression levels to improve rAAV production in insect cells or in any other host cell types of interest (e.g., mammalian host producer cells or cells of other type).

In some aspects, the disclosure provides nucleic acid compositions comprising a nucleotide sequence encoding a modified Kozak sequence and AAV VP1, VP2, and VP3 capsid proteins, wherein the capsid proteins are derived from an AAV5 serotype. In some embodiments, the Kozak sequence comprises the initiation codon for translation of the AAV5 VP1 capsid protein and additional nucleotides upstream of the initiation codon. In some embodiments, the Kozak sequence further comprises nucleotides downstream of the initiation codon. In some embodiments, the Kozak sequence comprises a nucleotide of sequence RNXUXU(AUG)NY (SEQ ID NO: 1), wherein (AUG) is the VP1 initiation codon; R is a C or U nucleotide; N is a nucleotide selected from A, U, G, or C; X is a G or U nucleotide; and Y is a nucleotide selected from A, U, or C. In some embodiments, the Kozak sequence comprises a nucleotide sequence listed in Table 1.

TABLE 1

AAV5 VP1 Kozak Sequences

| SEQ ID NO: | Sequence |
|---|---|
| 2 | CAUUGUAUGUC |
| 3 | UCGUUUAUGGA |
| 4 | CAGUUUAUGGU |
| 5 | CAUUGUAUGGU |
| 6 | UAGUGUAUGCU |
| 7 | CAUUGUAUGCU |
| 8 | UCUUUUAUGUC |
| 9 | UGUUUUAUGUC |
| 10 | UAGUUUAUGUC |
| 11 | UAGUGUAUGUC |

In some aspects, the disclosure provides nucleic acid compositions comprising a nucleotide sequence encoding a modified Kozak sequence and AAV VP1, VP2, and VP3 capsid proteins, wherein the capsid proteins are derived from an AAV8 serotype. In some embodiments, the Kozak sequence comprises the initiation codon for translation of the AAV8 VP1 capsid protein and additional nucleotides upstream of the initiation codon. In some embodiments, the Kozak sequence further comprises nucleotides downstream of the initiation codon. In some embodiments, the Kozak sequence comprises a nucleotide of sequence YNXRNR(AUG)XZ (SEQ ID NO: 12), wherein (AUG) is the VP1 initiation codon; Y is a nucleotide selected from A, U, or C; N is a nucleotide selected from A, U, G, or C; X is a G or U nucleotide; R is a C or U nucleotide; and Z is a G or C nucleotide. In some embodiments, the Kozak sequence comprises a nucleotide sequence listed in Table 2.

TABLE 2

AAV8 VP1 Kozak Sequences

| SEQ ID NO: | Sequence |
|---|---|
| 13 | UAGCGCAUGGC |
| 14 | UGGUAUAUGGC |
| 15 | UAGUUUAUGGC |
| 16 | CAGUGUAUGGC |
| 17 | UAGUGUAUGGC |
| 18 | UAUUGUAUGGC |
| 19 | CAUUGUAUGGC |
| 20 | CCGUUUAUGGG |
| 21 | ACUUGUAUGGG |
| 22 | CAUUUUAUGGG |
| 23 | UAGUGUAUGUC |
| 24 | UAGUUUAUGUC |
| 25 | UGUUUUAUGUC |
| 26 | UCUUUUAUGUC |
| 27 | UAGUGUAUGGG |
| 28 | UAGUUUAUGGG |
| 29 | UGUUUUAUGGG |
| 30 | UCUUUUAUGGG |
| 31 | UAGUGUAUGUC |
| 32 | UAGUUUAUGUC |

In some aspects, the disclosure provides nucleic acid compositions comprising a nucleotide sequence encoding a modified Kozak sequence and AAV VP1, VP2, and VP3 capsid proteins, wherein the capsid proteins are derived from an AAV9 serotype. In some embodiments, the Kozak sequence comprises the initiation codon for translation of the AAV9 VP1 capsid protein and additional nucleotides upstream of the initiation codon. In some embodiments, the Kozak sequence further comprises nucleotides downstream of the initiation codon. In some embodiments, the Kozak sequence comprises a nucleotide of sequence UNXUXU(AUG)XZ (SEQ ID NO: 33), wherein (AUG) is the VP1 initiation codon; N is a nucleotide selected from A, U, C, or G; X is a G or U nucleotide; and Z is a G or C nucleotide. In some embodiments, the Kozak sequence comprises a nucleotide sequence listed in Table 3.

TABLE 3

AAV9 VP1 Kozak Sequences

| SEQ ID NO: | Sequence |
|---|---|
| 34 | UAGUGUAUGUC |
| 35 | UAGUUUAUGUC |
| 36 | UGUUUUAUGUC |
| 37 | UCUUUUAUGUC |

TABLE 3-continued

AAV9 VP1 Kozak Sequences

| SEQ ID NO: | Sequence |
|---|---|
| 38 | UAGUGUAUGGG |
| 39 | UAGUUUAUGGG |
| 40 | UGUUUUAUGGG |
| 41 | UCUUUUAUGGG |
| 42 | UAGUGUAUGGC |
| 43 | UAGUUUAUGGC |
| 44 | UGUUUUAUGGC |
| 45 | UCUUUUAUGGC |

In some aspects, the disclosure provides nucleic acid compositions comprising a nucleotide sequence encoding a modified Kozak sequence and AAV VP1, VP2, and VP3 capsid proteins, wherein the capsid proteins are derived from an AAV3 serotype. In some embodiments, the Kozak sequence comprises the initiation codon for translation of the AAV3 VP1 capsid protein and additional nucleotides upstream of the initiation codon. In some embodiments, the Kozak sequence further comprises nucleotides downstream of the initiation codon. In some embodiments, the Kozak sequence comprises a nucleotide of sequence GCGCAGAUCUYMXUXY(AUG)GC (SEQ ID NO: 80), wherein (AUG) is the VP1 initiation codon; N is a nucleotide selected from A, U, C, or G; M is a nucleotide selected from A, G, or C; X is a G or U nucleotide; and Y is a nucleotide selected from A, U, or C. In some embodiments, the Kozak sequence comprises a nucleotide sequence listed in Table 4.

TABLE 4

AAV3 VP1 Kozak Sequences

| SEQ ID NO: | Sequence |
|---|---|
| 46 | GCGCAGAUCUUCUUUUAUGGC |
| 47 | GCGCAGAUCUUGUUUUAUGGC |
| 48 | GCGCAGAUCUUAGUUUAAUGGC |
| 49 | GCGCAGAUCUUAGUGUAUGGC |
| 50 | GCGCAGAUCUCAUUGUAUGGC |
| 51 | GCGCAGAUCUCAGUUUAUGGC |
| 52 | GCGCAGAUCUUAUUGCAUGGC |
| 53 | GCGCAGAUCUUAUUGUAUGGC |
| 54 | GCGCAGAUCUAAUUGUAAUGGC |
| 55 | AUUAAGGAUCCUUAGUGUAUGGC |

In some aspects, the disclosure provides nucleic acid compositions comprising a nucleotide sequence encoding a modified Kozak sequence and AAV VP1, VP2, and VP3 capsid proteins, wherein the capsid proteins are derived from an AAV6 serotype. In some embodiments, the Kozak sequence comprises the initiation codon for translation of the AAV6 VP1 capsid protein and additional nucleotides upstream of the initiation codon. In some embodiments, the Kozak sequence further comprises nucleotides downstream of the initiation codon. In some embodiments, the Kozak sequence comprises a nucleotide of sequence YLXUXR (AUG)XZ (SEQ ID NO: 81), wherein (AUG) is the VP1 initiation codon; X is a G or U nucleotide; Y is a nucleotide selected from A, U, or C; L is an A or G nucleotide; R is a C or U nucleotide; and Z is a G or C nucleotide. In some embodiments, the Kozak sequence comprises a nucleotide sequence listed in Table 5.

TABLE 5

AAV6 VP1 Kozak Sequences

| SEQ ID NO: | Sequence |
|---|---|
| 56 | UAGUUUAUGGC |
| 57 | CAGUUUAUGGC |
| 58 | UAUUGCAUGGC |
| 59 | UAGUGUAUGGC |
| 60 | AAUUGUAUGGC |
| 61 | UAUUGUAUGGC |
| 62 | CAUUGUAUGGC |
| 63 | UGUUUUAUGGG |
| 64 | UGUUUUAUGUC |
| 65 | UAUUUUAUGGG |
| 66 | UAGUUUAUGGG |
| 67 | UAGUUUAUGUC |

It should be appreciated that a U or a T nucleotide may be referred to depending on whether the nucleic acid that is being referred to is an RNA or DNA molecule, respectively.

The wild-type AAV genome is a single-stranded deoxyribonucleic acid (ssDNA), either positive- or negative-sensed. The genome comprises two inverted terminal repeats (ITRs), one at each end of the DNA strand, and two open reading frames (ORFs): rep and cap between the ITRs. The rep ORF comprises four overlapping genes encoding Rep proteins required for the AAV life cycle. The cap ORF comprises overlapping genes encoding capsid proteins: VP1, VP2, and VP3, which interact together to form the viral capsid. VP1, VP2, and VP3 are translated from one mRNA transcript, which can be spliced in two different manners: either a longer or shorter intron can be excised resulting in the formation of two isoforms of mRNAs: a ~2.3 kb- and a ~2.6 kb-long mRNA isoform. The capsid forms a supramolecular assembly of approximately 60 individual capsid protein subunits into a non-enveloped, T-1 icosahedral lattice capable of protecting the AAV genome. The mature capsid is composed of VP1, VP2, and VP3 (molecular masses of approximately 87, 73, and 62 kDa respectively) in an approximate ratio of about 1:1:10. The level of VP1 relative to VP2 and VP3 can be adjusted as described herein in order to obtain efficient production of infectious particles in insect cells. In some embodiments, the VP1:VP2:VP3 ratio is in the range of (0.5-2):(0.5-2):10. In some embodiments, the VP1:VP2:VP3 ratio is in the range of (0.5-1.5):(0.5-1.5):10.

Recombinant AAV (rAAV) particles may comprise a nucleic acid vector, which may comprise at a minimum: (a) one or more heterologous nucleic acid regions comprising a gene of interest encoding a protein or polypeptide of interest or an RNA of interest (e.g., siRNA or microRNA); and (b) one or more regions comprising inverted terminal repeat (ITR) sequences (e.g., wild-type ITR sequences or engineered ITR sequences) flanking the one or more nucleic acid regions (e.g., heterologous nucleic acid regions). In some embodiments, the nucleic acid vector is between 2 kb-7 kb in size. In some embodiments, the nucleic acid vector is between 4 kb and 5 kb in size (e.g., 4.2 to 4.7 kb in size). In some embodiments, the nucleic acid vector is circular. In some embodiments, the nucleic acid vector is single-stranded. In some embodiments, the nucleic acid vector is double-stranded. In some embodiments, a double-stranded nucleic acid vector may be, for example, a self-complimentary vector that contains a region of the nucleic acid vector that is complementary to another region of the nucleic acid vector, initiating the formation of the double-strandedness of the nucleic acid vector.

The ITR sequences can be derived from any AAV serotype (e.g., 1, 2, 3, 4, 5, 6, 7, 8, 9, or 10) or can be derived from more than one serotype. ITR sequences and plasmids containing ITR sequences are known in the art and commercially available (see, e.g., products and services available from Vector Biolabs, Philadelphia, Pa.; Cellbiolabs, San Diego, Calif.; Agilent Technologies, Santa Clara, Ca; and Addgene, Cambridge, Mass.; and Gene delivery to skeletal muscle results in sustained expression and systemic delivery of a therapeutic protein. Kessler P D, Podsakoff G M, Chen X, McQuiston S A, Colosi P C, Matelis L A, Kurtzman G J, Byrne B J. Proc Natl Acad Sci USA. 1996 Nov. 26; 93(24):14082-7; and Curtis A. Machida. Methods in Molecular Medicine™. Viral Vectors for Gene Therapy Methods and Protocols. 10.1385/1-59259-304-6:201 © Humana Press Inc. 2003. Chapter 10. Targeted Integration by Adeno-Associated Virus. Matthew D. Weitzman, Samuel M. Young Jr., Toni Cathomen and Richard Jude Samulski; U.S. Pat. Nos. 5,139,941 and 5,962,313, all of which are incorporated herein by reference).

In some embodiments, an rAAV particle or particle within an rAAV preparation may be of any AAV serotype, including any derivative or pseudotype (e.g., 1, 2, 3, 4, 5, 6, 7, 8, 9, 10, 2/1, 2/5, 2/8, 2/9, 3/1, 3/5, 3/8, or 3/9). As used herein, the serotype of an rAAV viral vector (e.g., an rAAV particle) refers to the serotype of the capsid proteins of the recombinant virus. Non-limiting examples of derivatives and pseudotypes include rAAV2/1, rAAV2/5, rAAV2/8, rAAV2/9, AAV2-AAV3 hybrid, AAVrh.10, AAVhu.14, AAV3a/3b, AAVrh32.33, AAV-HSC15, AAV-HSC17, AAVhu.37, AAVrh.8, CHt-P6, AAV2.5, AAV6.2, AAV2i8, AAV-HSC15/17, AAVM41, AAV9.45, AAV6(Y445F/Y731F), AAV2.5T, AAV-HAE1/2, AAV clone 32/83, AAVShH10, AAV2 (Y→F), AAV8 (Y733F), AAV2.15, AAV2.4, AAVM41, and AAVr3.45. Such AAV serotypes and derivatives/pseudotypes, and methods of producing such derivatives/pseudotypes are known in the art (see, e.g., Mol Ther. 2012 April; 20(4):699-708. doi: 10.1038/mt.2011.287. Epub 2012 Jan. 24. The AAV vector toolkit: poised at the clinical crossroads. Asokan A I, Schaffer D V, Samulski R J.). In some embodiments, the rAAV particle is a pseudotyped rAAV particle, which comprises (a) a nucleic acid vector comprising ITRs from one serotype (e.g., AAV2, AAV3) and (b) a capsid comprised of capsid proteins derived from another serotype (e.g., AAV1, AAV2, AAV3, AAV4, AAV5, AAV6, AAV7, AAV8, AAV9, or AAV10). In some embodiments, methods described herein may be used for producing AAV of any serotype, or derivative/pseudotype, (e.g., AAV5, AAV8, AAV9, AAV3, AAV6, or other serotype or derivative/pseudotype based thereon) in insect cells. Other methods for producing and using pseudotyped rAAV vectors are known in the art (see, e.g., Duan et al., J. Virol., 75:7662-7671, 2001; Halbert et al., J. Virol., 74:1524-1532, 2000; Zolotukhin et al., Methods, 28:158-167, 2002; and Auricchio et al., Hum. Molec. Genet., 10:3075-3081, 2001). In some embodiments, one or more capsid substitutions (e.g., relative to a corresponding wild-type sequence) may be encoded in a recombinant capsid gene (e.g., recombinant VP1 gene described in this application).

Methods of producing rAAV particles and nucleic acid vectors are described herein. Other methods are also known in the art and commercially available (see, e.g., Zolotukhin et al. Production and purification of serotype 1, 2, and 5 recombinant adeno-associated viral vectors. Methods 28 (2002) 158-167; and U.S. Patent Publication Numbers US20070015238 and US20120322861, which are incorporated herein by reference; and plasmids and kits available from ATCC and Cell Biolabs, Inc.). For example, a plasmid containing the nucleic acid vector may be combined with one or more helper plasmids, e.g., that contain a rep gene (e.g., encoding Rep78, Rep68, Rep52 and Rep40) and a cap gene (encoding VP1, VP2, and VP3, including a modified VP3 region as described herein), and transfected into a producer cell line such that the rAAV particle can be packaged and subsequently purified.

In some embodiments, the producer cell line is derived from an insect cell. Examples of insect cells include, but are not limited to Sf9 cells (see, e.g., ATCC® CRL-1711™). The producer cell may comprise rep and/or cap genes (e.g., a nucleic acid encoding AAV VP1, VP2, and VP3 as described herein) that encode the Rep protein and/or Cap proteins for use in a method described herein. In some embodiments, the packaging is performed in vitro.

In some embodiments of a method provided herein, a plasmid containing the nucleic acid vector is combined with one or more helper plasmids, e.g., that contain a rep gene of a first serotype and a cap gene of the same serotype or a different serotype, and transfected into a helper cell line such that the rAAV particle is packaged.

In some embodiments, the one or more helper plasmids include a first helper plasmid comprising a rep gene and a cap gene and a second helper plasmid comprising a E1a gene, a E1b gene, an E4 gene, a E2a gene, and a VA gene. In some embodiments, the rep gene is a rep gene derived from AAV2. Helper plasmids, and methods of making such plasmids, are known in the art and commercially available (see, e.g., pDM, pDG, pDP1rs, pDP2rs, pDP3rs, pDP4rs, pDP5rs, pDP6rs, pDG(R484E/R585E), and pDP8.ape plasmids from PlasmidFactory, Bielefeld, Germany; other products and services available from Vector Biolabs, Philadelphia, Pa.; Cellbiolabs, San Diego, Calif.; Agilent Technologies, Santa Clara, Ca; and Addgene, Cambridge, Mass.; pxx6; Grimm et al. (1998), Novel Tools for Production and Purification of Recombinant Adenoassociated Virus Vectors, Human Gene Therapy, Vol. 9, 2745-2760; Kern, A. et al. (2003), Identification of a Heparin-Binding Motif on Adeno-Associated Virus Type 2 Capsids, Journal of Virology, Vol. 77, 11072-11081.; Grimm et al. (2003), Helper Virus-Free, Optically Controllable, and Two-Plasmid-Based Production of Adeno-associated Virus Vectors of Serotypes 1 to 6, Molecular Therapy, Vol. 7, 839-850; Kronenberg et al. (2005), A Conformational Change in the Adeno-Associated Virus Type 2 Capsid Leads to the Exposure of Hidden VP1 N Termini, Journal of Virology, Vol. 79, 5296-5303; and Moullier, P. and Snyder, R. O. (2008), International efforts for recombinant adeno-associated viral vector reference standards, Molecular Therapy, Vol. 16, 1185-1188).

In some embodiments, one or more host cells (e.g., producer cells) can have one or more helper functions (e.g., encoded by recombinant nucleic acid integrated into the host cell genome, or encoded by a plasmid or viral nucleic acid vector in the host cell). In some embodiments, a recombinant capsid gene (e.g., VP1 gene) comprising a modified Kozak sequence as described in this application can be provided on a plasmid, a viral genome (e.g., a baculovirus, Herpes virus, adenovirus, or other viral genome), or integrated into the genome of a host cell (e.g., a mammalian or insect cell, for example an Sf9 cell).

In some embodiments, a gene of interest (e.g., a gene that is packaged in an rAAV particle) encodes an enzyme, hormone, antibody, receptor, ligand, or other protein. In some embodiments, a gene of interest encodes a therapeutically useful protein. In some embodiments, a gene of interest encodes a reference or marker protein (e.g., a detectable marker, for example GFP). In some embodiments, a gene of interest encodes an RNA, for example a regulatory RNA such as a siRNA or other regulatory RNA (e.g., a therapeutic RNA). In some embodiments, the therapeutic agent is a polypeptide, a peptide, an antibody or an antigen-binding fragment thereof, a ribozyme, a peptide-nucleic acid, an siRNA, an RNAi, an antisense oligonucleotide, or an antisense polynucleotide. In some embodiments, a gene of interest encodes a therapeutic protein. In some embodiments, a therapeutic gene encodes an antibody, a peptibody, a growth factor, a clotting factor, a hormone, a membrane protein, a cytokine, a chemokine, an activating or inhibitory peptide acting on cell surface receptors or ion channels, a cell-permeant peptide targeting intracellular processes, a thrombolytic, an enzyme, a bone morphogenetic proteins, a nuclease or other protein used for gene editing, an Fc-fusion protein, an anticoagulant, a nuclease, guide RNA or other nucleic acid or protein for gene editing. In some embodiments, a therapeutic protein is therapeutic for a lysosomal storage disease. In some embodiments, a therapeutic protein is therapeutic for a neurological disability, a neuromotor deficit, a neuroskeletal impairment or a neuromuscular disease. In some embodiments, a therapeutic protein is therapeutic for a muscular disability or dystrophy, a myopathy or a cardiomyopathy. In some embodiments, a gene of interest encodes a vaccine (e.g., a nucleic acid or peptide vaccine).

In some embodiments, a gene of interest (e.g., encoding a therapeutic agent) is operably linked to a promoter. A promoter can be, but is not limited to, a natural promoter, a synthetic or recombinant promoter, a chimeric promoter, a truncated promoter, a constitutive promoter, an inducible promoter, a species-specific promoter, a tissue-specific promoter, or a combination of two or more of the foregoing. In some embodiments, a promoter may be regulatable (e.g., the level of expression from the promoter may be increased or reduced by changing an external condition or by adding or removing a regulatory molecule). In some embodiments, a gene of interest may be operably linker to its natural promoter, or alternatively to a different promoter.

In some embodiments, a composition comprising an rAAV described herein can be used to treat a mammalian subject (e.g., a human). In some embodiments, the subject has cancer, diabetes, autoimmune disease, kidney disease, cardiovascular disease, pancreatic disease, intestinal disease, liver disease, neurological disease, neuromuscular disease, Bratten's disease, Alzheimer's disease, Huntington disease, Parkinson's disease, pulmonary disease, an α-1.alpha.-1 antitrypsin deficiency, neurological disability, neuromotor deficit, neuroskeletal impairment, ischemia, stroke, a lysosomal storage disease, Pompe disease, Duchenne Muscular Dystrophy, Friedreich's Ataxia, Canavan disease, Aromatic L-amino acid decarboxylase deficiency, Hemophilia A/B, or other disease, or any combination thereof.

Without further elaboration, it is believed that one skilled in the art can, based on the above description, utilize the present disclosure to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

EXAMPLES

Example 1: Modulating VP1:VP2:VP3 Ratios in Stable Cell Lines Using Attenuated Kozak Sequences The biological potency (e.g., infectivity) of rAAV particles partly depends on the virion capsid composition, for example, the stoichiometric ratios of the capsid proteins VP1, VP2, and VP3. Some rAAV serotypes (e.g., AAV5, AAV8, AAV9, AAV3 and AAV6) manufactured in a heterologous system such as insect cells (e.g., Sf9 cells) are characterized by abnormal VP1 expression levels. Upon viral assembly, the abnormal VP1 expression results in the production of viral particles comprised of improper capsid protein ratios, which hinders the ability of the particles to efficiently transduce cells. Methods of obtaining useful stoichiometric ratios of capsid proteins are complicated by results indicating that an overabundance of VP1 can impair the insect cell's ability to efficiently package the viral particle while low levels of VP1 can result in particles with inefficient transduction. Thus, with respect to insect cell rAAV production using current systems, it remains a challenge to find a method of increasing the yield of infective particles without detrimentally affecting particle assembly.

The current investigation seeks to improve capsid protein ratios by modulating the initiation of the translation rate of VP1 in rAAV expressed in Sf9 insect cells. Specifically, the Kozak sequences of VP1 in AAV5, AAV8, AAV9, AAV3 and AAV6 were attenuated while the canonical ATG start codon was kept constant, and transduction efficiencies were measured to assess the assembled particles.

Figure 2A:
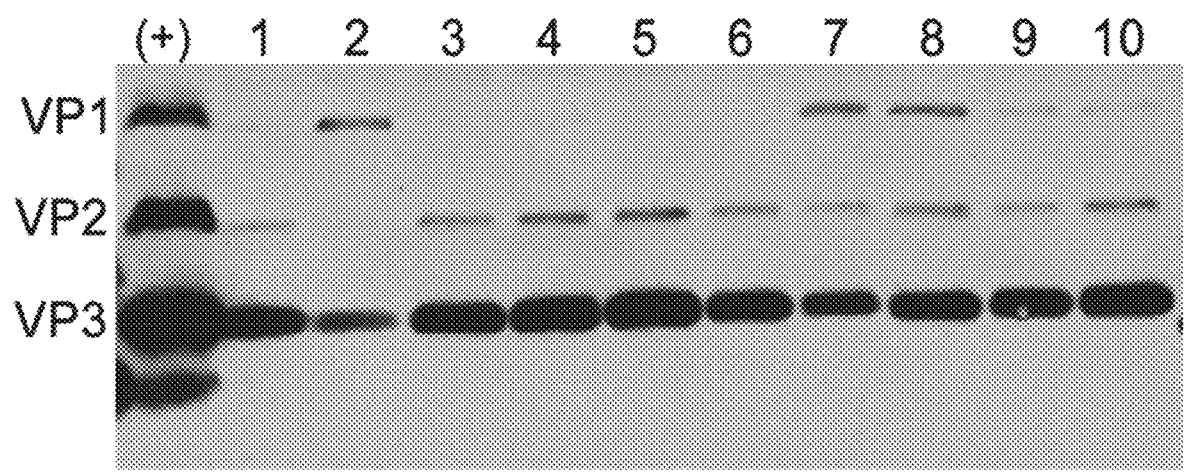
FIG. 2A depicts an example of a Western blotting analysis of rAAV5 packaged in Sf9 cells.
Figure 4A:
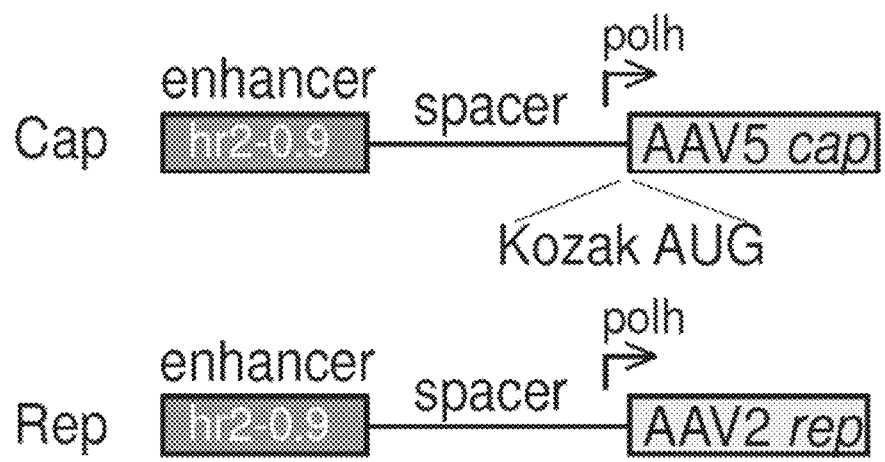
FIGS. 4A-4D depict non-limiting examples of capsid protein compositions of rAAV particles produced in Sf9 cells.
Figure 4B:
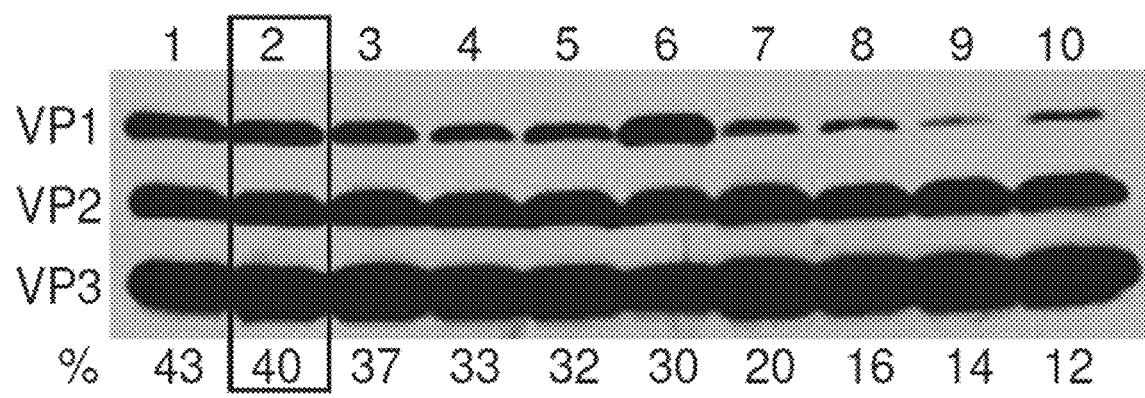

A set of attenuated Kozak elements were designed for AAV5, and nucleic acids encoding these elements were generated. The encoded Kozak sequences are shown in Table 6. A subset of four Kozak elements were found to encode for capsid proteins with ratios close to the wild-type AAV5 VP1:VP2:VP3 ratio of 1:1:10, as illustrated by Western blotting analysis depicted in FIG. 2A. For these elements (AAV5 Kozak sequences 7-10), the respective ratios of (VP1):(VP2):(VP3) were within the ranges of (0.5-2):(0.5-1):10. In vitro relative efficiencies of Translation Initiation Sequences (TIS, also referred to as Kozak sequences) have been measured for each assembled particle (Table 6). These numbers correspond to the numbers below the Western blotting panel in FIG. 4B. AAV5 Kozak Sequences 7 (SEQ ID NO: 8) and 8 (SEQ ID NO: 9) produced rAAV exhibiting the greatest efficiencies and were selected for further analysis.

TABLE 6

AAV5 VP1 Kozak Sequences

| Sequence | Kozak Sequence | Efficiency (%) |
|---|---|---|
| 1 | CAUUGUAUGUC (SEQ ID NO: 2) | 32 |
| 2 | UCGUUUAUGGA (SEQ ID NO: 3) | 30 |
| 3 | CAGUUUAUGGU (SEQ ID NO: 4) | 20 |
| 4 | CAUUGUAUGGU (SEQ ID NO: 5) | 16 |
| 5 | UAGUGUAUGCU (SEQ ID NO: 6) | 14 |
| 6 | CAUUGUAUGCU (SEQ ID NO: 7) | 12 |
| 7 | UCUUUUAUGUC (SEQ ID NO: 8) | 43 |
| 8 | UGUUUUAUGUC (SEQ ID NO: 9) | 40 |
| 9 | UAGUUUAUGUC (SEQ ID NO: 10) | 37 |
| 10 | UAGUGUAUGUC (SEQ ID NO: 11) | 33 |

AAV5 Kozak sequence 7 generated a respective VP1:VP2:VP3 ratio of 2:1:(8-9). In comparison with AAV5 isolated from HEK 293 cells, sequence 7 particles generated in insect cells displayed 2-fold greater transduction efficiency. AAV5 Kozak sequence 8 generated a respective VP1:VP2:VP3 ratio of (1-1.5):1:10. In comparison with AAV5 isolated from HEK 293 cells, sequence 8 particles displayed 3- to 5-fold greater transduction efficiency. It was noted that the yield of the packaged rAAV5 variant of sequence 8 was approximately 10 times higher than that of sequence 7.

A set of attenuated Kozak elements were designed for AAV8, and nucleic acids encoding these elements were generated. The encoded Kozak sequences are shown in Table 7.

TABLE 7

AAV8 VP1 Kozak Sequences

| Sequence | Kozak Sequence | Efficiency (%) |
|---|---|---|
| 1 | UAGCGCAUGGC (SEQ ID NO: 13) | 70 |
| 2 | UGGUAUAUGGC (SEQ ID NO: 14) | 60 |
| 3 | UAGUUUAUGGC (SEQ ID NO: 15) | 50 |
| 4 | CAGUGUAUGGC (SEQ ID NO: 16) | 46-47 |
| 5 | UAGUGUAUGGC (SEQ ID NO: 17) | 45 |
| 6 | UAUUGUAUGGC (SEQ ID NO: 18) | 44 |
| 7 | CAUUGUAUGGC (SEQ ID NO: 19) | 43 |
| 8 | CCGUUUAUGGG (SEQ ID NO: 20) | 41-42 |
| 9 | ACUUGUAUGGG (SEQ ID NO: 21) | 40 |
| 10 | CAUUUUAUGGG (SEQ ID NO: 22) | 37 |
| 11 | UAGUGUAUGUC (SEQ ID NO: 23) | 34 |
| 12 | UAGUUUAUGUC (SEQ ID NO: 24) | 31 |
| 13 | UGUUUUAUGUC (SEQ ID NO: 25) | 33 |
| 14 | UCUUUUAUGUC (SEQ ID NO: 26) | 37 |
| 15 | UAGUGUAUGGG (SEQ ID NO: 27) | 40 |
| 16 | UAGUUUAUGGG (SEQ ID NO: 28) | 43 |
| 17 | UGUUUUAUGGG (SEQ ID NO: 29) | 33 |
| 18 | UCUUUUAUGGG (SEQ ID NO: 30) | 38 |
| 19 | UAGUGUAUGUC (SEQ ID NO: 31) | 42 |
| 20 | UAGUUUAUGUC (SEQ ID NO: 32) | 43 |

Figure 2B:
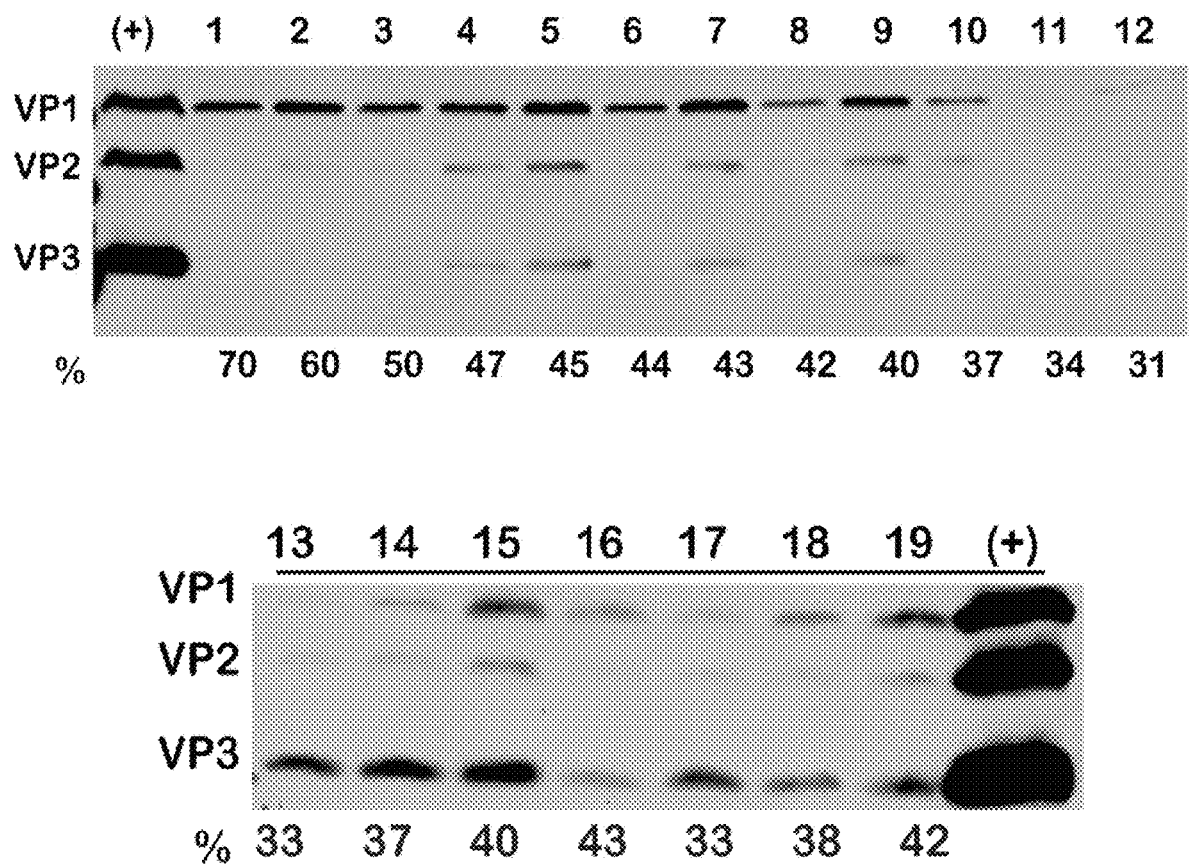
FIG. 2B depicts an example of a Western blotting analysis of rAAV8 packaged in Sf9 cells.

AAV8 Kozak sequences 1-12 demonstrated hyper-expression of VP1 and low expression of VP2 and VP3, as illustrated by Western blotting analysis depicted in FIG. 2B. These sequences were excluded from subsequent testing. The remaining elements (sequences 13-20) directed the expression of VP1:VP2:VP3 in similar ratios to AAV8 isolated from HEK293 cells.

A set of attenuated Kozak elements were designed for AAV9, and nucleic acids encoding these elements were generated. The encoded Kozak sequences are shown in Table 8.

TABLE 8

AAV9 VP1 Kozak Sequences

| Sequence | Kozak Sequence | Efficiency (%) |
|---|---|---|
| 1 | UAGUGUAUGUC (SEQ ID NO: 34) | 33 |
| 2 | UAGUUUAUGUC (SEQ ID NO: 35) | 37 |
| 3 | UGUUUUAUGUC (SEQ ID NO: 36) | 40 |
| 4 | UCUUUUAUGUC (SEQ ID NO: 37) | 43 |
| 5 | UAGUGUAUGGG (SEQ ID NO: 38) | 33 |
| 6 | UAGUUUAUGGG (SEQ ID NO: 39) | 38 |
| 7 | UGUUUUAUGGG (SEQ ID NO: 40) | 42 |
| 8 | UCUUUUAUGGG (SEQ ID NO: 41) | 43 |
| 9 | UAGUGUAUGGC (SEQ ID NO: 42) | 45 |
| 10 | UAGUUUAUGGC (SEQ ID NO: 43) | 50 |
| 11 | UGUUUUAUGGC (SEQ ID NO: 44) | 54 |
| 12 | UCUUUUAUGGC (SEQ ID NO: 45) | 57 |

Figure 2C:
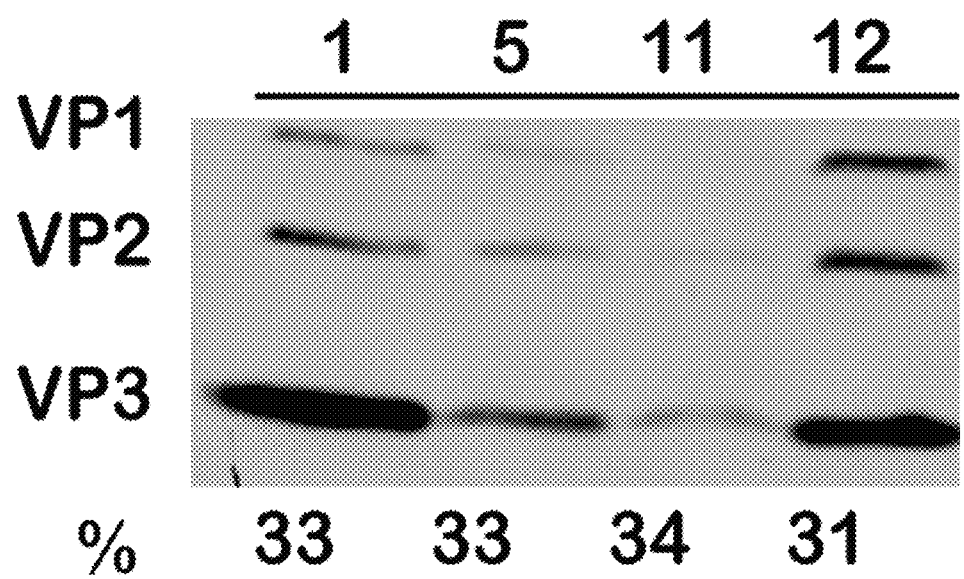
FIG. 2C depicts an example of a Western blotting analysis of rAAV9 packaged in Sf9 cells.
Figure 3:
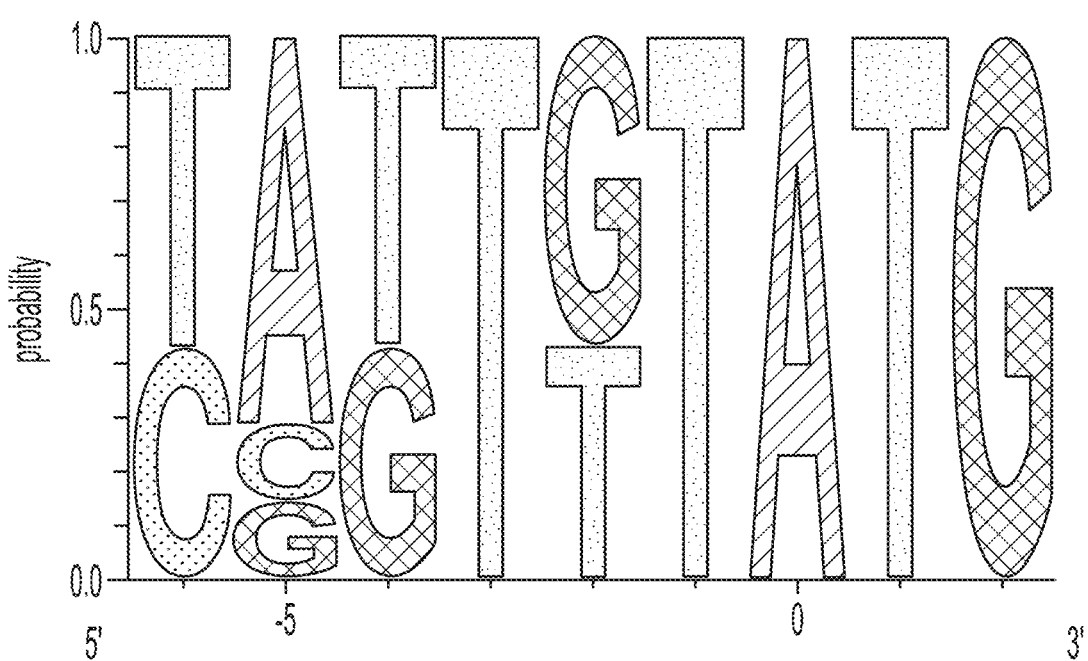
FIG. 3 depicts a non-limiting nucleotide sequence of a consensus attenuated Kozak element upstream of the VP1 capsid gene designed for expression in insect cells.

AAV9 Kozak sequences 2 (SEQ ID NO: 35), 3 (SEQ ID NO: 36), 5 (SEQ ID NO: 38), and 9 (SEQ ID NO: 42) directed AAV9 capsids with satisfactory VP1:VP2:VP3 ratios, as illustrated by Western blotting analysis depicted in FIG. 2C. Taking into account the experiments performed with each AAV serotype, a "consensus" attenuated Kozak element was derived. As shown in FIG. 3, the position that is −5 (5 nucleotides upstream from the start codon) is the most flexible for the precise regulation of VP1:VP2:VP3 expression ratio for a given capsid selected from AAV serotypes 5, 8, and 9.

A set of attenuated Kozak elements were designed for AAV6, and nucleic acids encoding these elements were generated. The encoded Kozak sequences are shown in Table 9.

TABLE 9

AAV6 VP1 Kozak Sequences

| Sequence | Kozak Sequence | Efficiency (%) |
|---|---|---|
| 1 | UAGUUUAUGGC (SEQ ID NO: 56) | 50 |
| 2 | CAGUUUAUGGC (SEQ ID NO: 57) | 50 |
| 3 | UAUUGCAUGGC (SEQ ID NO: 58) | 47 |
| 4 | UAGUGUAUGGC (SEQ ID NO: 59) | 45 |
| 5 | AAUUGUAUGGC (SEQ ID NO: 60) | 45 |
| 6 | UAUUGUAUGGC (SEQ ID NO: 61) | 44 |
| 7 | CAUUGUAUGGC (SEQ ID NO: 62) | 43 |
| 8 | UGUUUUAUGGG (SEQ ID NO: 63) | 42 |
| 9 | UGUUUUAUGUC (SEQ ID NO: 64) | 40 |
| 10 | UAUUUUAUGGG (SEQ ID NO: 65) | 39 |
| 11 | UAGUUUAUGGG (SEQ ID NO: 66) | 38 |
| 12 | UAGUUUAUGUC (SEQ ID NO: 67) | 37 |

Example 2: Evaluating rAAV

The major drawback of the Baculovirus/Sf9 system for rAAV manufacturing is that most of the Bac-derived rAAV vector serotypes, with few exceptions, demonstrate altered capsid compositions and lower biological potencies. A new insect cell-based production platform utilizing attenuated Kozak sequence and a leaky ribosome scanning to achieve a serotype-specific modulation of AAV capsid proteins stoichiometry is described. By way of example, rAAV5 and rAAV9 were produced and comprehensively characterized, side-by-side with HEK 293 derived vectors. A mass spectrometry analysis documented a three-fold increase in both VP1 and VP2 capsid protein content compared to human cells-derived vectors. Furthermore, an extensive analysis of encapsidated single-stranded viral DNA was conducted using Next-Generation Sequencing and showed a six-fold reduction in collaterally packaged contaminating DNA for rAAV5 produced in insect cells. Consequently, the re-designed rAAVs demonstrated significantly higher biological potencies, even in a comparison to HEK 293-manufactured rAAVs mediating, in case of rAAV5, four-fold higher transduction of brain tissues in mice. Thus, the described system yields rAAV vectors of superior infectivity and exceptional purity providing a scalable platform for GMP grade vector production.

rAAV is extensively used as a vector for gene therapy/ DNA vaccine delivery, but a scale-up production of a highly infectious rAAVs for clinical trials remains a challenging proposition. AAV capsid consists of three capsid proteins, VP1, VP2, and VP3, derived via alternative splicing and differential codon usage of a single capsid gene in AAV genome. The VP3 sequence is common between all three splice variants, and VP2 and VP1 have N-terminal longer sequences, with unique region of VP1 containing a phospholipase domain A2 critical for virus infection[1]. The exact amounts of VP1/VP2/VP3 in the capsid are unknown but estimated to be 1/1/10, based on densitometry analyses of the capsid proteins resolved on SDS-PAGE[2-4]. Moreover, it appears that there is no defined VP1/VP2/VP3 stoichiometry and that the assembly is stochastic such that the relative amoun37t of VP1/VP2/VP3 that is incorporated in the capsid depends mainly on their relative expression levels[5]. Therefore, the design of capsid proteins expression unit in a given rAAV production system is essential for the assembly of biologically potent gene therapy vectors.

Towards this goal, one of the original scalable systems utilized a suspension culture of Sf9 insect cells co-infected with three recombinant baculoviruses derived from A. californica multicapsid nucleopolyhedrovirus (AcMNPV) encoding, respectively, rAAV transgene cassette, AAV rep, and cap helper genes[6]. Most of the AAV serotypes produced in this system, however, were characterized by low transduction efficiencies compared to HEK 293-derived vectors due to an inappropriate content of VP1 capsid protein and its phospholipase A2 activity[7-10]. This shortcoming resulted from the capsid gene helper vector design utilizing a non-canonical ACG initiation codon for VP1 to induce a leaky ribosome scanning. Even though other groups resolved the problem to some extent utilizing a different initiation codon CUG[11] or artificial intron[12], the solutions appeared to lack the flexibility necessary for a serotype-specific sequence adjustment. A novel system of regulation of a relative VP1/VP2/VP3 composition via adjustable leaky ribosome scanning is introduced.

In cells of mammalian origin, a P40-driven transcript in AAV undergoes splicing to produce two spliced mRNA variants encoding VP1, or VP2/VP3 capsid proteins, respectively. Because in the baculovirus/Sf9 system the polh promoter is substituted for the P40/intron sequence, the regulation by splicing is not available and alternative regulation of the VP1 expression via leaky ribosome scanning is used. A consensus sequence GCCRCCAUGGC (SEQ ID NO: 71) (R=A or G) is considered to be an effective mammalian translation initiation site (TIS), also known as Kozak sequence[13]. Any deviation from this sequence would increase leaky scanning of the VP1 AUG and initiation of translation from the in-frame downstream VP2 ACG or VP3 AUG codons thus changing the VP1/VP2/VP3 stoichiometry. In the current work, an approach for rationally modulating the ratios of VP1/VP2/VP3 capsid composition in a Baculovirus/Sf9 system to derive particles with a higher VP1/VP2 content resulting in significantly greater biological potency even compared to HEK 293-derived vectors is described.

To characterize this advanced production platform in its entirety, a Next-generation sequence (NGS) analysis of encapsidated DNA manufactured was conducted by two methods: a conventional triple plasmid co-transfection of HEK 293 and single BEV infection of Sf9 cell line incorporating stably integrated rep/cap helper genes. Direct side-by-side NGS analysis of the rAAV cassettes manufactured by two platforms revealed higher precision of viral DNA packaging in insect cells encapsidating significantly less contaminating DNA.

Design of AAV5 and rAAV9 Capsid Genes.

To increase a leaky ribosome scanning a canonical AUG codon preceded by attenuated Kozak sequences was used. Randomly modifying nucleotides up- or downstream of the AUG would not be a realistic approach because the complexity of the possible TIS sequences spanning the relevant stretch of eight residues is 65,536 possible permutations.

Moreover, the consensus Kozak sequence appears to be different for yeast[14], higher plants[15], invertebrates[16], or vertebrates[17]. Therefore, one way to rationalize the screening of attenuated TISs was to utilize the empirical heat map of all possible mammalian TIS permutations derived by Noderer et al.[18] whereby all possible combinations of TISs were assigned "initiation efficiency" values relative to the consensus Kozak sequence.

A range of 12-43% initiation efficiency was selected and tested for ten mutants differing by 2-4% increments. All ten AAV5 VP1 tested TISs are shown in Table 10 and were used in the context of cap-expressing helper plasmids (FIG. 4A) to derive $BS^R$ pooled cell lines as described previously[7] and assess their capsid compositions. With a few notable exceptions (e.g., FIG. 4B, lane 6), the relative VP1 content gradually decreased, while closely following the theoretical value decreases of the relative TIS efficiencies. This correlation supports the original hypothesis that leaky scanning translation initiation can be utilized to modulate VP1 content. To further identify useful VP1/VP2/VP3 stoichiometries, the infectious and overall titers of the respective ten rAAV5 vectors were assayed. To produce infectious rAAV5 vector, the BEV encoding CBA-driven GFP (FIG. 10A, pTR-Bac-UF26) was generated. Side-by-side comparison revealed that the construct with 40% TIS relative efficiency (FIG. 4B, lane 2) was superior compared to all other constructs producing the highest yield. Thus, this particular capsid gene-containing helper construct incorporating the attenuated TIS, UGUUUUAUGUC (SEQ ID NO: 9 in Table 10), was chosen to derive a producer cell line. However, other sequences also can be used. In a similar manner, twelve AAV9 VP1 plasmid constructs with attenuated Kozak sequences were screened (Table 10). For AAV9, a particularly useful sequence was UAGUGUAUGGC (SEQ ID NO: 42), constituting 45% of relative TIS efficiency. However, other sequences also can be used.

Characterization of the Rep2/Cap5 Stable Cell Line.

Individual cell lines were derived using Rep2- and Cap5-expressing plasmids devoid of Rep-binding elements (RBE)[8]. Cap5 helper contained the following attenuated TIS: UGUUUUAUGUC (SEQ ID NO: 9). Five individual cell lines were propagated and tested as described earlier[7]. One cell line, dubbed B8, showing the highest yield of rAAV5-UF26 was chosen for further characterization. The following parameters were investigated.

TABLE 10

WT and attenuated TISs tested for the expression of AAV5 and AAV9 capsid genes.

| | Sequence | Efficiency (%)* |
|---|---|---|
| AAV5 Koz VP1 | | |
| wtAAV5 | GUAGUCAUGUC (SEQ ID NO: 68) | 91 |
| 1 | UCUUUUAUGUC (SEQ ID NO: 8) | 43 |
| 2 | UGUUUUAUGUC (SEQ ID NO: 9) | 40 |
| 3 | UAGUUUAUGUC (SEQ ID NO: 10) | 37 |
| 4 | UAGUGUAUGUC (SEQ ID NO: 11) | 33 |
| 5 | CAUUGUAUGUC (SEQ ID NO: 2) | 32 |
| 6 | UCGUUUAUGGA (SEQ ID NO: 3) | 30 |
| 7 | CAGUUUAUGGU (SEQ ID NO: 4) | 20 |
| 8 | CAUUGUAUGGU (SEQ ID NO: 5) | 16 |
| 9 | UAGUGUAUGCU (SEQ ID NO: 6) | 14 |
| 10 | CAUUGUAUGCU (SEQ ID NO: 7) | 12 |
| AAV9 Koz VP1 | | |
| wtAAV9 | CCAGGUAUGGC (SEQ ID NO: 69) | 130 |
| 1 | UCUUUUAUGGC (SEQ ID NO: 45) | 57 |
| 2 | UGUUUUAUGGC (SEQ ID NO: 44) | 54 |
| 3 | UAGUUUAUGGC (SEQ ID NO: 43) | 50 |
| 4 | UAGUGUAUGGC (SEQ ID NO: 42) | 45 |
| 5 | UCUUUUAUGGG (SEQ ID NO: 41) | 43 |
| 6 | UCUUUUAUGUC (SEQ ID NO: 37) | 43 |
| 7 | UGUUUUAUGGG (SEQ ID NO: 40) | 42 |
| 8 | UGUUUUAUGUC (SEQ ID NO: 36) | 40 |
| 9 | UAGUUUAUGGG (SEQ ID NO: 39) | 38 |
| 10 | UAGUUUAUGUC (SEQ ID NO: 35) | 37 |
| 11 | UAGUGUAUGGG (SEQ ID NO: 38) | 33 |
| 12 | UAGUGUAUGUC (SEQ ID NO: 34) | 33 |

*Estimated relative TIS efficiencies[18]
Selected sequences for each serotype are highlighted in bold.
Underline indicates the VP1 start codon.

VP1/VP2/VP3 Stoichiometry.

Figures 4C, 4D:
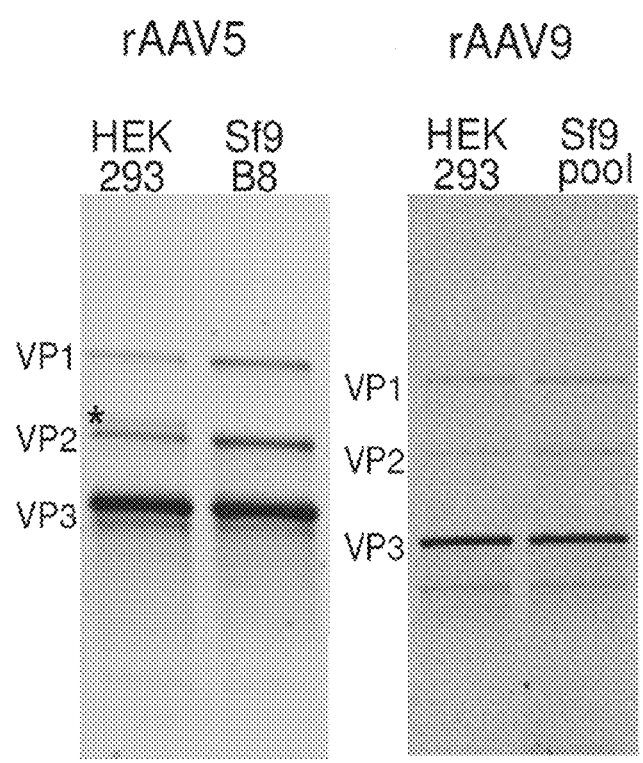

The capsid composition of rAAV5-GFP purified from HEK 293 cells by sequential double iodixanol gradient deviated from the theoretical value of 1/1/10 for VP1/VP2/VP3 in that it contained a lower VP1 content (FIG. 4C). Moreover, this capsid incorporated an additional VP2 capsid protein with slightly higher MW. In contrast, the Sf9 B8-derived vector composed of higher levels of VP1 and VP2 (FIG. 4C). For rAAV9, the capsid composition of Sf9-derived vector was almost identical to that of the vector manufactured in HEK 293 cells (FIG. 4D). Unlike rAAV5, both viral samples appear to incorporate more VP1 than VP2 and also to contain the bands smaller than VP3 which could be a product of a capsid-specific proteolysis[19].

Figure 11:
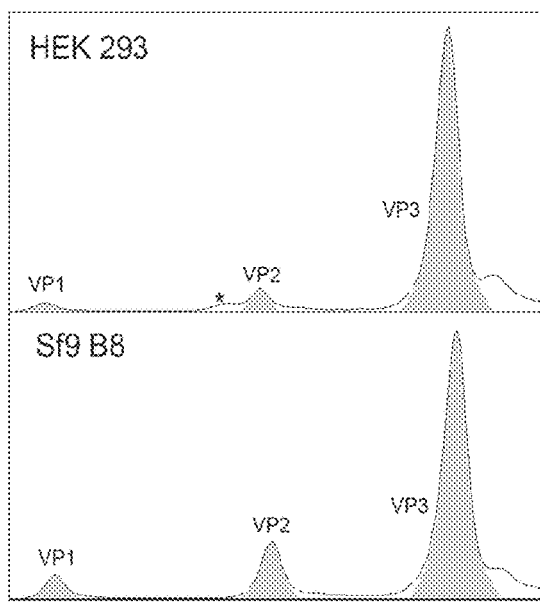
FIG. 11 depicts scanned profiles of rAAV5 preparations separated by SDS-PAGE electrophoresis (FIG. 4C). Shaded areas indicate areas-under-the-curves (AUCs) drawn for quantifications. (*) indicates the peak excluded from the analysis.

To quantify the exact numerical values, the densities of the respective capsid bands for rAAV5 were plotted as areas under the curves (AUCs) (FIG. 11). The following values (averages of two independent experiments, adjusted to a common denominator of VP3=10) were derived: HEK 293 VP1/VP2/VP3=0.2/0.5/10; Sf9 B8 VP1/VP2/VP3=0.7/1.7/10. To validate the calculated stoichiometry rAAV5 capsid composition was analyzed by mass spectrometry using Matrix Assisted Laser Desorption/Ionization-Time of Flight (MALDI-TOF).

MALDI-TOF.

AAV VPs constituting the virion shell share their VP3 C-termini (FIG. 5A, shown in black). VP1 (dashed), and VP2 (dot-dashed) unique N-termini are relatively small compared to the common shared VP3 domain creating a challenge to decipher relative stoichiometry by analyzing their unique tryptic peptides. Therefore, a differential 16O/18O labeling approach was used to discriminate identical peptides but derived from VP1, VP2 or VP3. When heavy-oxygen stable isotope water $H_2^{18}O$ is used during the trypsin digestion, two $^{18}O$ atoms are exchanged at the C-terminal carboxyl group of the tryptic peptides shifting the mass by 4 Da[20, 21]. This shift between the identical peptides derived from two different proteins (e.g., VP1 or VP3) allows for the identification and quantitation of the proteins.

Figure 5B:
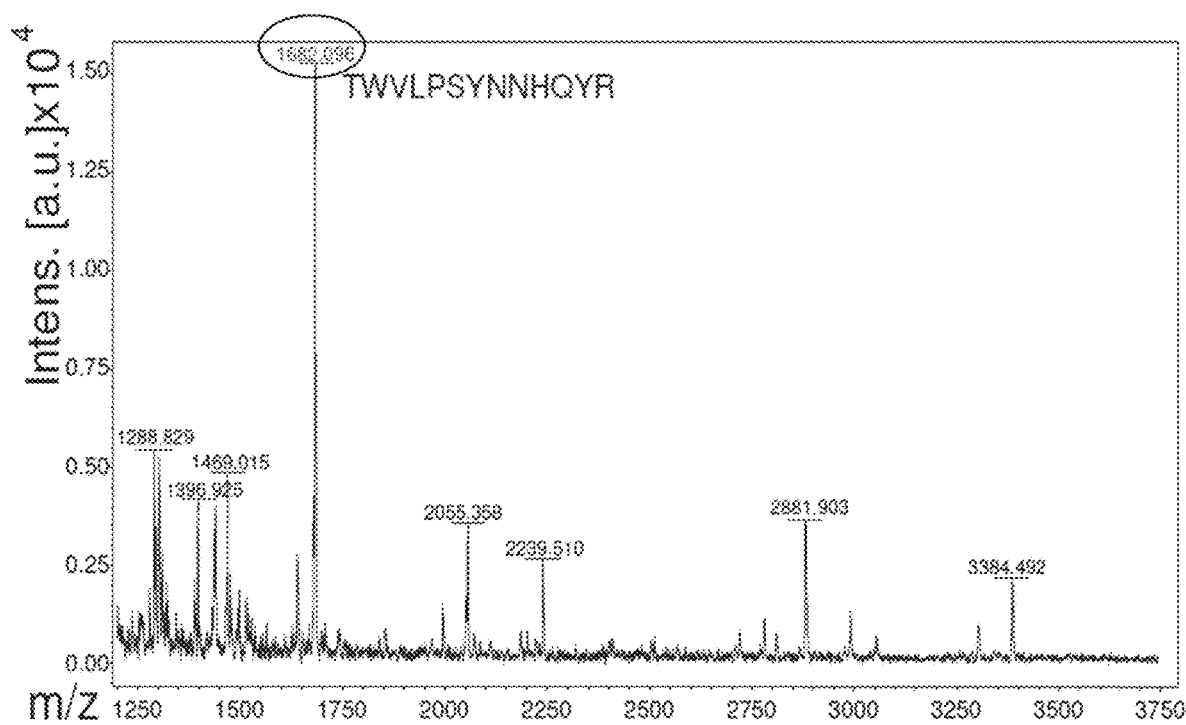
Figure 5C:
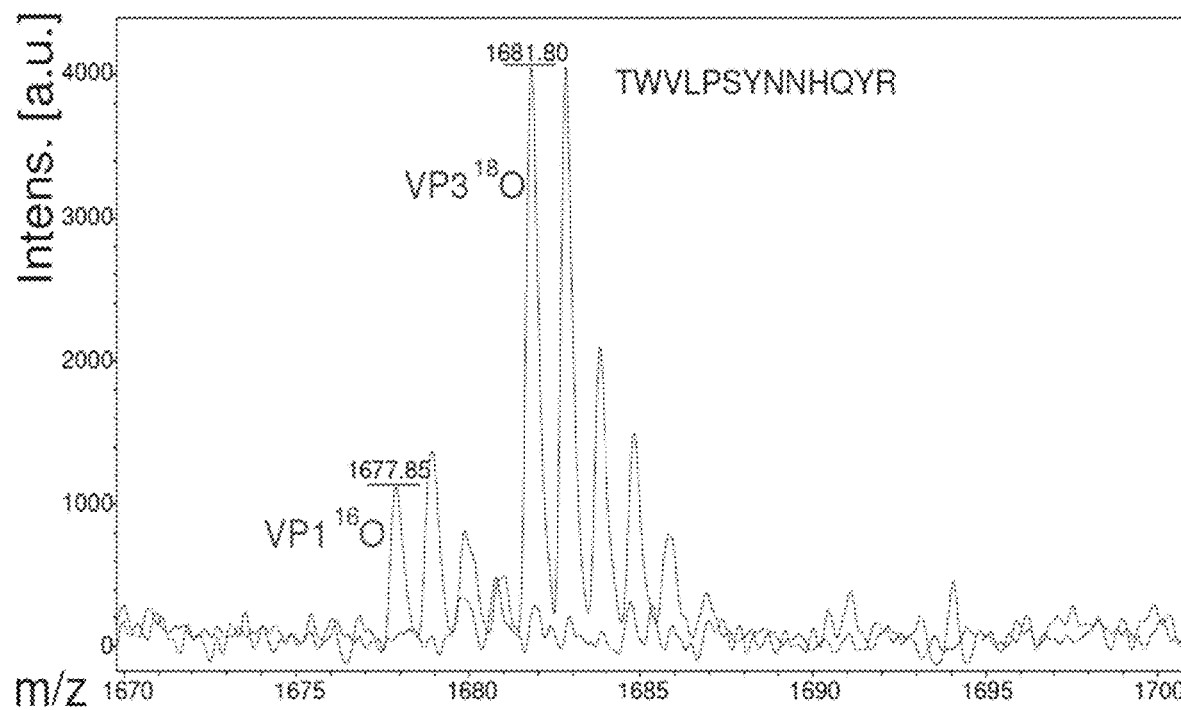
Figure 5D:
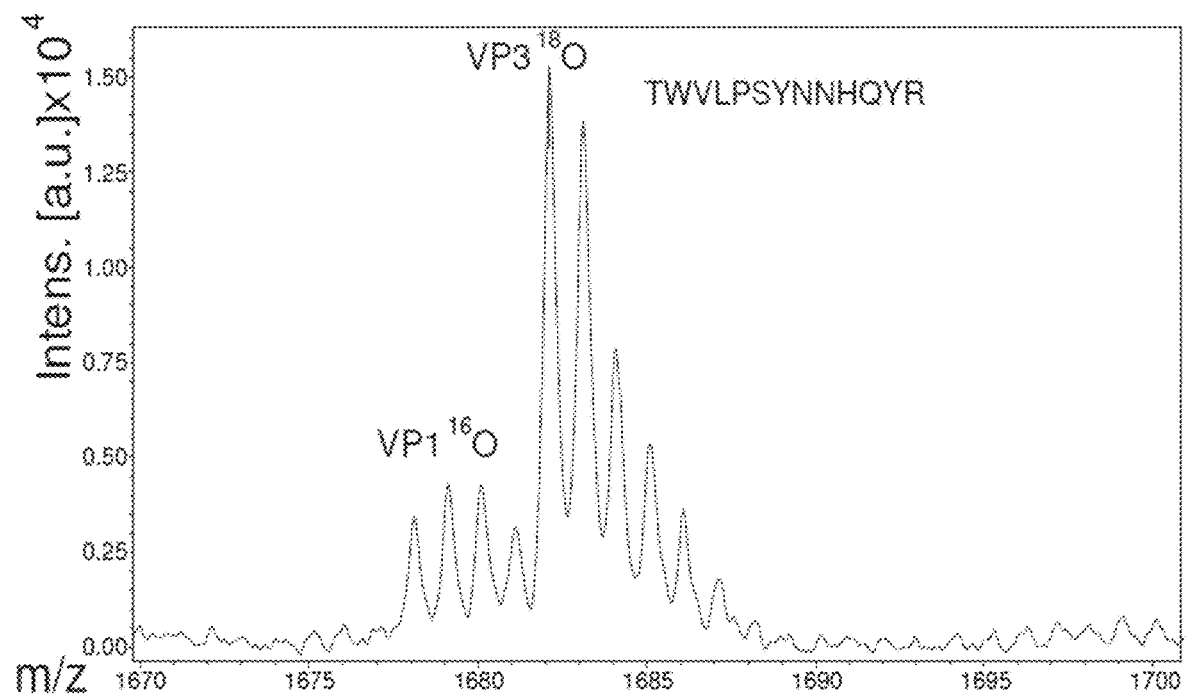

After conducting the pilot digestion, three peptides (FIG. 5A) in the VP3 region were chosen to quantitate the relative abundances of each protein. A complete incorporation of two $^{18}O$ atoms was confirmed by running the VP3/VP1- and VP2/VP3 samples separately. Then, the full MALDI spectrum of all the VP3 digestion tryptic products in $H_2^{18}O$ was analyzed (FIG. 5B). All of the peptides showed a 4 Da mass shift from the predicted peptide molecular weights confirming two $^{18}O$ atoms are incorporated. If the mass shift observed is only 2 Da then either the reaction is not complete or back exchange from incomplete trypsin inactivation was occurring[20]. FIG. 5C shows an overlay of the tryptic peptide TWVLPSYNNHQYR (SEQ ID NO: 60) from either VP1 or VP3 spotted separately and analyzed by MALDI-TOF. The distinct mass shift of 4 Da for the VP3 sample proved a complete $^{18}O$ atom exchange with no evidence of a back exchange. FIG. 5D shows representative MALDI-TOF spectra of VP3 digested with $H_2^{18}O$ and mixed 1:1 with VP1 digested in $H_2^{16}O$. The peak areas were integrated and used to calculate the abundance of each protein.

Three unique peptides (FIG. 5A) per each protein were analyzed, each—in three replicate MALDI-TOF runs (Tables 11 and 12). This allowed for a high confidence quantification of their relative abundance[22]. The following values (average of three independent experiments, adjusted to a common denominator of VP3=10) were derived: HEK 293 VP1/VP2/VP3=0.4/0.5/10; Sf9 B8 VP1/VP2/VP3=1.1/1.7/10. These numbers were remarkably consistent with the AUC densities described above.

TABLE 11

VP1/VP3 ions, intensities and ratios.

| Ion, M/Z* | HEK, VP1/VP3 | | | | B8, VP1/VP3 | | | |
|---|---|---|---|---|---|---|---|---|
| | I | II | III | Average | I | II | III | Average |
| 1464 | 0.029 | 0.031 | 0.022 | 0.027 | 0.101 | 0.13446 | 0.101408 | 0.11228932 |
| 1677 | 0.057 | 0.059 | 0.018 | 0.045 | 0.1123019 | 0.1475244 | 0.123 | 0.12760876 |
| 2051 | 0.04 | 0.038 | 0.026 | 0.035 | 0.178 | 0.1548061 | 0.09411 | 0.14230537 |
| | Total Average: 0.036 | | | | Total Average: 0.127 | | | |

*M/Z represents mass divided by charge number.

TABLE 12

VP2/VP3 ions, intensities and ratios.

| Ion, M/Z* | HEK, VP2/VP3 | | | | B8, VP2/VP3 | | | |
|---|---|---|---|---|---|---|---|---|
| | I | II | III | Average | I | II | III | Average |
| 1464 | 0.046521 | 0.045163 | 0.037953 | 0.043 | 0.177247 | 0.203963 | 0.218152 | 0.1997873 |
| 1677 | 0.045479 | 0.044517 | 0.027105 | 0.039 | 0.162602 | 0.178148 | 0.150699 | 0.1638163 |
| 2051 | 0.040742 | 0.031026 | 0.031464 | 0.034 | 0.22123 | 0.137658 | 0.165207 | 0.1746982 |
| | Total Average: 0.039 | | | | Total Average: 0.179 | | | |

*M/Z represents mass divided by charge number.

Full/Empty Particles Ratios.

Figure 6D:
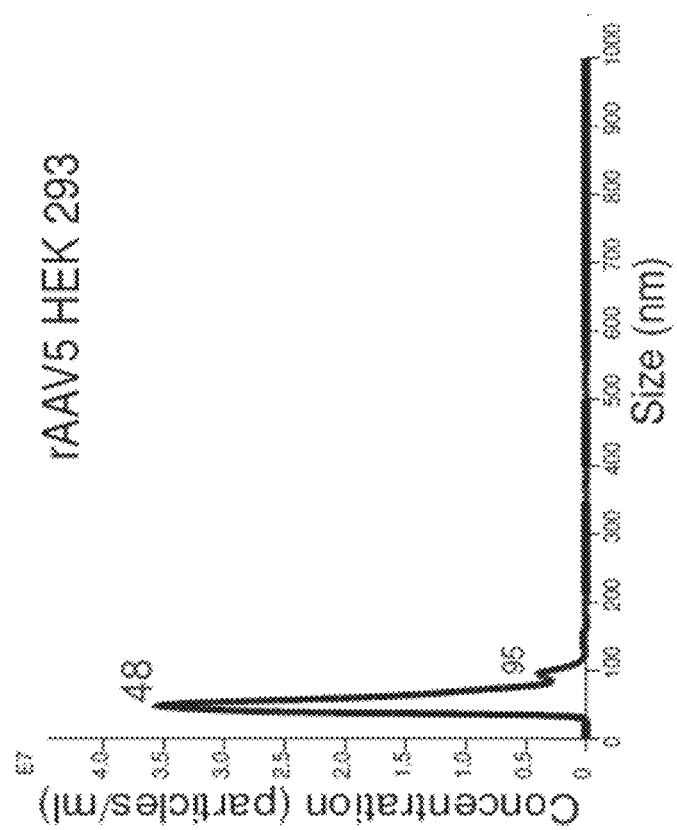

This parameter was investigated to determine whether either of the two manufacturing platforms produces higher ratios of empty particles, a potential source of untoward immune response and a technical challenge during vector purification. rAAV5 and rAAV9 were purified by one-step chromatography over monospecific antibody affinity resins, AVB for rAAV5, and POROS CaptureSelect™ for rAAV9. After purification, the vector genome particle titers were assayed using QC PCR. The total particle titers of rAAV5, and rAAV9 vectors were assayed using Nanoparticle Tracking Analysis (NTA) of rAAV capsids decorated with gold nanoparticles. This approach utilizes the electrostatic attraction between a highly scattering material such as gold nanoparticles and the viral capsid. The resulting gold-labeled virus particles scatter enough light to be visualized and tracked by the optical system (FIGS. 6A-6F), enabling the use of NTA to measure the size and concentration of AAV. Interestingly, while the average sizes of rAAV9 particles for both platforms were identical (major peak of 38 nm, FIGS. 6A, 6B), the average sizes of rAAV5 from HEK 293 and from Sf9 B8 were different (48 nm vs 42 nm, FIGS. 6D, 6E). Of note, these sizes are the approximations of the virus/nano-gold particle complexes, which, in turn, are functions of viral particle charge.

Figure 6C:
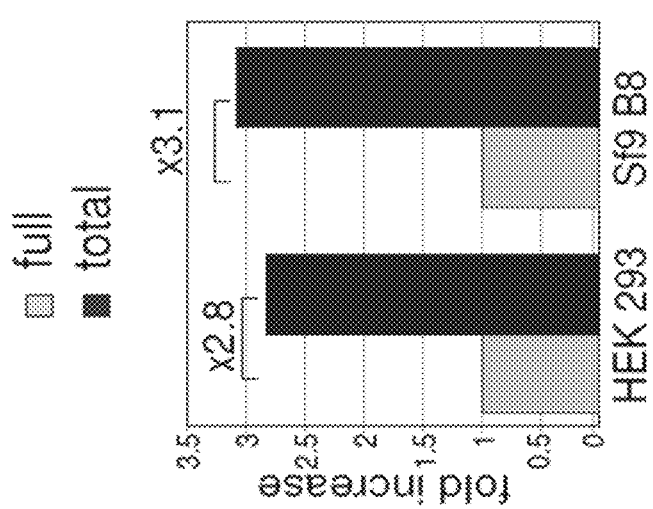
Figures 6E, 6F:
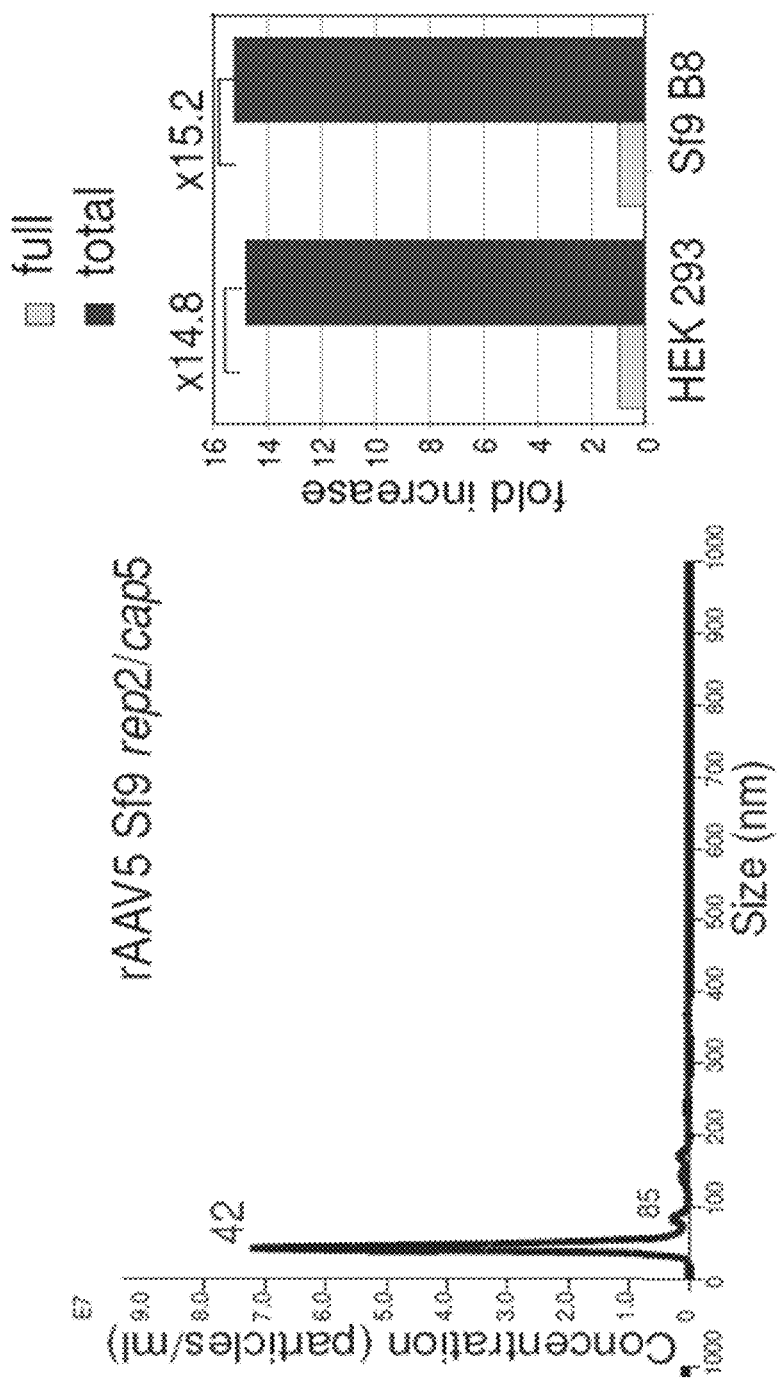

After calculating the ratio of total-to-full particles, these values for HEK 293-derived rAAV9 were 2.8, and for Sf9-derived rAAV9—3.1 (FIG. 6C). Similarly, for rAAV5, the ratios were not significantly different as well: 14.8 vs.15.2 (FIG. 6F). The overall lower ratios for rAAV9, apparently, resulted from the purification bias for CaptureSelect resin chromatography which showed preferential binding of, and enrichment for DNA-containing rAAV9 particles (data not shown).

Transduction Efficiency In Vitro.

Figure 12A:
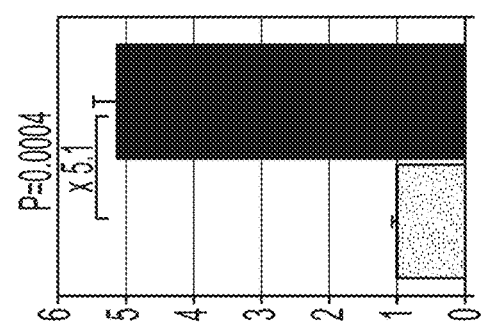
FIGS. 12A-12B depict in vitro transduction assays of rAAV-UF50-BC packaged into rAAV5 or rAAV9 capsids.
Figure 12A:
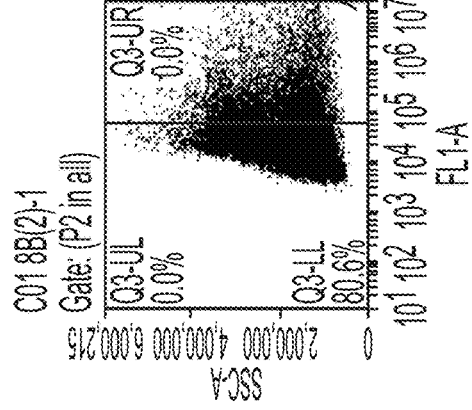
Figure 12A:
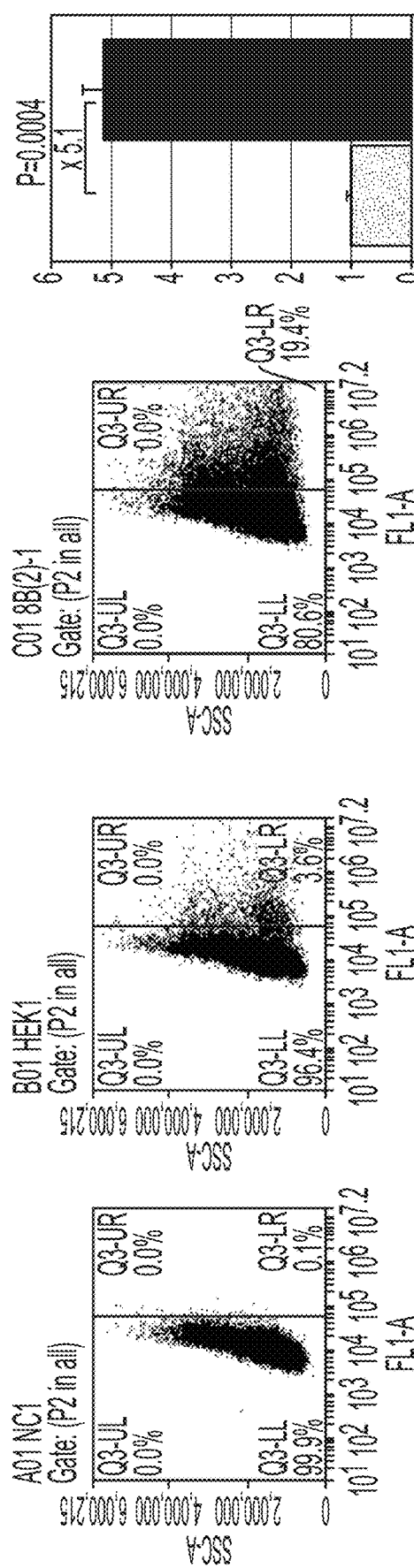
Figure 12B:
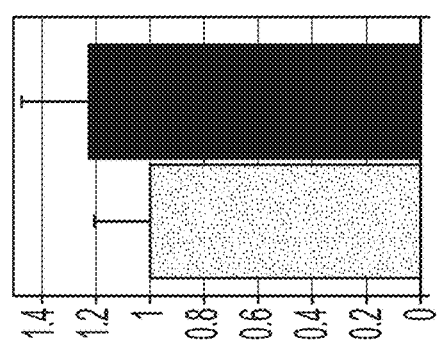
Figure 12B:
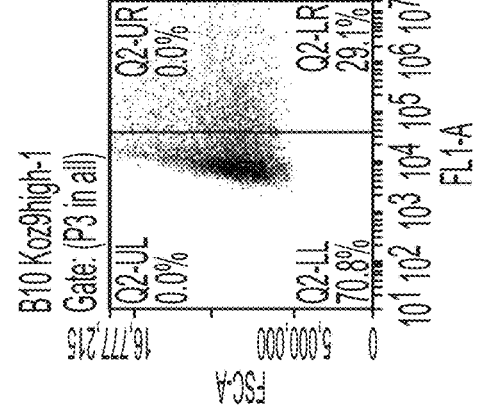
Figure 12B:
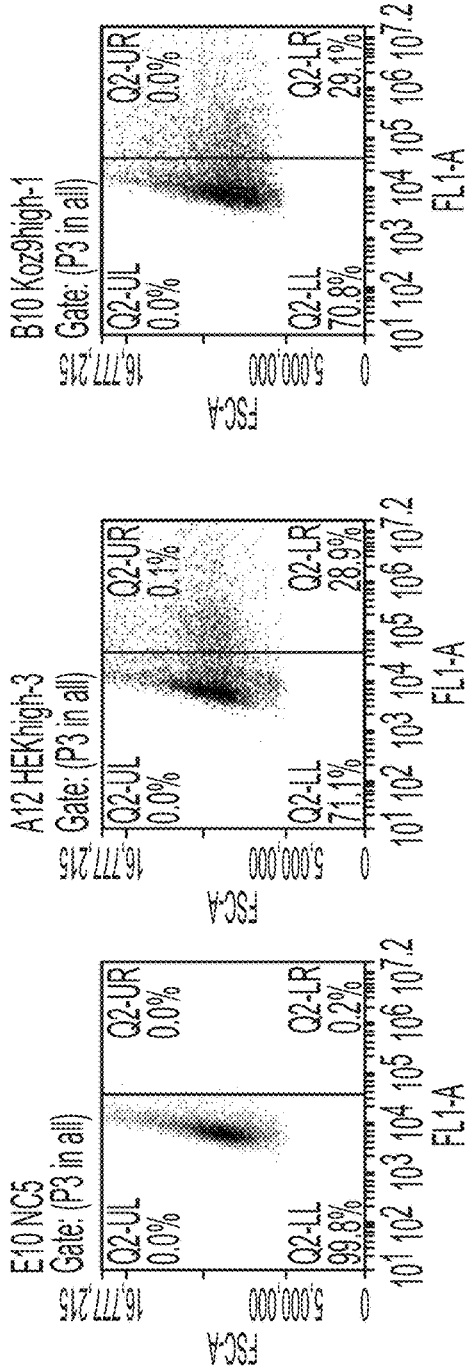

An rAAV transgene cassette incorporating luciferase and mApple reporter genes (FIG. 10B, pTR-UF50-BC[23]) was used to generate the respective BEV to infect the Sf9 B8 cell line to test transduction efficiency. The same plasmid was also used to generate rAAV by a triple plasmid co-transfection of HEK 293 cells. Both rAAV5-Luc-mApple vectors, purified and titered side-by-side, were used to infect a HeLa-derived C12 cell line[24]. FACS analysis (FIG. 12A) revealed significantly higher (~5-fold) transduction efficiency for the Sf9-produced rAAV5 vector. For rAAV9, there was no significant difference between two samples of rAAV9 (FIG. 12B). The data from both experiments are consistent with the protein content.

Figure 16A:
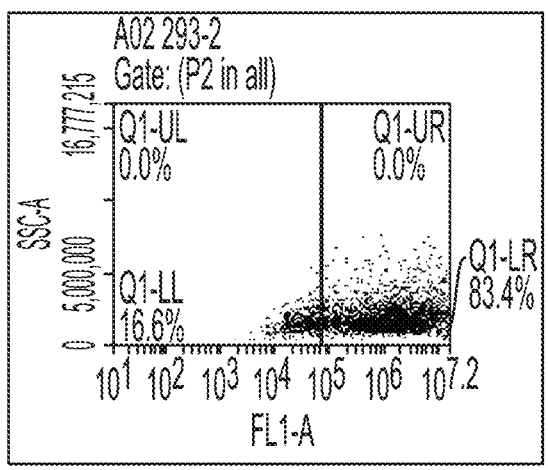
FIG. 16A depicts a dot plot showing the absolute transduction efficiency of rAAV3 particles generated in HEK 293 cells and Sf9 (insect) cells after co-infection with adenovirus serotype 5 (Ad5), as observed after Fluorescence-activated cell sorting (FACS). Cells were infected with rAAVs at an MOI of 5,000. FL1-A represents the fluorescence channel, and SSC-A represents side scatter area.
Figure 16A:
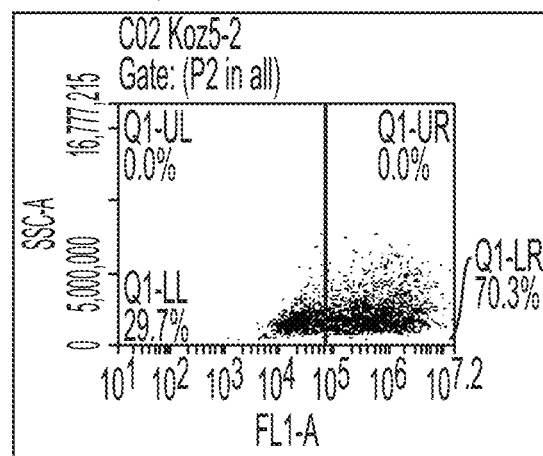
Figure 16A:
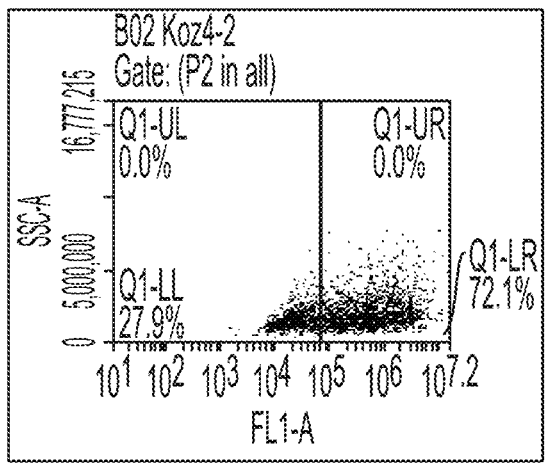
Figure 16A:
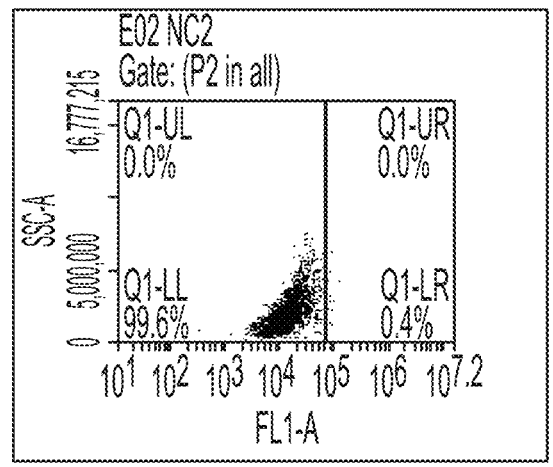
Figure 16B:
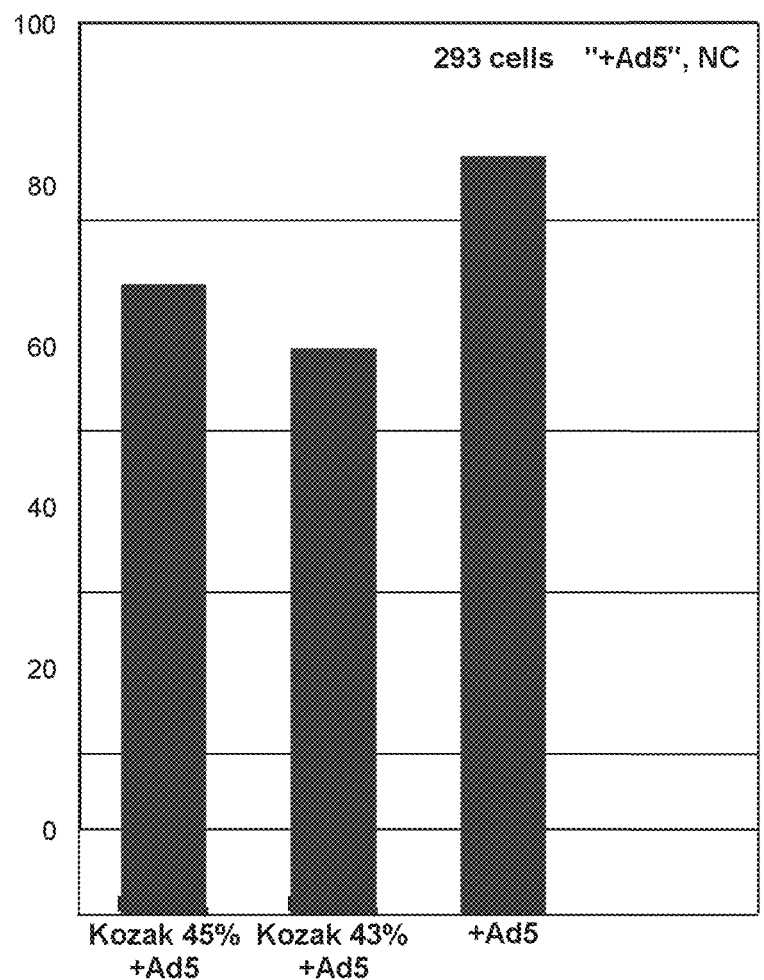
FIG. 16B depicts a bar graph representing the relative transduction efficiency of rAAV3 particles generated in HEK 293 cells and Sf9 cells after co-infection with Ad5.
Figure 17:
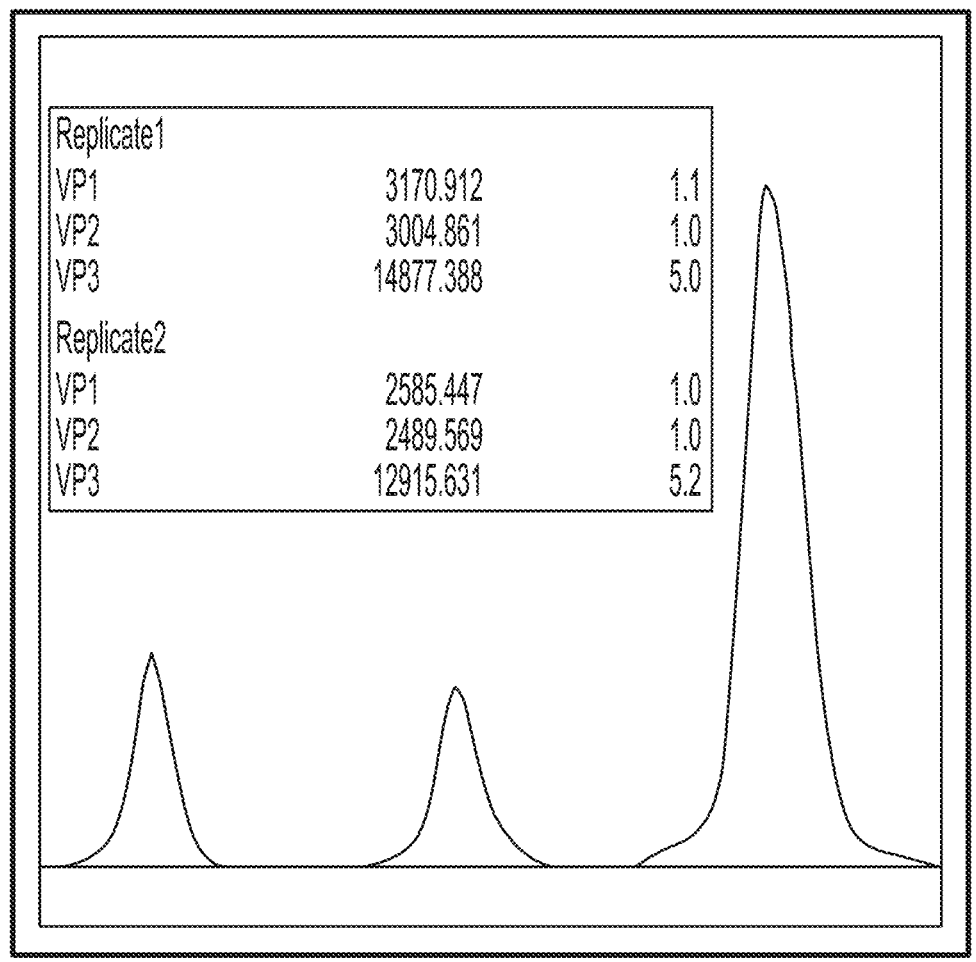
FIG. 17 depicts a histogram showing the relative densities of VP1, VP2 and VP3 protein in replicate rAAV3 particles generated in Sf9 cells. Transduction efficiency was 50%.

In addition, rAAV3-Luc-mApple vectors, purified and titered side-by-side, were used to infect HEK 293 and Sf9 cells. FACS analysis (FIGS. 16A and 16B) revealed a transduction efficiency for the Sf9-produced rAAV3 vector comparable to that in HEK cells. The data is consistent with the protein content. The Sf9-produced rAAV3 particles exhibited enriched levels of VP1 (FIG. 17).

Figure 7A:
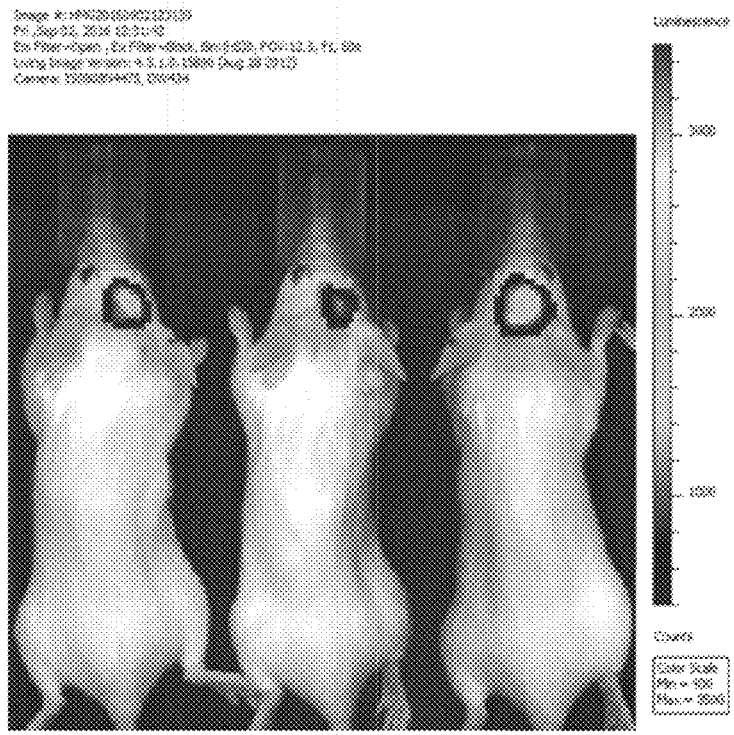
FIGS. 7A-7C depict luciferase and mApple expression after striatal injection of HEK 293- or Sf9 B8-derived rAAV5.
Figure 7A:
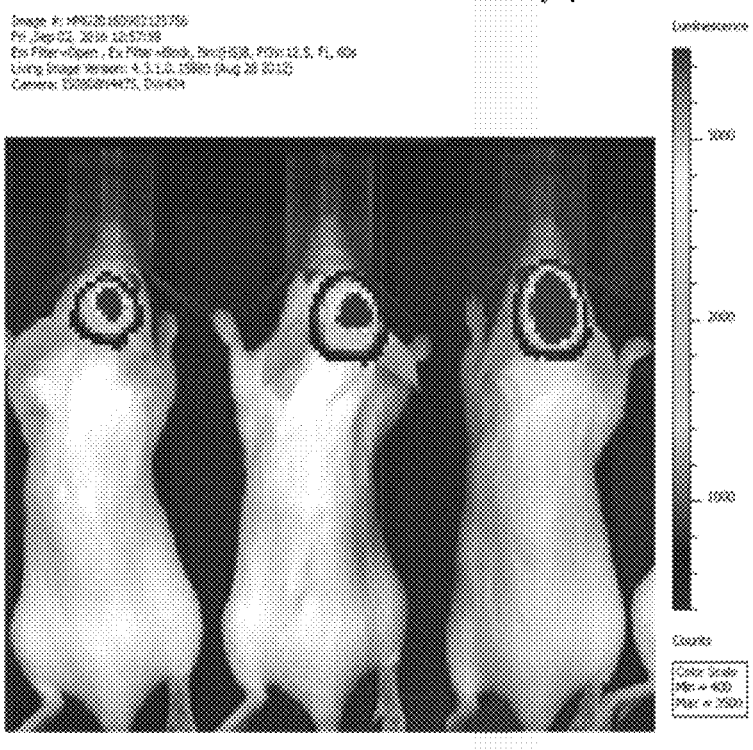
Figure 7B:
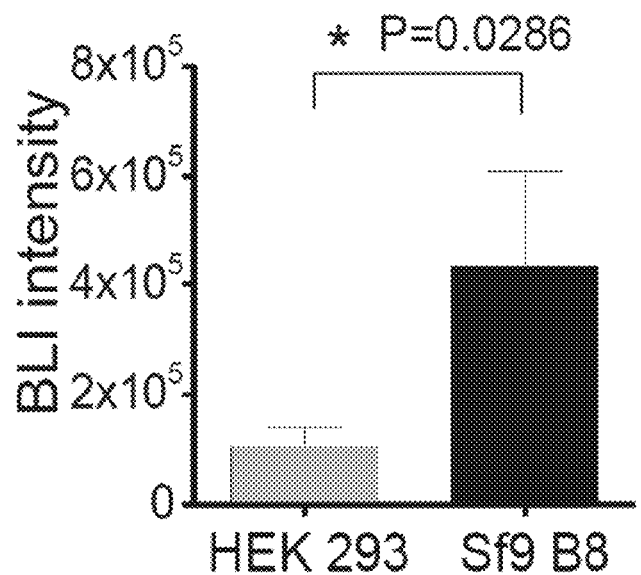
Figure 7C:
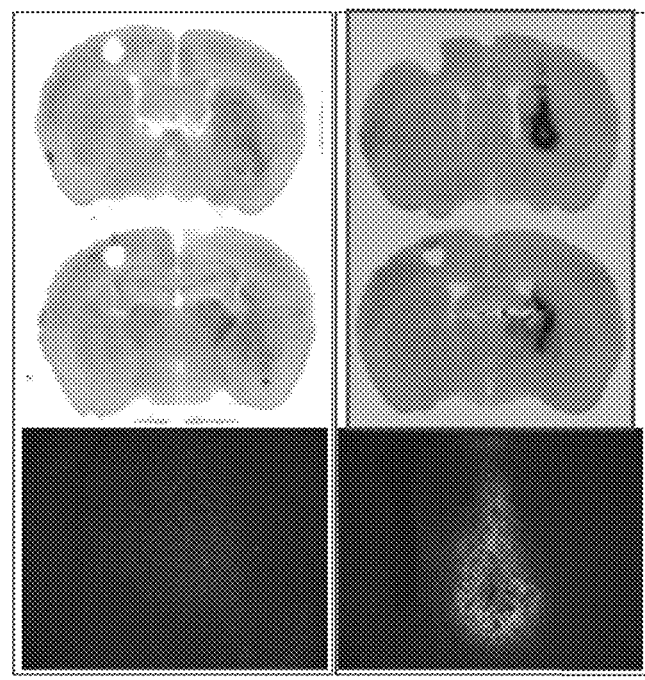

Transduction efficiency in vivo (FIG. 7). rAAV5-LucmApple produced in HEK 293 and Sf9 B8 cells were assayed in vivo in the brain (striatum) of mice. Three weeks post-injection, transduction efficiency was determined by bioluminescence (BLI) (FIG. 7A). Animals injected with Sf9 B8-derived AAV5 showed 4-fold higher BLI signal intensity than HEK 293-derived AAV5 (FIG. 7B, 4.3× $10^5 \pm 1.8 \times 10^5$, and $1.1 \times 10^5 \pm 3.5 \times 10^4$, respectively). Similarly, fluorescent analysis of brain sections revealed a stronger mApple signal in Sf9 B8-derived samples compared to HEK 293 (FIG. 7C).

Next-Generation Sequencing (NGS) Analysis of rAAV5 Vectors Produced in HEK 293 and Sf9 Cells.

Figure 13:
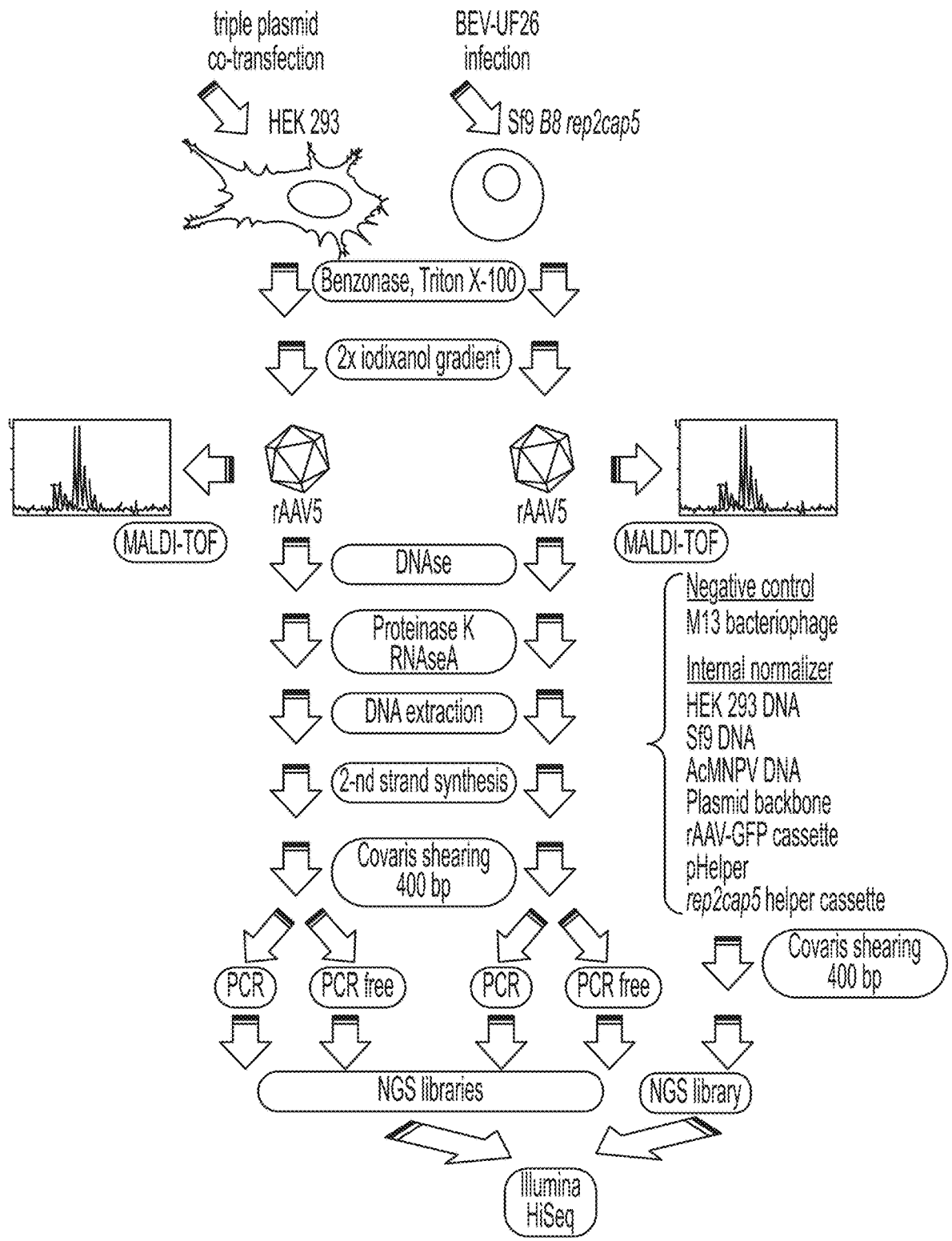
FIG. 13 depicts a non-limiting example of a schematic flowchart of rAAV5 vector DNA preparation for NGS.

Having established an improved OneBac system for the production of higher potency rAAV5-based vectors, a comparative NGS analysis was conducted of the encapsidated ssDNA (pTR-Bac-UF26, FIG. 10A) manufactured by a standard triple co-transfection protocol in HEK 293 cells, or by the single BEV-UF26 infection of a stable rep2cap5 Sf9 cell line B8. The purpose of the NGS analysis was to characterize rAAV cassette-specific, as well as collaterally packaged contaminated DNA species, thus establishing a preferred platform meeting the demands of GMP-grade rAAV vector production. All NGS libraries were prepared, sequenced, and analyzed in duplicates. The general workflow is depicted in a flowchart (FIG. 13). The following parameters have been analyzed.

Collateral Packaging of Contaminating DNA Sequences.

After filtering, the total numbers of reads assigned to an index was 757,433,116. After the alignment of reads to the referenced sequences, the coverage for rAAV cassette reached as high as 2,260,074 reads/nt (nt position 2,000). For collaterally packaged sequences the coverage was significantly lower: 10,781 reads/nt (nt position 1,299, vector backbone), or 6,424 reads/nt (nt position 200, AcMNPV genome).

For both production protocols, the majority of reads were the rAAV-Bac-UF26 cassette which accounted for 96.5% (HEK 293) and 99.4% (Sf9) of all encapsidated DNA sequences (Table 13, FIGS. 8A, 8B). The majority of contaminated DNA in HEK 293 system was bacterial plasmid backbone (2.5%), with lower levels of the rep2/cap5 helper sequences (0.7%), and human genome DNA (0.17%), while the contaminants in the Sf9 preparation were the shuttle plasmid backbone (0.3%), and AcMNPV genome (0.2%). For Sf9-derived rAAV5, no reads were found to be homologous to adventitious rhabdovirus which recently has been isolated from Sf9 cell line obtained from ATCC (Sf-rhabdovirus)[25].

The collaterally packaged sequences were more abundantly represented by the immediate junctions of the rAAV cassette and its respective backbones: bacterial plasmid for HEK 293 cells and baculovirus genome for Sf9 cells. Notably, there was a significant difference, at least ten-fold, in the junction reads coverage between two systems whereby HEK 293 cells appear to encapsidate, at much higher frequencies, bacterial plasmid backbone sequences which are more distant from both the left and right AAV terminal repeats (FIGS. 8C, 8D). Thus, analysis of contaminating DNA sequences suggests that OneBac system delivers better precision and provides higher quality rAAV vectors whereupon only 0.6% of the encapsidated vector genome incorporates foreign DNA as opposed to 3.5% for HEK 293 cells.

TABLE 13

Analysis of specific and collateral packaging of rAAV5-UF26 in HEK 293 and Sf9 cells*

| | HEK 293 | | | Sf9 | |
|---|---|---|---|---|---|
| Reference genome | NGS library | | Reference genome | NGS library | |
| | PCR free | PCR | | PCR free | PCR |
| UF26cassette | 96.50 | 95.24 | UF26 cassette | 99.44 | 99.25 |
| | 96.59 | 95.38 | | 99.45 | 99.29 |
| Vector backbones | 2.58 | 3.49 | Vector backbone | 0.30 | 0.42 |
| | 2.52 | 3.39 | | 0.30 | 0.42 |
| pHelper | 0.04 | 0.04 | AcMNPV | 0.22 | 0.29 |
| | 0.04 | 0.04 | | 0.21 | 0.25 |
| rep2cap5 | 0.71 | 1.00 | cap5 | 0.009 | 0.002 |
| | 0.68 | 0.97 | | 0.009 | 0.002 |
| | | | rep2 | 0.005 | 0.001 |
| | | | | 0.006 | 0.001 |
| H. sapiens | 0.17 | 0.22 | S. frugiperda | 0.026 | 0.040 |
| | 0.17 | 0.22 | | 0.025 | 0.041 |

*Relative content of DNA in purified virions is shown as percentage of total sequences identified by NGS analysis. All NGS analyses were conducted in duplicates shown for each reference genome in two parallel rows.

rAAV Genome Coverage.

Using a standard protocol, which included only eight cycles of PCR amplification step to generate NGS libraries, several sequences were identified within the CBA promoter and the downstream intron displaying at least ten-fold lower sequencing coverage compared to the rest of the rAAV cassette. Close examination revealed that these sequences are extremely GC-rich (FIGS. 8A, 8B). This relatively low coverage might have reflected the lower representation of these sequences in the packaged virions because of truncation during DNA replication. Alternatively, this drop represented an artifact introduced by PCR-related NGS library preparation. To exclude the second possibility NGS libraries were prepared directly from the purified encapsidated rAAV DNA without PCR amplification. This way, the coverage of the sequences in question was restored to levels comparable to the rest of the cassette. Thus, both HEK 293 and Sf9 cells support packaging of full-length rAAV cassettes with little if any evidence of truncation.

Genomic Identity of rAAV-Bac-UF26 Cassette.

Figure 9A:
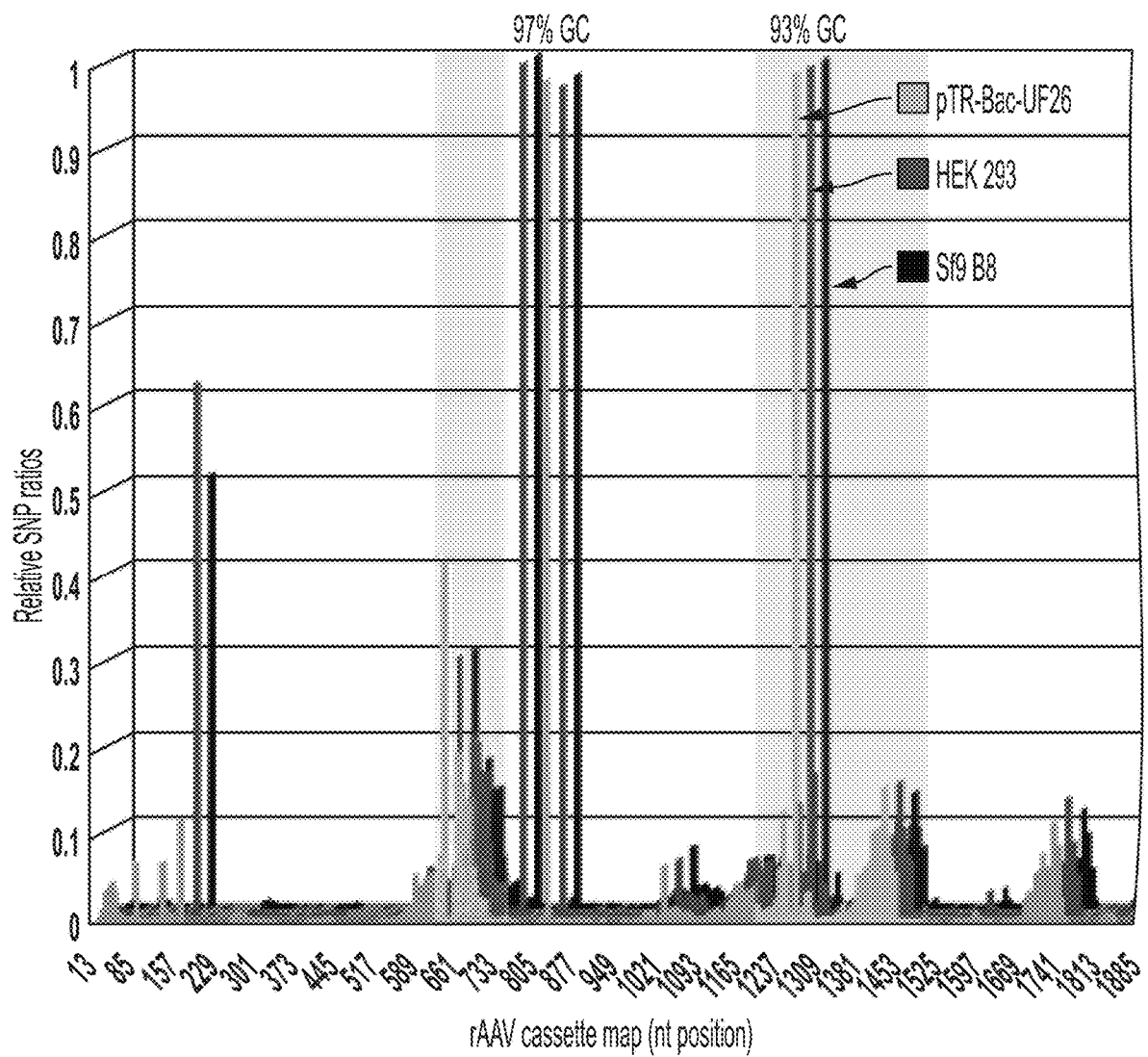
FIGS. 9A-9C show the distribution of SNPs identified in rAAV5-Bac-UF26 cassette encapsidated by HEK 293 vs.
Figure 9B:
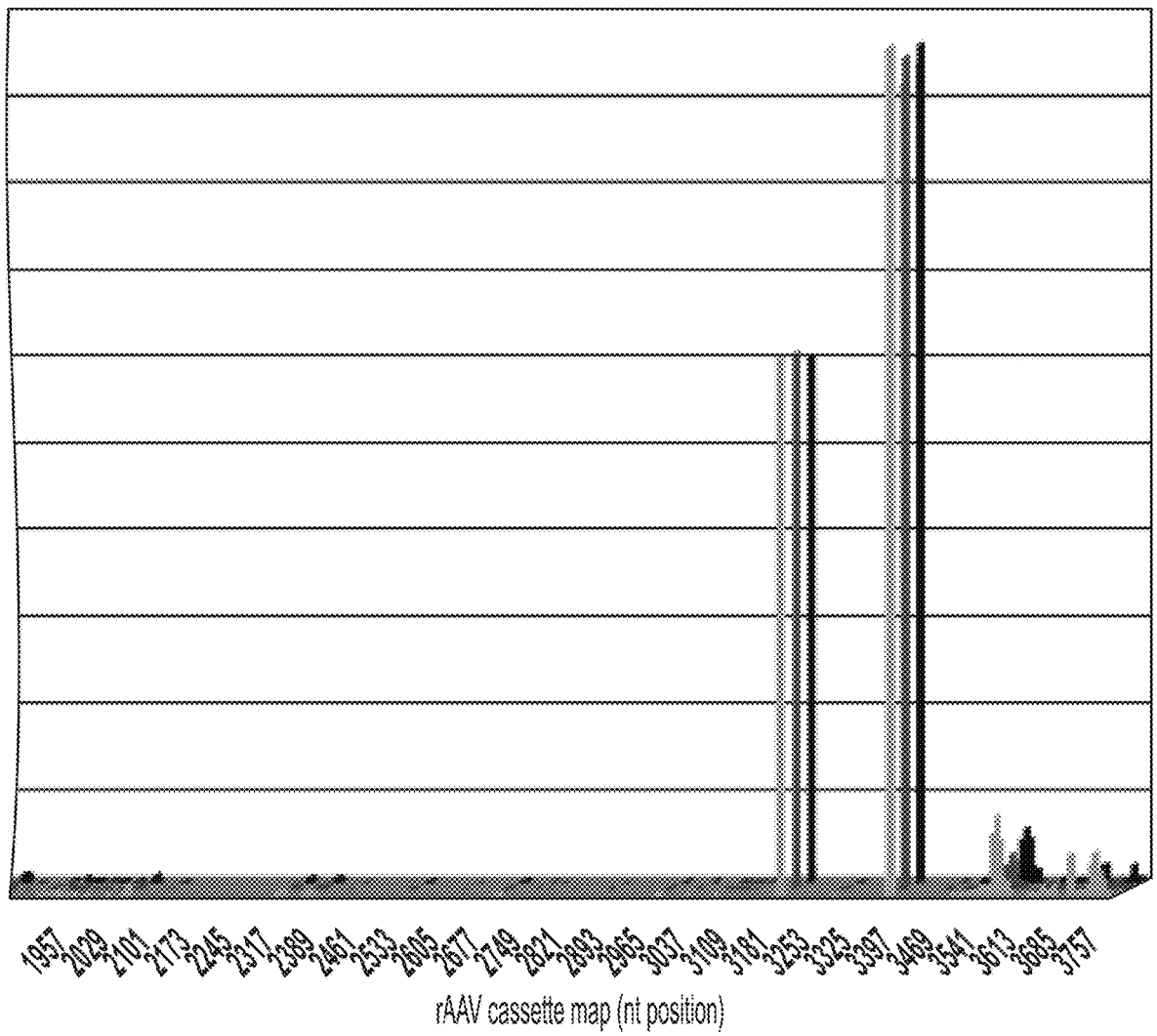
Figure 9C:
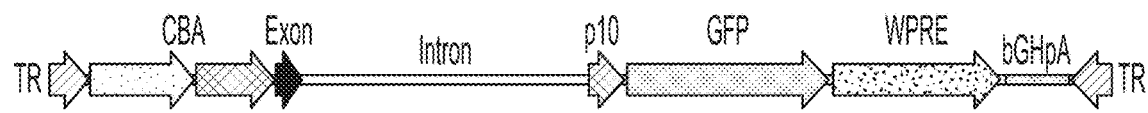

The high sequencing depth of AAV cassette allowed for the detailed analysis of the packaged DNA sequence identity and correlation to its respective parent bacterial plasmid. To reduce the probability of false calls and to increase the confidence of single nucleotide polymorphism (SNP) analysis, only PCR-free samples NGS data were utilized. SNP variants for DNAs from both viral samples, as well as positive control plasmid sample, displayed very similar profiles of substitutions (correlation coefficient of 0.75-0.77) (FIGS. 9A-9B). Interestingly, the majority of SNPs were co-localized with non-coding sequences identified above as regions enriched in GC content (FIG. 9C): chicken β-actin promoter and the intron sequence. In addition, and consistent with Lecomte et al.[26], AAV TRs displayed relatively high SNP variability.

The relatively inferior potency of insect cells-manufactured rAAV vectors of AAV5 and AAV8 serotypes was previously documented by Urabe et al.[10] and Kohlbrenner et al.[9] Subsequently, it was shown that many other OneBac-derived AAV serotypes were characterized by lower infectivity compared to 293-derived AAVs[27]. The unifying cause for all affected serotypes was the modified sequence of a capsid helper gene resulted in lower content of VP1 capsid protein incorporating phospholipase A2 activity. As expected, the recommended solutions were aimed at alleviating this problem by using a different initiation codon CUG[11] or artificial intron[8,12]. Even though new designs helped to increase the infectivity for some vectors, the solutions appeared to lack flexibility necessary for a serotype-specific sequence adjustment.

A new approach is described herein to increase relative VP1/VP2 content of a capsid. This is accomplished by modifying a canonical Kozak sequence preceding VP1 AUG start codon. As a proof of principle, a range of Kozak sequences were tested for AAV5 and AAV9 serotypes showing that the most favorable translation initiation sites were serotype-specific producing rAAV vectors which exceeded transduction efficiencies of HEK 293-derived counterparts. The described approach, however, requires fine adjustment of VP1 Kozak sequence in the narrow window of relative TIS efficiencies which also varies for different serotypes. One of the reasons for this variation is that the VP1:VP2:VP3 ratios depend not only on VP1 TIS relative efficiency, but also on the ones of VP2 and VP3 TISs which are also different for all serotypes (Table 14). Moreover, intentionally increasing VP1 content above certain threshold (e.g., FIG. 4B, lanes 1 and 6) appears to be counterproductive as the yield of the virus drops precipitously once the VP1:VP2:VP3 ratio shifts too far away from the theoretical value of 1:1:10. One can derive a 'consensus' VP1TIS: U(C)A(C/G)U(G)UG(U)UAUGG (SEQ ID NO: 72) with the understanding that the specific TISs for particular uses may be identified empirically.

TABLE 14

Translation initiation sequences surrounding VP1, VP2, and VP3 start codons in AAV serotypes

| AAV serotype | VP1 ORF | | | VP2 ORF | | | VP3 ORF | | |
|---|---|---|---|---|---|---|---|---|---|
| | up | Kozak TIS, % | down | up | Kozak TIS, % | down | up | Kozak TIS, % | down |
| 1 | CCAGGT | ATG (130) | GC | GCTAAG | ACG | GC | ACTACA | ATG (115) | GC |
| 2 | TCAGGT | ATG (133) | GC | GTTAAG | ACG | GC | AATACG | ATG (114) | GC |
| 3 | CCAGGT | ATG (130) | GC | GCTAAA | ACG | GC | AATACA | ATG (108) | GC |
| 4 | CCAGAT | ATG (99) | AC | GGTGAG | ACG | GC | AGTGAG | ATG (80) | CG |
| 5 | GTAGTC | ATG (91) | TC | GCTAAG | ACG | GC | GATACA | ATG (114) | TC |
| 6 | TTTAAA | ATG (126) | GC | GCTAAG | ACG | GC | ACTACA | ATG (115) | GC |
| 7 | CCAGGT | ATG (130) | GC | GCTAAG | ACG | GC | GGTACA | GTG* | GC |
| 8 | CCAGGT | ATG (130) | GC | GCTAAG | ACG | GC | AATACA | ATG (108) | GC |
| 9 | TCAGGT | ATG (133) | GC | GCTAAG | ACG | GC | CTTACA | ATG (129) | GC |
| 10 | CCAGGT | ATG (130) | GC | GCTAAG | ACG | GC | GGTACA | ATG (113) | GC |
| 11 | CCAGGT | ATG (130) | GC | GCTAAA | ACG | GC | ATTGAA | ATG (81) | CG |

*designates a putative alternative initiation codon VP3 in AAV7 deduced by sequences alignment of AAV serotypes capsid genes. The relative strength of Kozak TIS is expressed in % next to the initiation codon[18]

In the rAAV5 construct selected for the analysis, the numerical value of the relative VP1 content was increased from 0.2-0.4 in HEK 293-derived vector (by two independent assays) to 0.7-1.1 in Sf9 cells (i.e., increased by 3 fold on average). For VP2, these values increased from 0.5 to 1.7, a similar 3-fold increase. A concurrent increase of VP2 was one of the unpredicted effects of the relative increase of rAAV5 VP1. The N-termini of both VP1 and VP2 incorporate the so-called basic region 3 (BR3, PKRKKART (SEQ ID NO: 73)) representing conservative nuclear localization sequence (NLS) motif which is useful for AAV to deliver its genome within the nucleus and subsequently transduce the cells[28-30]. It is thus not surprising that a 3-fold increase of each VP1 and VP2 increases the yield of a more infectious virus.

The data provided above does not include direct comparison of rAAV5 and rAAV9 manufactured in recently described OneBac2.0[8] and the current system. However, one can relate the respective capsid ratios and conclude that for these serotypes, the newly designed cap helper genes significantly improved both AAV5 and AAV9 capsid stoichiometry, which translate into higher potency viral vectors.

Another unexpected finding was the similarity of packaging efficiencies displayed by HEK 293 and Sf9 cells which were assessed by a surrogate parameter of full-to-empty particles ratios. Using the previously identified ratio of rep/cap expression cassettes of 1:2.5 to construct a stable producer cell line[7], similar to HEK 293 packaging efficiency was achieved.

With many clinical trials under way, assessing the genetic identity of rAAV stocks manufactured by different protocols becomes a pressing regulatory issue. Many groups have reported a collateral encapsidation of sequences derived from packaging host cells 26, 31, 32, bacterial helper plasmid backbones[26, 33], helper viruses[8, 32], and wt AAV rep/cap sequences[26, 34]. To evaluate the genetic identity of the packaged rAAV cassette NGS analysis of encapsidated single-stranded viral DNA was conducted. The pilot analysis showed uneven sequence coverage of the cassettes in the GC-enriched sequences which were almost identical for both platforms. Utilizing PCR-free protocol, it was shown that the drop of coverage apparently resulted from the PCR-induced artifacts during libraries preparation and not from packaging of the truncated rAAV genomes[35, 36]. The accuracy of PCR-based methods for NGS libraries preparations were questioned by several groups as not appropriate for AAV-related analysis[37] especially in GC-rich palindromes such as inverted terminal repeats (ITRs), or applied for any GC-enriched sequence[38]. Consequently, NGS analysis of rAAV vector preparations should be carried using adequate protocols.

Analysis of the genetic identity of the viral DNA derived from both platforms showed no significant differences between the encapsidated rAAV DNA in insect vs human cells. Of note, however, is a fact of a documented here deviation of the sequence of the pTR-Bac-UF26 plasmid DNA pool used to transfect HEK 293 cells, from the sequence of this plasmid in the database. The fact of such genetic drift of a plasmid DNA, while surprising, can be explained by the following mechanism. rAAV cassettes-containing plasmids are propagated in recombination-deficient strains of E. coli to maintain the integrity of AAV ITRs. These strains lack components of pathways (endA, recB recJ) that catalyze rearrangement and deletion of nonstandard secondary and tertiary structures. As a result, plasmid DNA accumulates mismatched bases and point mutations which otherwise would be restored by the mismatch repair system. Mismatches in DNA, if not repaired, result in a high spontaneous mutation frequency. Therefore, during transfection, mutated plasmid DNA carries its heteroduplex "imprinted" structure over into host HEK 293 cell nuclei, where it is either repaired[39] or replicated copying the mutation. Thus, the plasmid DNA pool in a co-transfection protocol carries over some of the mutagenesis burden of E. coli into encapsidated AAV cassettes which could be substantial for some GC-rich sequences. Interestingly, the GFP reporter cDNA appears to have a minimal number of mutations (FIG. 8A), which could reflect its synthetic "humanized" origin[40]. In this regard, depleting CpG motifs from rAAV cassettes, in addition to its immunogenicity-related effects[41], might also help to increase genetic stability of a parent plasmid DNA.

Direct side-by-side NGS analysis of rAAV cassettes manufactured by the two platforms revealed, unexpectedly, higher precision of viral DNA packaging in insect cells, encapsidating considerably less contaminating DNA (0.6% vs 3.5%). This 6-fold reduction appears to be significant if one takes into account that FDA guidelines state "that the level of residual cell-substrate DNA should be ≤10 ng per dose" (fda.gov/downloads/AdvisoryCommittees/CommitteesMeetingMaterials/BloodVaccinesandOtherBiologics/VaccinesandRelatedBiologicalProductsAdvisoryCommittee/UCM319573.pdf).

Considering current clinical trials with rAAV whereupon the doses reached as high as $6\times10^{13}$ vg/kg[42,43] the vector, if produced in HEK 293 cells, would incorporate amounts of contaminating DNA that would exceed FDA guidelines. Here, it was shown that rAAV5 vectors produced using the OneBac system are significantly more infectious and, at the same time, encapsidate less amount of foreign DNA. Therefore, this method of production improves the potential therapeutic outcome of the vector administration by reducing its effective dose and advancing safety.

Materials and Methods

The following non-limiting materials and methods were used in connection with certain experiments described in this application. These or other materials and methods can be used in connection with embodiments described in this application.

rAAV5 and rAAV9 Production in HEK 293 Cells

Both rAAV5 and rAAV9 vectors were produced by a triple co-transfection procedure as described previously[44]. Plasmids harboring rAAV cassettes (rAAV5-Bac-UF26, or rAAV5-UF50-BC, as well as rAAV9-Bac-UF26, FIGS. 10A-10B) were used in combinations with pHelper and pRep2Cap5 (or pRep2Cap9) at a 1:1:1 molar ratio. Both rAAV5 and rAAV9 were purified using sequential double rounds iodixanol buoyant density centrifugations. Specifically, the first round iodixanol fraction containing full particles was diluted with 1×PBS-MK buffer 2.5-fold and used in lieu of 15% iodixanol-1 M NaCl step in a standard gradient[44].

rAAV5 and rAAV9 Production in Sf9 Cells

Bac-UF26, or UF50-BC rAAV cassettes were inserted into pFastBac backbone and the respective BEVs were derived following Bac-to-Bac system guidelines. Plaque-purified BEVs were propagated to P3, titered by a plaque assay, and used to infect Sf9-based stable cell lines harboring rep2cap5, or rep2cap9 inducible helper genes, as described previously[7]. Upon harvesting, freeze-thaw lysates were treated with benzonase and clarified by a high-speed centrifugation at 20,000 g for 30 min. Supernatants were purified as described above for 293 HEK-manufactured AAV.

One Step Purification of rAAV5 and rAAV9.

rAAV5 was purified from clarified crude lysate using AVB Sepharose High Performance affinity chromatography resin (GE Healthcare), as described previously[45]. rAAV9 was purified by one step affinity chromatography using POROS CAPTURESELECT™ AAV9 resin (Thermo Fisher) from a crude lysate. Specifically, a clarified crude lysate was applied under gravity to a column containing 0.5 ml resin, the column was then washed with 10 column volumes of 1×PBS, followed by 1 ml elution buffer: 50 mM citrate buffer pH 3.0-1 M NaCl. The eluted rAAV9 was immediately neutralized by 0.1 ml 1 M TrisHCl pH 8.4.

rAAV Titering

Direct comparative analysis of rAAV vectors requires an accurate estimate of the respective viral titers. Four independent assays were used to titer rAAV derived from HEK 293 or Sf9 cells: 1) Droplet Digital PCR (ddPCR)[46]—to establish a reference standard, using BioRad QX200 Digital PCR System; 2) quantitative competitive PCR (QC-PCR) using iTaq™ Universal SYBR® Green Supermix kit (Bio-Rad, 1725121) and qPCR BioRad CFX Connect RealTime System; 3) a picogreen-based protocol[47], and 4) Nanoparticle Tracking Analysis (NTA) using NanoSight 300 (NS-300, Malvern Instruments, Malvern, UK)—to quantify the titer and the size of rAAV particles. After establishing the conditions of each protocol, and using a reference standard derived by ddPCR, the calculated titers from protocols 2) and 3) were always within a factor of 2, and were averaged to derive the working titers. Briefly, the following procedures were followed.

ddPCR. A set of dilutions, in triplicates, in the range of $1-10^3$ viral genome copies per reaction was prepared using 1×Lactate Ringer (LR) solution supplemented with 0.05% Pluronic F-68. DdPCR was carried out using the following primers: TM_CMV_F 5'-ATAGGGACTTTCCAT-TGACGTC-3' (SEQ ID NO: 74), TM_CMV_R 5'-TGATA-CACTTGATGTACTGCCAAG-3' (SEQ ID NO: 75), TM_CMV_Probe FAM 5'-TGGGTGGACTATT-TACGGTAAACTGCC-3' BHQ (SEQ ID NO: 76).

QC-PCR.

To derive a standard curve, rAAV-UF26 transgene cassette was gel-purified after SmaI digestion of the respective plasmid pTR-Bac-UF26. The recovered DNA was diluted to the approximate concentration of 1 ng/μl and the precise concentration was determined by QUBIT dsDNA assay. Direct QC-PCR titering of highly purified Sf9- or HEK 29-produced rAAV were performed with the same primers set and using the standard curve prepared by 10-fold serial dilutions of a reference rAAV sample (ddPCR), and the gel-purified rAAV cassette (QC-PCR).

PicoGreen-based assay was conducted by Quanti-iT PicoGreen dsDNA Assay kit (Life Technology, P7589), using Lambda DNA standard to calibrate the standard curve as described[47]. Optical density was measured by Perkin Elmer 1420 Multilabel Counter Victor V.

NTA.

Prior to the NTA analysis, the titers of the viral stocks were assessed by PAAG gel electrophoresis. Knowing approximate titers, 50 μl of AAV stock diluted in LR buffer were added to a labeling mix containing labeling buffer (20 mM Citric acid, pH 3.5, 0.1% Pluronic F68, 1 mM NaCl) and gold nano-particles (Sigma, Cat. #741949). After 30 min incubation at RT, gold-labeled AAV was diluted by the labeling buffer to a final concentration of $5\times10^8$-$3\times10^9$ particles/mL. Labeling mix without AAV and AAV in the labeling buffer without gold was used as a negative control. Measurements were carried out using an NS-300 instrument with the following settings: Laser Type—Blue488, camera level—15, number of frames—749, time of recording—30 sec, number of records—3 per each data point. At least four data points generated by NS-300 were used to calculate an AAV titer.

MALDI-TOF.

VP1, VP2, and VP3 bands were cut out from SDS-PAGE and prepared for trypsin digestion. Capsid proteins were digested in gel slices with sequencing grade trypsin from Promega (Madison Wis.) using a manufacturer recommended protocol. Briefly, bands were trimmed as close as possible to minimize background polyacrylamide material. Gel pieces were then washed in nanopure $H_2O$ for 5 min. The wash step was repeated twice followed by two cycles of de-staining with 1:1 v/v methanol:50 mM ammonium bicarbonate for 10 min each cycle. The gel pieces were dehydrated with 1:1 v/v acetonitrile:50 mM ammonium bicarbonate. The gel slices were rehydrated and incubated with dithiothreitol (DTT) solution (25 mM in 100 mM ammonium bicarbonate) for 30 min prior to the addition of 55 mM Iodoacetamide in 100 mM ammonium bicarbonate solution. Iodoacetamide was incubated with the gel slices in darkness for 30 min. Gel slices were washed again with two cycles of $H_2O$ and dehydrated with 1:1 v/v acetonitrile:50 mM ammonium bicarbonate. The protease was driven into the gel pieces by rehydrating them in 12 ng/ml trypsin in 0.01% ProteaseMAX Surfactant for 5 min. The gel piece was then overlaid with 40 μL of 0.01% ProteaseMAX surfactant:50 mM ammonium bicarbonate and gently mixed on a shaker for 1 hr. The digestion was stopped by addition of 0.5% TFA. MS analysis was either immediately performed to ensure high quality tryptic peptides with minimal non-specific cleavage or samples were frozen at −80° C. until they could be analyzed. The $^{18}O$-labeled digest was performed the same way except the ProteaseMAX Surfactant, and trypsin was prepared in $H_2^{18}O$. In order to prevent back exchange, trypsin was inactivated by incubation at 100° C. for 15 min. VP3 was digested using $H_2^{18}O$ while VP1 was digested in regular $H_2^{16}O$; the digestion products mixed 1:1 and analyzed by MALDI-TOF. A similar analysis was conducted for VP2/VP3 as well.

MALDI-TOF was performed on a Bruker Daltonics Microflex LRF mass spectrometer (Bruker Daltonics, Breman, Germany) operated in reflectron, positive ion mode with a N2 laser. Laser power was used at the threshold level required to generate signal. The instrument was calibrated with Peptide Calibration Standard II (Bruker Daltonics) which is a mixture of Angiotensin II, Angiotensin I, Substance P, Bombesin, ACTH clip 1-17, ACTH clip 18-39, Somatostatin 28, Bradykinin Fragment 1-7, Renin Substrate Tetradecapeptide porcine with a covered mass range ~700 Da-3200 Da. α-cyano-4-hydroxycinnamic acid was used as the matrix and prepared as a saturated solutions in 50% ACN/0.1% TFA (in $H_2O$). Allotments of 1 μL of matrix and 1 μL of sample were thoroughly mixed together; 0.5 μL of this was spotted on the target plate and allowed to dry.

In Vitro Transduction Assay.

rAAV5-Bac-UF26 and rAAV9-Bac-UF26 were assayed using C12 cells[24] infected with rAAVs at an MOI of 2,000 and co-infected with Ad5 at an MOI of 5. Forty eight hours after infection, cells, positive for mApple fluorescence, were scored by Fluorescence-activated cell sorting (FACS).

AAV Injections

All animal procedures were approved by the University of Florida Institutional Animal Care and Use Committee. Four-five week old female BALB/c (The Jackson Laboratory, Bar Harbor, Me. USA) mice were used for the experiments. All surgical procedures were performed using aseptic techniques and isoflurane gas anesthesia. Brain surgeries were performed as previously described[23]. Briefly, once anesthetized, mice were placed in the stereotactic frame (Kopf Instruments, Tujunga, Calif.), and 2 μl of either HEK- or 8B-derived rAAV5-UF50-BC vectors (4.75×1011 vg/ml) were injected into the right striatum (coordinates: anterior-posterior—0.3 mm, lateral—2.0 mm, dorsoventral—3.0 mm), through a glass micropipette with an inner diameter of 30-40 μm at a rate of 0.5 μl/minute. The needle was left in place for 5 min prior to withdrawal from the brain.

Bioluminescence Imaging

Mice were imaged as previously described[23]. Twelve minutes after intraperitoneal injection of D-luciferin (15 mg/mL in PBS, 126 mg luciferin/kg body weight), bioluminescence measurements were obtained from region-of-interest analysis using a Xenogen IVIS Lumia in vivo imaging system (PerkinElmer, Waltman, Mass.). Three mice were imaged at the same time with a field of view of 25 cm. An imaging time of 60 sec with medium binning and an f-stop of 1 were used for the camera settings. The images displayed in each data set were normalized to the appropriate color intensity scale. The BLI data are reported as raw data, as the total number of counts reaching the charge-coupled device detector.

Brain Tissue Preparation and Fluorescence Imaging

Mice were deeply anesthetized with pentobarbital (Beuthanasia-D) and perfused through the ascending aorta with 10 ml of saline solution, followed by 10 ml of ice-cold 4% paraformaldehyde (PFA) in 0.1 M phosphate buffer, pH 7.4. Brains were removed and post-fixed overnight at 4° C. in 4% PFA. Sixty micrometer-thick coronal sections were cut on a vibratome stage VT1000 S (Leica Microsystems, Wetzlar, Germany). mApple fluorescence was analyzed by a variable mode laser scanner (Typhoon 9200, GE Amersham, Pittsburgh, Pa., USA) or using inverted microscope DMI4000 B (Leica Microsystems, Wetzlar, Germany).

NGS Analysis

NGS was performed by UF ICBR Core using HiSeq 3000 instrument (Illumina, San Diego, Calif.) and paired-ended sequencing. To demonstrate the reproducibility of selected NGS protocols, all DNA samples were prepared in duplicates. Similarly, all steps of NGS library synthesis, sequencing, and bioinformatics were conducted in parallel and in duplicates.

The referenced DNA for HEK 293-based production included all DNA sequences which could potentially contaminate rAAV stock: H. sapiens genome sequence (HEK 293, GRCh38.p9, ncbi.nlm.nih.gov/assembly/GCF_000001405.35 or RefSeq assembly accession: GCF_000001405.35); Adenovirus helper plasmid (pHelper, GenBank: AF369965.1); pACGr2c5 encoding AAV2 Rep and AAV5 VP proteins (rep2cap5), and the respective plasmid backbones. For Sf9-based production, the following sequences were analyzed: S. frugiperda genome (JQCY02.1.fsa_nt.gz, GenBank: JQCY00000000.2); AcMNPV genome (GenBank NC_001623.1); S. frugiperda rhabdovirus isolate Sf (GenBank KF947078.1); FastBac shuttle plasmid backbone, and sequences encoding AAV2 Rep and AAV5 VP.

Figure 14A:
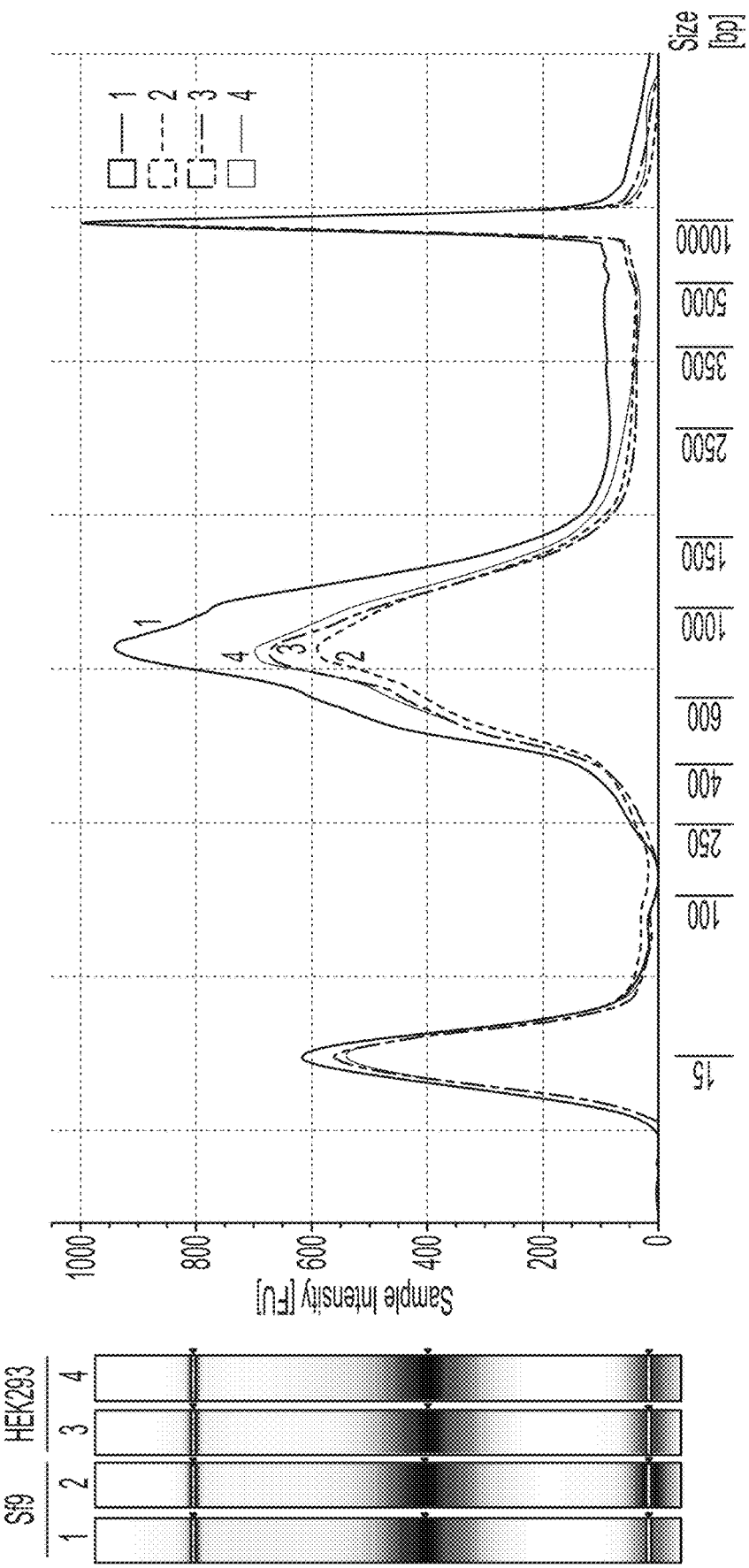
FIGS. 14A-14C depict distributions of NGS libraries of DNA fragment sizes. Analysis of the NGS libraries was performed by High Sensitive D5000 ScreenTape.
Figure 14B:
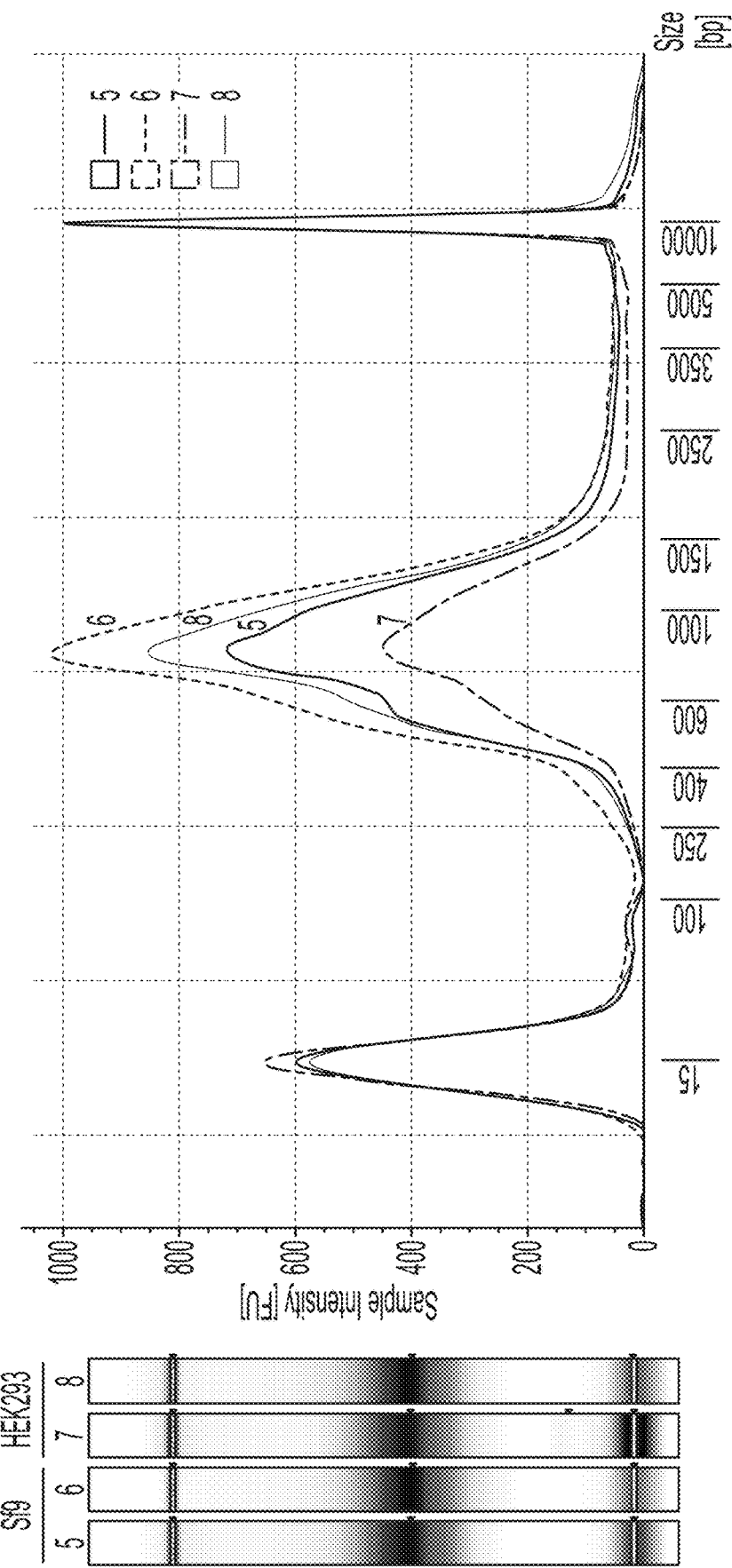
Figure 14C:
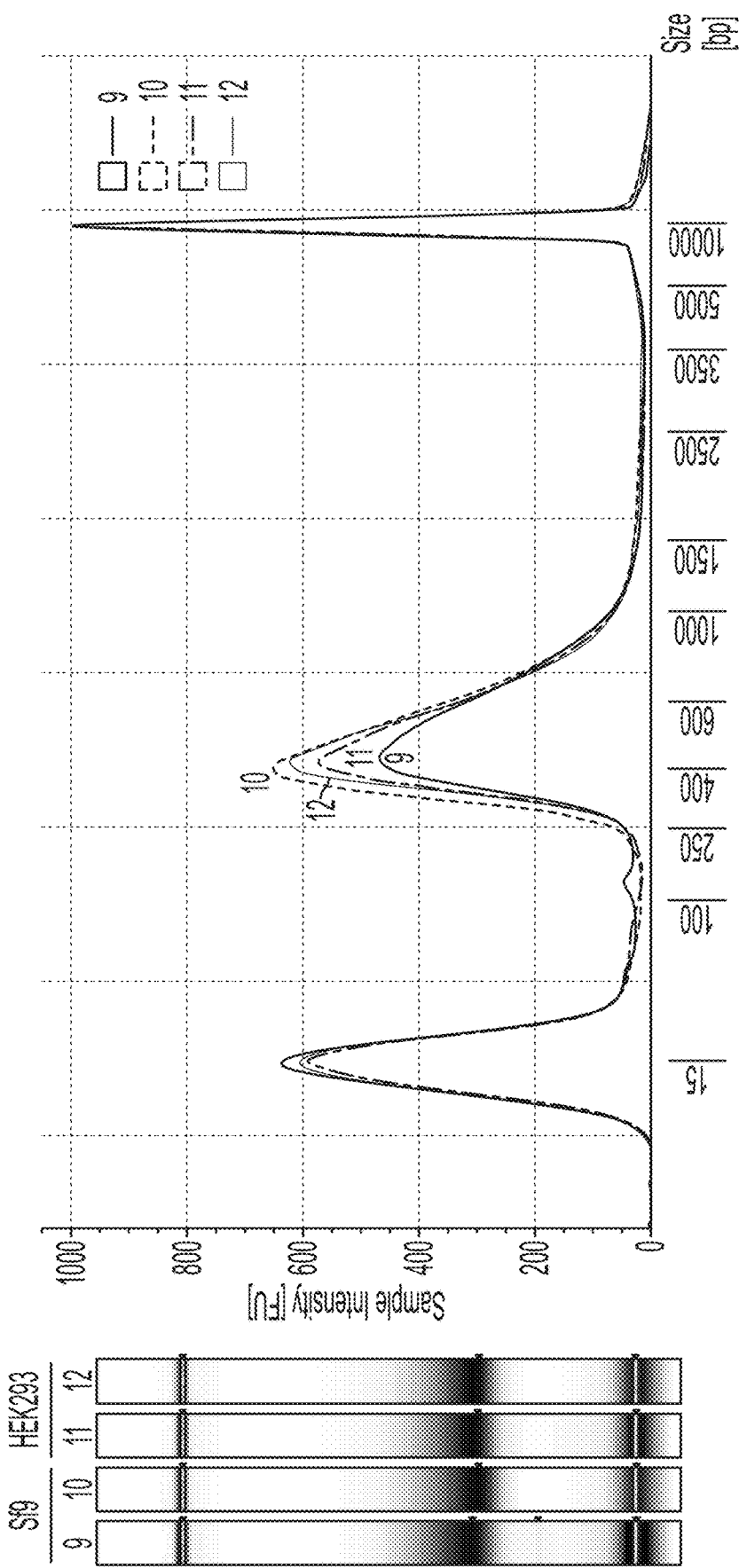

ACCEL-NGS® 2S PCR-Free DNA Library Kit (Swift Biosciences, Ann Arbor, Mich.) containing both PCR-free and PCR-enrichment options was utilized to produce NGS libraries. Deep DNAse treatment of purified rAAV particles and double-stranded (ds) DNA synthesis were performed following the protocol described by Lecomte et al.[26] with minor modifications. Briefly, $4 \times 10^{11}$ vector genomes (vg)-containing particles were extensively treated by Baseline ZERO and Plasmid-Safe exonucleases, followed by Proteinase K and RNAseA treatment. DNA was purified using Mag-Bind RxnPure Plus Kit (Omega Bio-Tek, Norcross, Ga.) using beads:DNA ratio of 2:1. After second strand synthesis with DNApolI, DNA was sonicated using a Covaris instrument. The following settings for DNA shearing were used: target size 400 bp, peak increment power—175 W, duty factor—10%, cycles per burst—200; time—38 sec, water level—15, water temperature—7.6-7.8° C., and the reaction volume—47 µL. Profiles of sheared input dsDNA and synthesized NGS libraries are presented in FIG. 14. Samples of rAAV DNA derived from Sf9 and HEK 293 cells demonstrated similar profiles and quality on each stage during NGS library preparation. At all stages of library preparations, the DNA quality was monitored by Tape station (Agilent) and Qubit (Thermo Fisher Scientific). For synthesis of PCR-free NGS libraries, 220 ng of ds DNA was sheared to a target size of 200 bp option input. For PCR-enriched libraries, 10% of DNA after Ligation Step 2 was amplified for eight cycles following manufacturer recommendations. Finally, all libraries were purified with 1×Mag-Bind beads.

Bioinformatics Analysis

Figure 15:
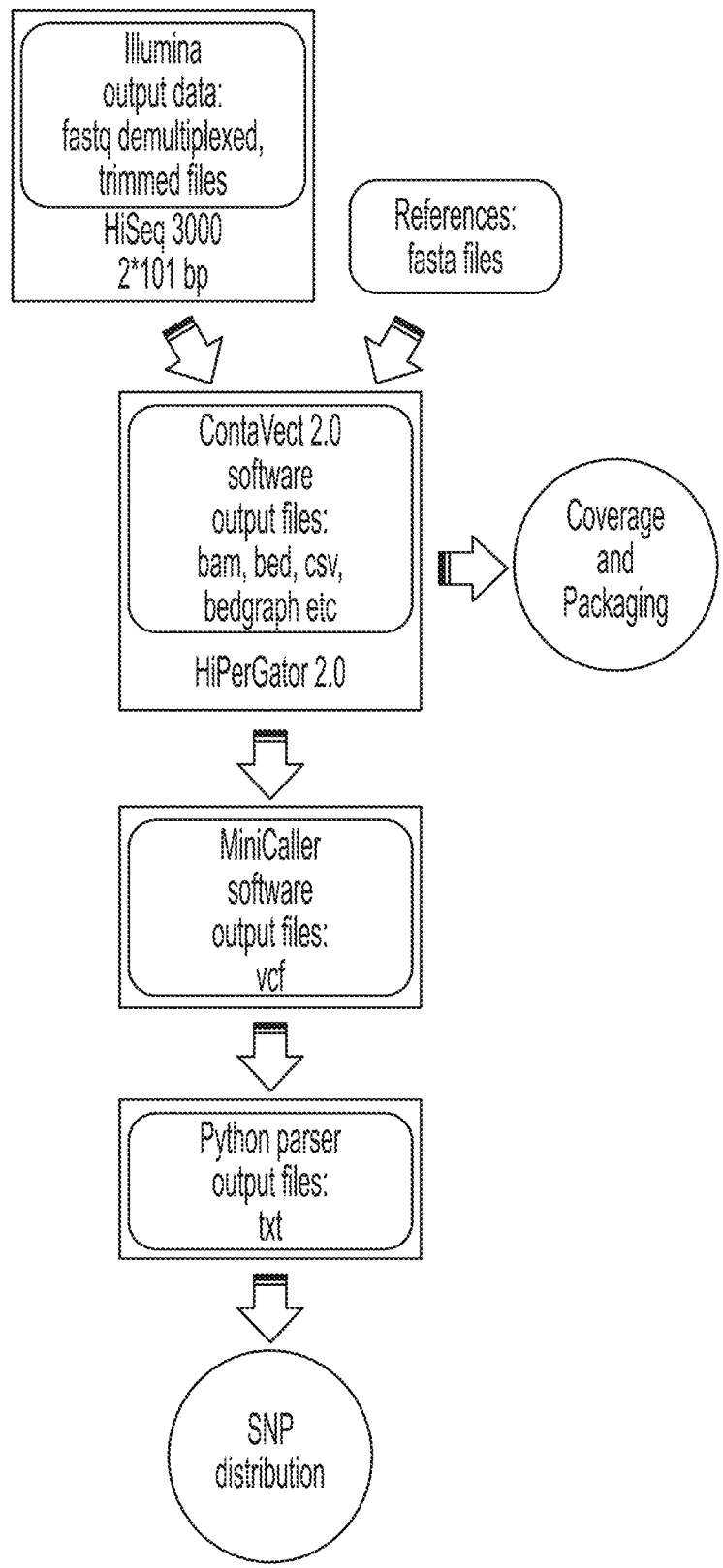
FIG. 15 depicts a non-limiting example of a schematic flowchart of NGS data processing.

The flowchart of the bioinformatics workflow is depicted in FIG. 15. Fastq files were analyzed with the dedicated open source software ContaVect v2.0[26] modified to be used on a supercomputing cluster in its default configuration. The ContaVect's code was adapted to appropriately scale the execution of blastn and bwa tools for maximum efficiency and throughput in a batch environment governed by a job scheduler. One of the changes was related to the ContaVect's limitation that would always run blastn and bwa with the number of threads equal to the total number of CPU cores on a computing node. Although this assumption may be valid in some cases when used on a personal workstation in a shared computing environment the number of threads generally has to be equal to the number of CPU cores requested for the batch job or available within a virtual machine. Otherwise, the efficiency of the program in question suffers greatly reducing the throughput of the analysis. The new modifications still allow the use of the old model for compatibility when the thread number is set to zero in the ContaVect configuration file, but now ContaVect can run blastn and bwa with the specified number of threads. One thread is used by default. In addition, an optional configuration file has been added that can be exported into the environment via the MATPLOTLIBRC environment variable to allow ContaVect to produce graphs using matplotlib without failure when run on cluster nodes without X11 environment. With the above modifications, the analyses had been successfully completed on the UF Research Computing HiPerGator supercomputer and the run time of ContaVect on the data was reduced from multiple days to hours. All modifications have been submitted as GitHub code pull requests to the ContaVect authors in the following repositories: github.com/a-slide/ContaVect and github.com/a-slide/pyDNA. All the described adaptations have been acknowledged and incorporated into the source code. SNP variants were retrieved from BAM files by MiniCaller software, a Java-based application utilized for the analysis of sequences with high-depth coverage (github-.com/lindenb/jvarkit/wiki/MiniCaller). MiniCaller-generated VCF files for HEK 293, or Sf9 rAAV libraries, as well as positive control libraries (each in duplicates) were aligned to the GenBank reference molecules. Parsing of VCF files was performed by Python script that generates CSV files (nbviewer.ipython.org/github/a-slide/iPython-Notebook/blob/master/Notebooks/VCF_analysis.ipynb). The VCF and CSV files are available from the Dryad Digital Repository: bio.rc.ufl.edu/secure/zolotukhin/genthed; username: "genther", password: "KrAkkegZ8F".

REFERENCES

1. Girod, A, Wobus, C E, Zadori, Z, Ried, M, Leike, K, Tijssen, P et al. (2002). The VP1 capsid protein of 1. adeno-associated virus type 2 is carrying a phospholipase A2 domain required for virus infectivity. *J Gen Virol* 83: 973-978.
2. Rose, J A, Maizel, J V, Jr., Inman, J K & Shatkin, A J. (1971). Structural proteins of adenovirus-associated viruses. *J Virol* 8: 766-770.
3. Johnson, F B, Ozer, H L & Hoggan, M D. (1971). Structural proteins of adenovirus-associated virus type 3. *J Virol* 8: 860-863.
4. Buller, R M & Rose, J A. (1978). Characterization of adenovirus-associated virus-induced polypeptides in KB cells. *J Virol* 25: 331-338.
5. Snijder, J, van de Waterbeemd, M, Damoc, E, Denisov, E, Grinfeld, D, Bennett, A et al. (2014). Defining the stoichiometry and cargo load of viral and bacterial nanoparticles by Orbitrap mass spectrometry. *J Am Chem Soc* 136: 7295-7299.
6. Urabe, M, Ding, C & Kotin, R M. (2002). Insect cells as a factory to produce adeno-associated virus type 2 vectors. *Hum Gene Ther* 13: 1935-1943.
7. Aslanidi, G, Lamb, K & Zolotukhin, S. (2009). An inducible system for highly efficient production of recombinant adeno-associated virus (rAAV) vectors in insect Sf9 cells. *Proc Natl Acad Sci USA* 106: 5059-5064.
8. Mietzsch, M, Casteleyn, V, Weger, S, Zolotukhin, S & Heilbronn, R. (2015). OneBac 2.0: Sf9 Cell Lines for Production of AAV5 Vectors with Enhanced Infectivity and Minimal Encapsidation of Foreign DNA. *Hum Gene Ther* 26: 688-697.
9. Kohlbrenner, E, Aslanidi, G, Nash, K, Shklyaev, S, Campbell-Thompson, M, Byrne, B J et al. (2005). Successful production of pseudotyped rAAV vectors using a modified baculovirus expression system. *Mol Ther* 12: 1217-1225.
10. Urabe, M, Nakakura, T, Xin, K Q, Obara, Y, Mizukami, H, Kume, A et al. (2006). Scalable generation of high-titer recombinant adeno-associated virus type 5 in insect cells. *J Virol* 80: 1874-1885.
11. Urabe, M, Ozawa, K, Haast, S & Hermens, Win E P 2311967 A2 20110420 (EN) (Amsterdam Molecular Therapeutics (AMT) B.V., 2015).
12. Chen, H. (2008). Intron splicing-mediated expression of AAV Rep and Cap genes and production of AAV vectors in insect cells. *Mol Ther* 16: 924-930.
13. Kozak, M. (1999). Initiation of translation in prokaryotes and eukaryotes. *Gene* 234: 187-208.
14. Cigan, A M & Donahue, T F. (1987). Sequence and structural features associated with translational initiator regions in yeast—a review. *Gene* 59: 1-18.
15. Joshi, C P, Zhou, H, Huang, X & Chiang, V L. (1997). Context sequences of translation initiation codon in plants. *Plant Mol Biol* 35: 993-1001.
16. Pesole, G, Gissi, C, Grillo, G, Licciulli, F, Liuni, S & Saccone, C. (2000). Analysis of oligonucleotide AUG start codon context in eukaryotic mRNAs. *Gene* 261: 85-91.
17. Kozak, M. (1987). An analysis of 5'-noncoding sequences from 699 vertebrate messenger RNAs. *Nucleic Acids Res* 15: 8125-8148.
18. Noderer, W L, Flockhart, R J, Bhaduri, A, Diaz de Arce, A J, Zhang, J, Khavari, P A et al. (2014). Quantitative analysis of mammalian translation initiation sites by FACS-seq. *Mol Syst Biol* 10: 748.
19. Salganik, M, Venkatakrishnan, B, Bennett, A, Lins, B, Yarbrough, J, Muzyczka, N et al. (2012). Evidence for pH-dependent protease activity in the adeno-associated virus capsid. *J Virol* 86: 11877-11885.
20. Storms, H F, van der Heijden, R, Tjaden, U R & van der Greef, J. (2006). Considerations for proteolytic labeling-optimization of 18O incorporation and prohibition of back-exchange. *Rapid Commun Mass Spectrom* 20: 3491-3497.
21. Ye, X, Luke, B, Andresson, T & Blonder, J. (2009). 18O stable isotope labeling in MS-based proteomics. *Brief Funct Genomic Proteomic* 8: 136-144.
22. Qian, W J, Liu, T, Petyuk, V A, Gritsenko, M A, Petritis, B O, Polpitiya, A D et al. (2009). Large-scale multiplexed quantitative discovery proteomics enabled by the use of an (18)O-labeled "universal" reference sample. *J Proteome Res* 8: 290-299.
23. Marsic, D, Mendez-Gomez, H R & Zolotukhin, S. (2015). High-accuracy biodistribution analysis of adeno-associated virus variants by double barcode sequencing. *Mol Ther Methods Clin Dev* 2: 15041.
24. Clark, K R, Voulgaropoulou, F & Johnson, P R. (1996). A stable cell line carrying adenovirus-inducible rep and cap genes allows for infectivity titration of adeno-associated virus vectors. *Gene Ther* 3: 1124-1132.
25. Ma, H, Galvin, T A, Glasner, D R, Shaheduzzaman, S & Khan, A S. (2014). Identification of a novel rhabdovirus in *Spodoptera frugiperda* cell lines. *J Virol* 88: 6576-6585.
26. Lecomte, E, Tournaire, B, Cogne, B, Dupont, J B, Lindenbaum, P, Martin-Fontaine, M et al. (2015). Advanced Characterization of DNA Molecules in rAAV Vector Preparations by Single-stranded Virus Next-generation Sequencing. *Mol Ther Nucleic Acids* 4: e260.
27. Mietzsch, M, Grasse, S, Zurawski, C, Weger, S, Bennett, A, Agbandje-McKenna, M et al. (2014). OneBac: platform for scalable and high-titer production of adeno-associated virus serotype 1-12 vectors for gene therapy. *Hum Gene Ther* 25: 212-222.
28. Grieger, J C, Snowdy, S & Samulski, R J. (2006). Separate basic region motifs within the adeno-associated virus capsid proteins are essential for infectivity and assembly. *J Virol* 80: 5199-5210.
29. Sonntag, F, Bleker, S, Leuchs, B, Fischer, R & Kleinschmidt, J A. (2006). Adeno-associated virus type 2 capsids with externalized VP1/VP2 trafficking domains are generated prior to passage through the cytoplasm and are maintained until uncoating occurs in the nucleus. *J Virol* 80: 11040-11054.
30. Popa-Wagner, R, Sonntag, F, Schmidt, K, King, J & Kleinschmidt, J A. (2012). Nuclear translocation of adeno-associated virus type 2 capsid proteins for virion assembly. *J Gen Virol* 93: 1887-1898.
31. Allay, J A, Sleep, S, Long, S, Tillman, D M, Clark, R, Carney, G et al. (2011). Good manufacturing practice production of self-complementary serotype 8 adeno-associated viral vector for a hemophilia B clinical trial. *Hum Gene Ther* 22: 595-604.
32. Ye, G J, Scotti, M M, Liu, J, Wang, L, Knop, D R & Veres, G. (2011). Clearance and characterization of residual HSV DNA in recombinant adeno-associated virus produced by an HSV complementation system. *Gene Ther* 18: 135-144.
33. Chadeuf, G, Ciron, C, Moullier, P & Salvetti, A. (2005). Evidence for encapsidation of prokaryotic sequences during recombinant adeno-associated virus production and their in vivo persistence after vector delivery. *Mol Ther* 12: 744-753.
34. Nony, P, Chadeuf, G, Tessier, J, Moullier, P & Salvetti, A. (2003). Evidence for packaging of rep-cap sequences into adeno-associated virus (AAV) type 2 capsids in the absence of inverted terminal repeats: a model for generation of rep-positive AAV particles. *J Virol* 77: 776-781.
35. Kapranov, P, Chen, L, Dederich, D, Dong, B, He, J, Steinmann, K E et al. (2012). Native molecular state of adeno-associated viral vectors revealed by single-molecule sequencing. *Hum Gene Ther* 23: 46-55.
36. Wang, Y, Ling, C, Song, L, Wang, L, Aslanidi, G V, Tan, M et al. (2012). Limitations of encapsidation of recombinant self-complementary adeno-associated viral genomes in different serotype capsids and their quantitation. *Hum Gene Ther Methods* 23: 225-233.
37. Cogne, B, Snyder, R, Lindenbaum, P, Dupont, J B, Redon, R, Moullier, P et al. (2014). NGS library preparation may generate artifactual integration sites of AAV vectors. *Nat Med* 20: 577-578.
38. Kozarewa, I, Ning, Z, Quail, M A, Sanders, M J, Berriman, M & Turner, D J. (2009). Amplification-free Illumina sequencing-library preparation facilitates improved mapping and assembly of (G+C)-biased genomes. *Nat Methods* 6: 291-295.
39. Folger, K R, Thomas, K & Capecchi, M R. (1985). Efficient correction of mismatched bases in plasmid heteroduplexes injected into cultured mammalian cell nuclei. *Mol Cell Biol* 5: 70-74.
40. Zolotukhin, S, Potter, M, Hauswirth, W W, Guy, J & Muzyczka, N. (1996). A "humanized" green fluorescent protein cDNA adapted for high-level expression in mammalian cells. *J Virol* 70: 4646-4654.
41. Faust, S M, Bell, P, Cutler, B J, Ashley, S N, Zhu, Y, Rabinowitz, J E et al. (2013). CpG-depleted adeno-associated virus vectors evade immune detection. *J Clin Invest* 123: 2994-3001.
42. Herzog, R W. (2016). A Cure For Hemophilia: the Promise Becomes a Reality. *Mol Ther* 24: 1503-1504.
43. Dolgin, E. (2016). Early clinical data raise the bar for hemophilia gene therapies. *Nat Biotechnol* 34: 999-1001.
44. Zolotukhin, S, Byrne, B J, Mason, E, Zolotukhin, I, Potter, M, Chesnut, K et al. (1999). Recombinant adeno-associated virus purification using novel methods improves infectious titer and yield. *Gene Ther* 6: 973-985.
45. Smith, R H, Levy, J R & Kotin, R M. (2009). A simplified baculovirus-AAV expression vector system coupled with one-step affinity purification yields high-titer rAAV stocks from insect cells. *Mol Ther* 17: 1888-1896.
46. Lock, M, Alvira, M R, Chen, S J & Wilson, J M. (2014). Absolute determination of single-stranded and self-complementary adeno-associated viral vector genome titers by droplet digital PCR. *Hum Gene Ther Methods* 25: 115-125.
47. Piedra, J, Ontiveros, M, Miravet, S, Penalva, C, Monfar, M & Chillon, M. (2015). Development of a rapid, robust, and universal picogreen-based method to titer adeno-associated vectors. *Hum Gene Ther Methods* 26: 35-42.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present disclosure, and without departing from the spirit and scope thereof, can make various changes and modifications of the disclosure to adapt it to various usages and conditions. Thus, other embodiments are also within the claims.

EQUIVALENTS

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be non-limiting and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03. It should be appreciated that embodiments described in this document using an open-ended transitional phrase (e.g., "comprising") are also contemplated, in alternative embodiments, as "consisting of" and "consisting essentially of" the feature described by the open-ended transitional phrase. For example, if the disclosure describes "a composition comprising A and B", the disclosure also contemplates the alternative embodiments "a composition consisting of A and B" and "a composition consisting essentially of A and B".

What is claimed is:

1. A nucleic acid comprising a modified Kozak sequence operably linked to a nucleotide sequence encoding adeno-associated virus (AAV) VP1, VP2, and VP3 capsid proteins, wherein the modified Kozak sequence is selected from SEQ ID NOs: 46-55.

2. The nucleic acid of claim 1, wherein the modified Kozak sequence is SEQ ID NO: 49.

3. The nucleic acid of claim 1, wherein the VP1, VP2, and VP3 capsid proteins are derived from an AAV3 serotype.

4. The nucleic acid of claim 1, further comprising a promoter sequence.

5. The nucleic acid of claim 4, wherein the promoter sequence is a polyhedrin (polh) promoter sequence.

6. The nucleic acid of any one of claims 1-5, wherein the modified Kozak sequence contains an initiation codon for translation of the VP1 capsid protein.

7. The nucleic acid of claim 6, wherein the initiation codon for translation of the VP1 capsid protein is AUG.

8. The nucleic acid of claim 1, wherein the nucleic acid is packaged in a viral particle, optionally a baculovirus particle.

9. An insect cell comprising the nucleic acid of claim 1.

10. The insect cell of claim 9, wherein the nucleic acid is integrated into the genome of the insect cell.

11. A method of producing recombinant AAV (rAAV) in an insect cell, wherein the rAAV is derived from an AAV3 serotype, the method comprising:
   a) transfecting an insect cell with:
      i) a baculovirus comprising the nucleic acid of claim 1;
      ii) a baculovirus comprising a nucleic acid encoding an AAV Rep protein;
      iii) a baculovirus comprising a nucleic acid comprising two AAV inverted terminal repeat (ITR) nucleotide sequences flanking a gene of interest operably linked to a promoter sequence;
   b) culturing the insect cell under conditions suitable to produce rAAV; and
   c) recovering the rAAV from the insect cell.

12. A method of producing recombinant AAV (rAAV) in an insect cell, wherein the rAAV is derived from an AAV3 serotype, the method comprising:
   a) transfecting an insect cell of claim 9 or claim 10 with a nucleic acid, optionally in a baculovirus, comprising two AAV inverted terminal repeat (ITR) nucleotide sequences flanking a gene of interest operably linked to a promoter sequence;
   b) culturing the insect cell under conditions suitable to produce rAAV; and
   c) recovering the rAAV from the insect cell.

13. The method of claim 11, wherein the insect cell is an Sf9 cell.

14. A nucleic acid comprising a modified Kozak sequence operably linked to a nucleotide sequence encoding adeno-associated virus (AAV) VP1, VP2, and VP3 capsid proteins, wherein the modified Kozak sequence is selected from SEQ ID NOs: 56-67.

15. The nucleic acid of claim 14, wherein the modified Kozak sequence is SEQ ID NO: 56, SEQ ID NO: 57, SEQ ID NO: 58, SEQ ID NO: 59, SEQ ID NO: 60, SEQ ID NO: 61, SEQ ID NO: 62, or SEQ ID NO: 63.

16. The nucleic acid of claim 14, wherein the VP1, VP2, and VP3 capsid proteins are derived from an AAV6 serotype.

17. The nucleic acid of claim 14 or claim 16, further comprising a promoter sequence.

18. The nucleic acid of claim 17, wherein the promoter sequence is a polyhedrin (polh) promoter sequence.

19. The nucleic acid of claim 14, wherein the modified Kozak sequence contains an initiation codon for translation of the VP1 capsid protein.

20. The nucleic acid of claim 19, wherein the initiation codon for translation of the VP1 capsid protein is AUG.

21. The nucleic acid of claim 14, wherein the nucleic acid is packaged in a viral particle, optionally a baculovirus particle.

22. An insect cell comprising the nucleic acid of claim 14.

23. The insect cell of claim 22, wherein the nucleic acid is integrated into the genome of the insect cell.

24. A method of producing recombinant AAV (rAAV) in an insect cell, wherein the rAAV is derived from an AAV6 serotype, the method comprising:
   a) transfecting an insect cell with:
      i) a baculovirus comprising the nucleic acid of claim 14;
      ii) a baculovirus comprising a nucleic acid encoding an AAV Rep protein;
      iii) a baculovirus comprising a nucleic acid comprising two AAV inverted terminal repeat (ITR) nucleotide sequences flanking a gene of interest operably linked to a promoter sequence;
   b) culturing the insect cell under conditions suitable to produce rAAV; and
   c) recovering the rAAV from the insect cell.

25. A method of producing recombinant AAV (rAAV) in an insect cell, wherein the rAAV is derived from an AAV6 serotype, the method comprising:

a) transfecting an insect cell of claim 22 or claim 23 with a nucleic acid, optionally in a baculovirus, comprising two AAV inverted terminal repeat (ITR) nucleotide sequences flanking a gene of interest operably linked to a promoter sequence;
b) culturing the insect cell under conditions suitable to produce rAAV; and
c) recovering the rAAV from the insect cell.

26. The method of claim 24, wherein the insect cell is an Sf9 cell.

27. A method of identifying an adeno-associated virus (AAV) capsid protein translation initiation sequence for producing rAAV particles in a host cell, the method comprising,
a) introducing each of a plurality of different recombinant AAV capsid genes into producer cells, wherein each different recombinant AAV capsid gene is operably linked to a different Kozak sequence,
b) isolating resulting rAAV particles from the producer cells, and
c) evaluating properties of the isolated rAAV particles from step b).

28. The method of claim 27, wherein the producer cell is an insect cell or a mammalian cell.

29. The method of claim 27, wherein the translation initiation sequence is an ATG/AUG codon.

30. The method of claim 27, wherein the rAAV particles are evaluated by assaying their relative VP1/VP2/VP3 content, their yield, their DNA content, their infectivity, or a combination of two or more thereof.

* * * * *

SEQUENCE LISTING

```
<160> NUMBER OF SEQ ID NOS: 81

<210> SEQ ID NO 1
<211> LENGTH: 11
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: n is c or t
<220> FEATURE:
<221> NAME/KEY: misc_feature
<222> LOCATION: (2)..(2)
<223> OTHER INFORMATION: n is a, c, g, or t
<220> FEATURE:
<221> NAME/KEY: misc_feature
<222> LOCATION: (3)..(3)
<223> OTHER INFORMATION: n is g or t
<220> FEATURE:
<221> NAME/KEY: misc_feature
<222> LOCATION: (5)..(5)
<223> OTHER INFORMATION: n is g or t
<220> FEATURE:
<221> NAME/KEY: misc_feature
<222> LOCATION: (10)..(10)
<223> OTHER INFORMATION: n is a, c, g, or t
<220> FEATURE:
<221> NAME/KEY: misc_feature
<222> LOCATION: (11)..(11)
<223> OTHER INFORMATION: n is a, c, or t

<400> SEQUENCE: 1
nnntntatgn n                                                          11

<210> SEQ ID NO 2
<211> LENGTH: 11
```

```
<212> TYPE: RNA
<213> ORGANISM: Artificial Sequence
<220> FEATURE:
<223> OTHER INFORMATION: Synthetic Polynucleotide

<400> SEQUENCE: 2
cauuguaugu c                                                          11

<210> SEQ ID NO 3
<211> LENGTH: 11
<212> TYPE: RNA
<213> ORGANISM: Artificial Sequence
<220> FEATURE:
<223> OTHER INFORMATION: Synthetic Polynucleotide

<400> SEQUENCE: 3
ucguuuaugg a                                                          11

<210> SEQ ID NO 4
<211> LENGTH: 11
<212> TYPE: RNA
<213> ORGANISM: Artificial Sequence
<220> FEATURE:
<223> OTHER INFORMATION: Synthetic Polynucleotide

<400> SEQUENCE: 4
caguuuaugg u                                                          11

<210> SEQ ID NO 5
<211> LENGTH: 11
<212> TYPE: RNA
<213> ORGANISM: Artificial Sequence
<220> FEATURE:
<223> OTHER INFORMATION: Synthetic Polynucleotide

<400> SEQUENCE: 5
cauuguaugg u                                                          11

<210> SEQ ID NO 6
<211> LENGTH: 11
<212> TYPE: RNA
<213> ORGANISM: Artificial Sequence
<220> FEATURE:
<223> OTHER INFORMATION: Synthetic Polynucleotide

<400> SEQUENCE: 6
uaguguaugc u                                                          11

<210> SEQ ID NO 7
<211> LENGTH: 11
<212> TYPE: RNA
<213> ORGANISM: Artificial Sequence
<220> FEATURE:
<223> OTHER INFORMATION: Synthetic Polynucleotide

<400> SEQUENCE: 7
cauuguaugc u                                                          11

<210> SEQ ID NO 8
<211> LENGTH: 11
<212> TYPE: RNA
<213> ORGANISM: Artificial Sequence
<220> FEATURE:
<223> OTHER INFORMATION: Synthetic Polynucleotide

<400> SEQUENCE: 8
```
ucuuuuaugu c                                                                     11

<210> SEQ ID NO 9
<211> LENGTH: 11
<212> TYPE: RNA
<213> ORGANISM: Artificial Sequence
<220> FEATURE:
<223> OTHER INFORMATION: Synthetic Polynucleotide

<400> SEQUENCE: 9
uguuuuaugu c                                                                     11

<210> SEQ ID NO 10
<211> LENGTH: 11
<212> TYPE: RNA
<213> ORGANISM: Artificial Sequence
<220> FEATURE:
<223> OTHER INFORMATION: Synthetic Polynucleotide

<400> SEQUENCE: 10
uaguuuaugu c                                                                     11

<210> SEQ ID NO 11
<211> LENGTH: 11
<212> TYPE: RNA
<213> ORGANISM: Artificial Sequence
<220> FEATURE:
<223> OTHER INFORMATION: Synthetic Polynucleotide

<400> SEQUENCE: 11
uaguguaugu c                                                                     11

<210> SEQ ID NO 12
<211> LENGTH: 11
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: n is a, c, or t
<220> FEATURE:
<221> NAME/KEY: misc_feature
<222> LOCATION: (2)..(2)
<223> OTHER INFORMATION: n is a, c, g, or t
<220> FEATURE:
<221> NAME/KEY: misc_feature
<222> LOCATION: (3)..(3)
<223> OTHER INFORMATION: n is g or t
<220> FEATURE:
<221> NAME/KEY: misc_feature
<222> LOCATION: (4)..(4)
<223> OTHER INFORMATION: n is c or t
<220> FEATURE:
<221> NAME/KEY: misc_feature
<222> LOCATION: (5)..(5)
<223> OTHER INFORMATION: n is a, c, g, or t
<220> FEATURE:
<221> NAME/KEY: misc_feature
<222> LOCATION: (6)..(6)
<223> OTHER INFORMATION: n is c or t
<220> FEATURE:
<221> NAME/KEY: misc_feature
<222> LOCATION: (10)..(10)
<223> OTHER INFORMATION: n is g or t
<220> FEATURE:
<221> NAME/KEY: misc_feature
<222> LOCATION: (11)..(11)
<223> OTHER INFORMATION: n is c or g

<400> SEQUENCE: 12
nnnnnnatgn n                                           11

<210> SEQ ID NO 13
<211> LENGTH: 11
<212> TYPE: RNA
<213> ORGANISM: Artificial Sequence
<220> FEATURE:
<223> OTHER INFORMATION: Synthetic Polynucleotide

<400> SEQUENCE: 13
uagcgcaugg c                                           11

<210> SEQ ID NO 14
<211> LENGTH: 11
<212> TYPE: RNA
<213> ORGANISM: Artificial Sequence
<220> FEATURE:
<223> OTHER INFORMATION: Synthetic Polynucleotide

<400> SEQUENCE: 14
ugguauaugg c                                           11

<210> SEQ ID NO 15
<211> LENGTH: 11
<212> TYPE: RNA
<213> ORGANISM: Artificial Sequence
<220> FEATURE:
<223> OTHER INFORMATION: Synthetic Polynucleotide

<400> SEQUENCE: 15
uaguuuaugg c                                           11

<210> SEQ ID NO 16
<211> LENGTH: 11
<212> TYPE: RNA
<213> ORGANISM: Artificial Sequence
<220> FEATURE:
<223> OTHER INFORMATION: Synthetic Polynucleotide

<400> SEQUENCE: 16
caguguaugg c                                           11

<210> SEQ ID NO 17
<211> LENGTH: 11
<212> TYPE: RNA
<213> ORGANISM: Artificial Sequence
<220> FEATURE:
<223> OTHER INFORMATION: Synthetic Polynucleotide

<400> SEQUENCE: 17
uaguguaugg c                                           11

<210> SEQ ID NO 18
<211> LENGTH: 11
<212> TYPE: RNA
<213> ORGANISM: Artificial Sequence
<220> FEATURE:
<223> OTHER INFORMATION: Synthetic Polynucleotide

<400> SEQUENCE: 18
uauuguaugg c                                           11

<210> SEQ ID NO 19
<211> LENGTH: 11
<212> TYPE: RNA

```
<213> ORGANISM: Artificial Sequence
<220> FEATURE:
<223> OTHER INFORMATION: Synthetic Polynucleotide

<400> SEQUENCE: 19
cauuguaugg c                                                         11

<210> SEQ ID NO 20
<211> LENGTH: 11
<212> TYPE: RNA
<213> ORGANISM: Artificial Sequence
<220> FEATURE:
<223> OTHER INFORMATION: Synthetic Polynucleotide

<400> SEQUENCE: 20
ccguuuaugg g                                                         11

<210> SEQ ID NO 21
<211> LENGTH: 11
<212> TYPE: RNA
<213> ORGANISM: Artificial Sequence
<220> FEATURE:
<223> OTHER INFORMATION: Synthetic Polynucleotide

<400> SEQUENCE: 21
acuuguaugg g                                                         11

<210> SEQ ID NO 22
<211> LENGTH: 11
<212> TYPE: RNA
<213> ORGANISM: Artificial Sequence
<220> FEATURE:
<223> OTHER INFORMATION: Synthetic Polynucleotide

<400> SEQUENCE: 22
cauuuuaugg g                                                         11

<210> SEQ ID NO 23
<211> LENGTH: 11
<212> TYPE: RNA
<213> ORGANISM: Artificial Sequence
<220> FEATURE:
<223> OTHER INFORMATION: Synthetic Polynucleotide

<400> SEQUENCE: 23
uaguguaugu c                                                         11

<210> SEQ ID NO 24
<211> LENGTH: 11
<212> TYPE: RNA
<213> ORGANISM: Artificial Sequence
<220> FEATURE:
<223> OTHER INFORMATION: Synthetic Polynucleotide

<400> SEQUENCE: 24
uaguuuaugu c                                                         11

<210> SEQ ID NO 25
<211> LENGTH: 11
<212> TYPE: RNA
<213> ORGANISM: Artificial Sequence
<220> FEATURE:
<223> OTHER INFORMATION: Synthetic Polynucleotide

<400> SEQUENCE: 25
uguuuuaugu c                                                         11
```

<210> SEQ ID NO 26
<211> LENGTH: 11
<212> TYPE: RNA
<213> ORGANISM: Artificial Sequence
<220> FEATURE:
<223> OTHER INFORMATION: Synthetic Polynucleotide

<400> SEQUENCE: 26 ucuuuaugu c                                                           11

<210> SEQ ID NO 27
<211> LENGTH: 11
<212> TYPE: RNA
<213> ORGANISM: Artificial Sequence
<220> FEATURE:
<223> OTHER INFORMATION: Synthetic Polynucleotide

<400> SEQUENCE: 27
uaguguaugg g                                                          11

<210> SEQ ID NO 28
<211> LENGTH: 11
<212> TYPE: RNA
<213> ORGANISM: Artificial Sequence
<220> FEATURE:
<223> OTHER INFORMATION: Synthetic Polynucleotide

<400> SEQUENCE: 28
uaguuuaugg g                                                          11

<210> SEQ ID NO 29
<211> LENGTH: 11
<212> TYPE: RNA
<213> ORGANISM: Artificial Sequence
<220> FEATURE:
<223> OTHER INFORMATION: Synthetic Polynucleotide

<400> SEQUENCE: 29
uguuuuaugg g                                                          11

<210> SEQ ID NO 30
<211> LENGTH: 11
<212> TYPE: RNA
<213> ORGANISM: Artificial Sequence
<220> FEATURE:
<223> OTHER INFORMATION: Synthetic Polynucleotide

<400> SEQUENCE: 30
ucuuuuaugg g                                                          11

<210> SEQ ID NO 31
<211> LENGTH: 11
<212> TYPE: RNA
<213> ORGANISM: Artificial Sequence
<220> FEATURE:
<223> OTHER INFORMATION: Synthetic Polynucleotide

<400> SEQUENCE: 31
uaguguaugu c                                                          11

<210> SEQ ID NO 32
<211> LENGTH: 11
<212> TYPE: RNA
<213> ORGANISM: Artificial Sequence
<220> FEATURE:

<223> OTHER INFORMATION: Synthetic Polynucleotide

<400> SEQUENCE: 32
uaguuuaugu c                                                                11

<210> SEQ ID NO 33
<211> LENGTH: 11
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (2)..(2)
<223> OTHER INFORMATION: n is a, c, g, or t
<220> FEATURE:
<221> NAME/KEY: misc_feature
<222> LOCATION: (3)..(3)
<223> OTHER INFORMATION: n is g or t
<220> FEATURE:
<221> NAME/KEY: misc_feature
<222> LOCATION: (5)..(5)
<223> OTHER INFORMATION: n is g or t
<220> FEATURE:
<221> NAME/KEY: misc_feature
<222> LOCATION: (10)..(10)
<223> OTHER INFORMATION: n is g or t
<220> FEATURE:
<221> NAME/KEY: misc_feature
<222> LOCATION: (11)..(11)
<223> OTHER INFORMATION: n is c or g

<400> SEQUENCE: 33
tnntntatgn n                                                                11

<210> SEQ ID NO 34
<211> LENGTH: 11
<212> TYPE: RNA
<213> ORGANISM: Artificial Sequence
<220> FEATURE:
<223> OTHER INFORMATION: Synthetic Polynucleotide

<400> SEQUENCE: 34
uaguguaugu c                                                                11

<210> SEQ ID NO 35
<211> LENGTH: 11
<212> TYPE: RNA
<213> ORGANISM: Artificial Sequence
<220> FEATURE:
<223> OTHER INFORMATION: Synthetic Polynucleotide

<400> SEQUENCE: 35
uaguuuaugu c                                                                11

<210> SEQ ID NO 36
<211> LENGTH: 11
<212> TYPE: RNA
<213> ORGANISM: Artificial Sequence
<220> FEATURE:
<223> OTHER INFORMATION: Synthetic Polynucleotide

<400> SEQUENCE: 36
uguuuuaugu c                                                                11

<210> SEQ ID NO 37
<211> LENGTH: 11
<212> TYPE: RNA
<213> ORGANISM: Artificial Sequence

```
<220> FEATURE:
<223> OTHER INFORMATION: Synthetic Polynucleotide

<400> SEQUENCE: 37
ucuuuuaugu c                                                              11

<210> SEQ ID NO 38
<211> LENGTH: 11
<212> TYPE: RNA
<213> ORGANISM: Artificial Sequence
<220> FEATURE:
<223> OTHER INFORMATION: Synthetic Polynucleotide

<400> SEQUENCE: 38
uaguguaugg g                                                              11

<210> SEQ ID NO 39
<211> LENGTH: 11
<212> TYPE: RNA
<213> ORGANISM: Artificial Sequence
<220> FEATURE:
<223> OTHER INFORMATION: Synthetic Polynucleotide

<400> SEQUENCE: 39
uaguuuaugg g                                                              11

<210> SEQ ID NO 40
<211> LENGTH: 11
<212> TYPE: RNA
<213> ORGANISM: Artificial Sequence
<220> FEATURE:
<223> OTHER INFORMATION: Synthetic Polynucleotide

<400> SEQUENCE: 40
uguuuuaugg g                                                              11

<210> SEQ ID NO 41
<211> LENGTH: 11
<212> TYPE: RNA
<213> ORGANISM: Artificial Sequence
<220> FEATURE:
<223> OTHER INFORMATION: Synthetic Polynucleotide

<400> SEQUENCE: 41
ucuuuuaugg g                                                              11

<210> SEQ ID NO 42
<211> LENGTH: 11
<212> TYPE: RNA
<213> ORGANISM: Artificial Sequence
<220> FEATURE:
<223> OTHER INFORMATION: Synthetic Polynucleotide

<400> SEQUENCE: 42
uaguguaugg c                                                              11

<210> SEQ ID NO 43
<211> LENGTH: 11
<212> TYPE: RNA
<213> ORGANISM: Artificial Sequence
<220> FEATURE:
<223> OTHER INFORMATION: Synthetic Polynucleotide

<400> SEQUENCE: 43
uaguuuaugg c                                                              11
```

```
<210> SEQ ID NO 44
<211> LENGTH: 11
<212> TYPE: RNA
<213> ORGANISM: Artificial Sequence
<220> FEATURE:
<223> OTHER INFORMATION: Synthetic Polynucleotide

<400> SEQUENCE: 44
uguuuuaugg c                                                                11

<210> SEQ ID NO 45
<211> LENGTH: 11
<212> TYPE: RNA
<213> ORGANISM: Artificial Sequence
<220> FEATURE:
<223> OTHER INFORMATION: Synthetic Polynucleotide

<400> SEQUENCE: 45
ucuuuuaugg c                                                                11

<210> SEQ ID NO 46
<211> LENGTH: 21
<212> TYPE: RNA
<213> ORGANISM: Artificial Sequence
<220> FEATURE:
<223> OTHER INFORMATION: Synthetic Polynucleotide

<400> SEQUENCE: 46
gcgcagaucu ucuuuuaugg c                                                     21

<210> SEQ ID NO 47
<211> LENGTH: 21
<212> TYPE: RNA
<213> ORGANISM: Artificial Sequence
<220> FEATURE:
<223> OTHER INFORMATION: Synthetic Polynucleotide

<400> SEQUENCE: 47
gcgcagaucu uguuuuaugg c                                                     21

<210> SEQ ID NO 48
<211> LENGTH: 22
<212> TYPE: RNA
<213> ORGANISM: Artificial Sequence
<220> FEATURE:
<223> OTHER INFORMATION: Synthetic Polynucleotide

<400> SEQUENCE: 48
gcgcagaucu uaguuuaaug gc                                                    22

<210> SEQ ID NO 49
<211> LENGTH: 21
<212> TYPE: RNA
<213> ORGANISM: Artificial Sequence
<220> FEATURE:
<223> OTHER INFORMATION: Synthetic Polynucleotide

<400> SEQUENCE: 49
gcgcagaucu uaguguaugg c                                                     21

<210> SEQ ID NO 50
<211> LENGTH: 21
<212> TYPE: RNA
<213> ORGANISM: Artificial Sequence
<220> FEATURE:
<223> OTHER INFORMATION: Synthetic Polynucleotide
```

```
<400> SEQUENCE: 50
gcgcagaucu cauuguaugg c                                              21

<210> SEQ ID NO 51
<211> LENGTH: 21
<212> TYPE: RNA
<213> ORGANISM: Artificial Sequence
<220> FEATURE:
<223> OTHER INFORMATION: Synthetic Polynucleotide

<400> SEQUENCE: 51
gcgcagaucu caguuuaugg c                                              21

<210> SEQ ID NO 52
<211> LENGTH: 21
<212> TYPE: RNA
<213> ORGANISM: Artificial Sequence
<220> FEATURE:
<223> OTHER INFORMATION: Synthetic Polynucleotide

<400> SEQUENCE: 52
gcgcagaucu uauugcaugg c                                              21

<210> SEQ ID NO 53
<211> LENGTH: 21
<212> TYPE: RNA
<213> ORGANISM: Artificial Sequence
<220> FEATURE:
<223> OTHER INFORMATION: Synthetic Polynucleotide

<400> SEQUENCE: 53
gcgcagaucu uauuguaugg c                                              21

<210> SEQ ID NO 54
<211> LENGTH: 22
<212> TYPE: RNA
<213> ORGANISM: Artificial Sequence
<220> FEATURE:
<223> OTHER INFORMATION: Synthetic Polynucleotide

<400> SEQUENCE: 54
gcgcagaucu aauuguaaug gc                                             22

<210> SEQ ID NO 55
<211> LENGTH: 23
<212> TYPE: RNA
<213> ORGANISM: Artificial Sequence
<220> FEATURE:
<223> OTHER INFORMATION: Synthetic Polynucleotide

<400> SEQUENCE: 55
auuaaggauc cuuaguguau ggc                                            23

<210> SEQ ID NO 56
<211> LENGTH: 11
<212> TYPE: RNA
<213> ORGANISM: Artificial Sequence
<220> FEATURE:
<223> OTHER INFORMATION: Synthetic Polynucleotide

<400> SEQUENCE: 56
uaguuuaugg c                                                         11

<210> SEQ ID NO 57
```

```
<211> LENGTH: 11
<212> TYPE: RNA
<213> ORGANISM: Artificial Sequence
<220> FEATURE:
<223> OTHER INFORMATION: Synthetic Polynucleotide

<400> SEQUENCE: 57
caguuuaugg c                                                            11

<210> SEQ ID NO 58
<211> LENGTH: 11
<212> TYPE: RNA
<213> ORGANISM: Artificial Sequence
<220> FEATURE:
<223> OTHER INFORMATION: Synthetic Polynucleotide

<400> SEQUENCE: 58
uauugcaugg c                                                            11

<210> SEQ ID NO 59
<211> LENGTH: 11
<212> TYPE: RNA
<213> ORGANISM: Artificial Sequence
<220> FEATURE:
<223> OTHER INFORMATION: Synthetic Polynucleotide

<400> SEQUENCE: 59
uaguguaugg c                                                            11

<210> SEQ ID NO 60
<211> LENGTH: 11
<212> TYPE: RNA
<213> ORGANISM: Artificial Sequence
<220> FEATURE:
<223> OTHER INFORMATION: Synthetic Polynucleotide

<400> SEQUENCE: 60
aauuguaugg c                                                            11

<210> SEQ ID NO 61
<211> LENGTH: 11
<212> TYPE: RNA
<213> ORGANISM: Artificial Sequence
<220> FEATURE:
<223> OTHER INFORMATION: Synthetic Polynucleotide

<400> SEQUENCE: 61
uauuguaugg c                                                            11

<210> SEQ ID NO 62
<211> LENGTH: 11
<212> TYPE: RNA
<213> ORGANISM: Artificial Sequence
<220> FEATURE:
<223> OTHER INFORMATION: Synthetic Polynucleotide

<400> SEQUENCE: 62
cauuguaugg c                                                            11

<210> SEQ ID NO 63
<211> LENGTH: 11
<212> TYPE: RNA
<213> ORGANISM: Artificial Sequence
<220> FEATURE:
<223> OTHER INFORMATION: Synthetic Polynucleotide

<400> SEQUENCE: 63
```
uguuuuaugg g                                                       11

<210> SEQ ID NO 64
<211> LENGTH: 11
<212> TYPE: RNA
<213> ORGANISM: Artificial Sequence
<220> FEATURE:
<223> OTHER INFORMATION: Synthetic Polynucleotide

<400> SEQUENCE: 64
uguuuuaugu c                                                       11

<210> SEQ ID NO 65
<211> LENGTH: 11
<212> TYPE: RNA
<213> ORGANISM: Artificial Sequence
<220> FEATURE:
<223> OTHER INFORMATION: Synthetic Polynucleotide

<400> SEQUENCE: 65
uauuuuaugg g                                                       11

<210> SEQ ID NO 66
<211> LENGTH: 11
<212> TYPE: RNA
<213> ORGANISM: Artificial Sequence
<220> FEATURE:
<223> OTHER INFORMATION: Synthetic Polynucleotide

<400> SEQUENCE: 66
uaguuuaugg g                                                       11

<210> SEQ ID NO 67
<211> LENGTH: 11
<212> TYPE: RNA
<213> ORGANISM: Artificial Sequence
<220> FEATURE:
<223> OTHER INFORMATION: Synthetic Polynucleotide

<400> SEQUENCE: 67
uaguuuaugu c                                                       11

<210> SEQ ID NO 68
<211> LENGTH: 11
<212> TYPE: RNA
<213> ORGANISM: Adeno-associated virus 5

<400> SEQUENCE: 68
guagucaugu c                                                       11

<210> SEQ ID NO 69
<211> LENGTH: 11
<212> TYPE: RNA
<213> ORGANISM: Adeno-associated virus 9

<400> SEQUENCE: 69
ccagguaugg c                                                       11

<210> SEQ ID NO 70
<211> LENGTH: 13
<212> TYPE: PRT
<213> ORGANISM: Artificial Sequence
<220> FEATURE:
<223> OTHER INFORMATION: Synthetic Polypeptide

```
<400> SEQUENCE: 70

Thr Trp Val Leu Pro Ser Tyr Asn Asn His Gln Tyr Arg
1               5                   10

<210> SEQ ID NO 71
<211> LENGTH: 11
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (4)..(4)
<223> OTHER INFORMATION: n is a or g

<400> SEQUENCE: 71
gccnccaugg c                                                             11

<210> SEQ ID NO 72
<211> LENGTH: 14
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (4)..(4)
<223> OTHER INFORMATION: n is c or g

<400> SEQUENCE: 72
ucanuguguu augg                                                          14

<210> SEQ ID NO 73
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 73

Pro Lys Arg Lys Lys Ala Arg Thr
1               5

<210> SEQ ID NO 74
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 74
atagggactt tccattgacg tc                                                 22

<210> SEQ ID NO 75
<211> LENGTH: 24
<212> TYPE: DNA
<213> ORGANISM: Artificial Sequence
<220> FEATURE:
<223> OTHER INFORMATION: Synthetic Polynucleotide

<400> SEQUENCE: 75
tgatacactt gatgtactgc caag                                               24

<210> SEQ ID NO 76
<211> LENGTH: 27
<212> TYPE: DNA
<213> ORGANISM: Artificial Sequence
```

```
<220> FEATURE:
<223> OTHER INFORMATION: Synthetic Polynucleotide

<400> SEQUENCE: 76
tgggtggact atttacggta aactgcc                                             27

<210> SEQ ID NO 77
<211> LENGTH: 724
<212> TYPE: PRT
<213> ORGANISM: Artificial Sequence
<220> FEATURE:
<223> OTHER INFORMATION: Synthetic Polypeptide

<400> SEQUENCE: 77
```

Met Ser Phe Val Asp His Pro Pro Asp Trp Leu Glu Glu Val Gly Glu
1               5                   10                  15

Gly Leu Arg Glu Phe Leu Gly Leu Glu Ala Gly Pro Pro Lys Pro Lys
            20                  25                  30

Pro Asn Gln Gln His Gln Asp Gln Ala Arg Gly Leu Val Leu Pro Gly
        35                  40                  45

Tyr Asn Tyr Leu Gly Pro Gly Asn Gly Leu Asp Arg Gly Glu Pro Val
    50                  55                  60

Asn Arg Ala Asp Glu Val Ala Arg Glu His Asp Ile Ser Tyr Asn Glu
65                  70                  75                  80

Gln Leu Glu Ala Gly Asp Asn Pro Tyr Leu Lys Tyr Asn His Ala Asp
                85                  90                  95

Ala Glu Phe Gln Glu Lys Leu Ala Asp Asp Thr Ser Phe Gly Gly Asn
            100                 105                 110

Leu Gly Lys Ala Val Phe Gln Ala Lys Lys Arg Val Leu Glu Pro Phe
        115                 120                 125

Gly Leu Val Glu Glu Gly Ala Lys Thr Ala Pro Thr Gly Lys Arg Ile
    130                 135                 140

Asp Asp His Phe Pro Lys Arg Lys Lys Ala Arg Thr Glu Glu Asp Ser
145                 150                 155                 160

Lys Pro Ser Thr Ser Ser Asp Ala Glu Ala Gly Pro Ser Gly Ser Gln
                165                 170                 175

Gln Leu Gln Ile Pro Ala Gln Pro Ala Ser Ser Leu Gly Ala Asp Thr
            180                 185                 190

Met Ser Ala Gly Gly Gly Pro Leu Gly Asp Asn Asn Gln Gly Ala
        195                 200                 205

Asp Gly Val Gly Asn Ala Ser Gly Asp Trp His Cys Asp Ser Thr Trp
    210                 215                 220

Met Gly Asp Arg Val Val Thr Lys Ser Thr Arg Thr Trp Val Leu Pro
225                 230                 235                 240

Ser Tyr Asn Asn His Gln Tyr Arg Glu Ile Lys Ser Gly Ser Val Asp
                245                 250                 255

Gly Ser Asn Ala Asn Ala Tyr Phe Gly Tyr Ser Thr Pro Trp Gly Tyr
            260                 265                 270

Phe Asp Phe Asn Arg Phe His Ser His Trp Ser Pro Arg Asp Trp Gln
        275                 280                 285

Arg Leu Ile Asn Asn Tyr Trp Gly Phe Arg Pro Arg Ser Leu Arg Val
    290                 295                 300

Lys Ile Phe Asn Ile Gln Val Lys Glu Val Thr Val Gln Asp Ser Thr
305                 310                 315                 320

Thr Thr Ile Ala Asn Asn Leu Thr Ser Thr Val Gln Val Phe Thr Asp
                325                 330                 335

Asp Asp Tyr Gln Leu Pro Tyr Val Val Gly Asn Gly Thr Glu Gly Cys
            340                 345                 350

Leu Pro Ala Phe Pro Pro Gln Val Phe Thr Leu Pro Gln Tyr Gly Tyr
            355                 360                 365

Ala Thr Leu Asn Arg Asp Asn Thr Glu Asn Pro Thr Glu Arg Ser Ser
370                 375                 380

Phe Phe Cys Leu Glu Tyr Phe Pro Ser Lys Met Leu Arg Thr Gly Asn
385                 390                 395                 400

Asn Phe Glu Phe Thr Tyr Asn Phe Glu Glu Val Pro Phe His Ser Ser
            405                 410                 415

Phe Ala Pro Ser Gln Asn Leu Phe Lys Leu Ala Asn Pro Leu Val Asp
            420                 425                 430

Gln Tyr Leu Tyr Arg Phe Val Ser Thr Asn Asn Thr Gly Gly Val Gln
            435                 440                 445

Phe Asn Lys Asn Leu Ala Gly Arg Tyr Ala Asn Thr Tyr Lys Asn Trp
            450                 455                 460

Phe Pro Gly Pro Met Gly Arg Thr Gln Gly Trp Asn Leu Gly Ser Gly
465                 470                 475                 480

Val Asn Arg Ala Ser Val Ser Ala Phe Ala Thr Thr Asn Arg Met Glu
            485                 490                 495

Leu Glu Gly Ala Ser Tyr Gln Val Pro Pro Gln Pro Asn Gly Met Thr
            500                 505                 510

Asn Asn Leu Gln Gly Ser Asn Thr Tyr Ala Leu Glu Asn Thr Met Ile
            515                 520                 525

Phe Asn Ser Gln Pro Ala Asn Pro Gly Thr Thr Ala Thr Tyr Leu Glu
530                 535                 540

Gly Asn Met Leu Ile Thr Ser Glu Ser Glu Thr Gln Pro Val Asn Arg
545                 550                 555                 560

Val Ala Tyr Asn Val Gly Gly Gln Met Ala Thr Asn Asn Gln Ser Ser
            565                 570                 575

Thr Thr Ala Pro Ala Thr Gly Thr Tyr Asn Leu Gln Glu Ile Val Pro
            580                 585                 590

Gly Ser Val Trp Met Glu Arg Asp Val Tyr Leu Gln Gly Pro Ile Trp
            595                 600                 605

Ala Lys Ile Pro Glu Thr Gly Ala His Phe His Pro Ser Pro Ala Met
            610                 615                 620

Gly Gly Phe Gly Leu Lys His Pro Pro Met Met Leu Ile Lys Asn
625                 630                 635                 640

Thr Pro Val Pro Gly Asn Ile Thr Ser Phe Ser Asp Val Pro Val Ser
            645                 650                 655

Ser Phe Ile Thr Gln Tyr Ser Thr Gly Gln Val Thr Val Glu Met Glu
            660                 665                 670

Trp Glu Leu Lys Lys Glu Asn Ser Lys Arg Trp Asn Pro Glu Ile Gln
            675                 680                 685

Tyr Thr Asn Asn Tyr Asn Asp Pro Gln Phe Val Asp Phe Ala Pro Asp
            690                 695                 700

Ser Thr Gly Glu Tyr Arg Thr Thr Arg Pro Ile Gly Thr Arg Tyr Leu
705                 710                 715                 720

Thr Arg Pro Leu

<210> SEQ ID NO 78
<211> LENGTH: 12
<212> TYPE: PRT

```
<213> ORGANISM: Artificial Sequence
<220> FEATURE:
<223> OTHER INFORMATION: Synthetic Polypeptide

<400> SEQUENCE: 78

Leu Ala Asn Pro Leu Val Asp Gln Tyr Leu Tyr Arg
1               5                   10

<210> SEQ ID NO 79
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 79

Ile Pro Glu Thr Gly Ala His Phe His Pro Ser Pro Ala Met Gly Gly
1               5                   10                  15

Phe Gly Leu Lys
            20

<210> SEQ ID NO 80
<211> LENGTH: 21
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (11)..(11)
<223> OTHER INFORMATION: n is a, u, or c
<220> FEATURE:
<221> NAME/KEY: misc_feature
<222> LOCATION: (12)..(12)
<223> OTHER INFORMATION: n is a, g, or c
<220> FEATURE:
<221> NAME/KEY: misc_feature
<222> LOCATION: (13)..(13)
<223> OTHER INFORMATION: n is g or u
<220> FEATURE:
<221> NAME/KEY: misc_feature
<222> LOCATION: (15)..(15)
<223> OTHER INFORMATION: n is g or u
<220> FEATURE:
<221> NAME/KEY: misc_feature
<222> LOCATION: (16)..(16)
<223> OTHER INFORMATION: n is a, u, or c

<400> SEQUENCE: 80
gcgcagaucu nnnunnaugg c                                         21

<210> SEQ ID NO 81
<211> LENGTH: 11
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: n is a, u, or c
<220> FEATURE:
<221> NAME/KEY: misc_feature
<222> LOCATION: (2)..(2)
<223> OTHER INFORMATION: n is a or g
<220> FEATURE:
<221> NAME/KEY: misc_feature
<222> LOCATION: (3)..(3)
<223> OTHER INFORMATION: n is g or u
<220> FEATURE:
<221> NAME/KEY: misc_feature
<222> LOCATION: (5)..(5)
```

```
<223> OTHER INFORMATION: n is g or u
<220> FEATURE:
<221> NAME/KEY: misc_feature
<222> LOCATION: (6)..(6)
<223> OTHER INFORMATION: n is c or u
<220> FEATURE:
<221> NAME/KEY: misc_feature
<222> LOCATION: (10)..(10)
<223> OTHER INFORMATION: n is g or u
<220> FEATURE:
<221> NAME/KEY: misc_feature
<222> LOCATION: (11)..(11)
<223> OTHER INFORMATION: n is g or c

<400> SEQUENCE: 81
nnnunnaugn n                                                         11
```